United States Patent
Carpino et al.

(10) Patent No.: US 6,313,140 B1
(45) Date of Patent: *Nov. 6, 2001

(54) METHOD OF TREATMENT USING CERTAIN GROWTH-HORMONE SECRET AGOGUES

(75) Inventors: Philip A Carpino, Groton, CT (US); Paul A DaSilva-Jardine, Providence, RI (US); Bruce A Lefker; John A Ragan, both of Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/593,581

(22) Filed: Jun. 13, 2000

Related U.S. Application Data

(60) Continuation of application No. 09/259,691, filed on Mar. 1, 1999, now Pat. No. 6,107,306, which is a division of application No. 09/068,566, filed on May 21, 1998, now abandoned, and a continuation of application No. PCT/IB96/01353, filed on Dec. 4, 1996.
(60) Provisional application No. 60/009,469, filed on Dec. 28, 1995.

(51) Int. Cl.$^7$ ............................................... A61K 31/435
(52) U.S. Cl. .................................................. 514/303
(58) Field of Search ............................ 514/303; 546/118

(56) References Cited

U.S. PATENT DOCUMENTS 6,107,306 * 8/2000 Carpino et al. ...................... 546/119

FOREIGN PATENT DOCUMENTS

| | | | |
|---|---|---|---|
| 2221808 | 11/1972 | (DE) | C07D/57/22 |
| 0662481 | 7/1995 | (EP) | C07K/5/023 |
| 9511029 | 4/1995 | (WO) | A61K/31/66 |
| 9513069 | 5/1995 | (WO) | A61K/31/445 |
| 9528173 | 10/1995 | (WO) | A61K/38/27 |
| 9528174 | 10/1995 | (WO) | A61K/38/30 |
| 0613265 | 5/1996 | (WO) | A61K/31/445 |
| 9615148 | 5/1996 | (WO) | C07K/14/60 |
| 9622997 | 8/1996 | (WO) | C07K/5/02 |
| 9624580 | 8/1996 | (WO) | C07C/335/12 |
| 9624587 | 8/1996 | (WO) | C07D/215/08 |
| 9706803 | 2/1997 | (WO) | A61K/31/50 |
| 9707117 | 2/1997 | (WO) | C07D/403/12 |

OTHER PUBLICATIONS

Tetrahedron, Moreno–Manas vol. 50, No. 2, 1994, pp. 515–528.
Eur. Journal of Endocrinology, Marie Degerhblad et al, 1995, 133:180–8.
Eur. Journal Endocrinology, Jens Ol Jorgensen et al, 1994, 130:224–8.
Journal of Clinical Endocrinology and Metabolish, K. C. Copeland et al, 1994, vol. 78, pp. 1040–1047.
Journal of Clinical Endocrinilogy and Metabolism, Joseph A. Aloi et al, 1994, vol. 79, pp. 943–949.
The New England Journal of Medicine, Evan Loh et al, 1996, vol. 334, No. 13, pp. 856–857.
The New England Journal of Medicine, Serafino Fazio et al, vol. 334, No. 13, 1996, pp. 809–814.
Circulation, Antonio Cittadini et al, vol. 93, No. 4, Feb. 15, 1996, pp. 800–808.
Hormone Res. 1995, pp. 93–99, Thord Rosen.
The Martindale The Extra Pharma Copia 30a. Ed. The Parm Press, Londres, 1993, pp. 655–657.
Circulation, Renhui Yang et al, vol. 92, No. 2, Jul. 15, 1995, pp. 262–267.

* cited by examiner

*Primary Examiner*—Bernard Dentz
(74) *Attorney, Agent, or Firm*—Peter C. Richardson; Gregg C. Benson; Robert T. Ronau

(57) ABSTRACT

This invention is directed to compounds of the formula

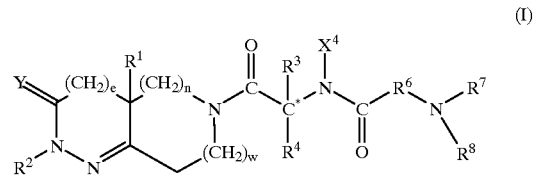

(I)

and the pharmaceutically-acceptable salts thereof, where the substituents are as defined in the Specification, which are growth hormone secretogogues and which increase the level of endogenous growth hormone. The compounds of this invention are useful for the treatment and prevention of osteoporosis, congestive heart failure, frailty associated with aging, obesity; accelerating bone fracture repair, attenuating protein catabolic response after a major operation, reducing cachexia and protein loss due to chronic illness, accelerating wound healing, or accelerating the recovery of burn patients or patients having undergone major surgery; improving muscle strength, mobility, maintenance of skin thickness, metabolic homeostasis or renal homeostasis. The compounds of the present invention are also useful in treating osteoporosis when used in combination with: a bisphosphonate compound such as alendronate; estrogen; premarin, and optionally progesterone; an estrogen agonist or antagonist; or calcitonin, and pharmaceutical compositions useful therefor. Further, the present invention is directed to pharmaceutical compositions useful for increasing the endogenous production or release of growth hormone in a human or other animal which comprises an effective amount of a compound of the present invention and a growth hormone secretagogue selected from GHRP-6, Hexarelin, GHRP-1, growth hormone releasing factor (GRF), IGF-1, IGF-2 or B-HT920. The invention is also directed to intermediates useful in the preparation of compounds of formula I.

10 Claims, No Drawings

METHOD OF TREATMENT USING CERTAIN GROWTH-HORMONE SECRET AGOGUES

CROSS REFERENCE TO RELATED APPLICATIONS

This application is a continuation of U.S. application Ser. No. 09/259,691, filed Mar. 1, 1999, now U.S. Pat. No. 6,107,306 entitled "Growth-Hormone Secretagogues", which is a divisional of U.S. application Ser. No. 09/068,566, filed May 21, 1998 now abandoned which is the national stage under 35 U.S.C. §371 (c) of International Patent Application No. PCT/IB96/01353, filed Dec. 4, 1996, claiming priority to U.S. provisional application No. 60/009,469, filed Dec. 28, 1995.

This invention relates to dipeptide compounds which are growth hormone secretagogues and are useful for the treatment and prevention of osteoporosis.

BACKGROUND OF THE INVENTION

Growth hormone (GH), which is secreted from the pituitary gland, stimulates growth of all tissues of the body that are capable of growing. In addition, growth hormone is known to have the following basic effects on the metabolic process of the body:

1. Increased rate of protein synthesis in substantially all cells of the body;
2. Decreased rate of carbohydrate utilization in cells of the body;
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in an expensive product, and carried with it the risk that a disease associated with the source of the pituitary gland could be transmitted to the recipient of the growth hormone (e.g., Jacob-Creutzfeld disease). Recently, recombinant growth hormone has become available which, while no longer carrying any risk of disease transmission, is still a very expensive product which must be given by injection or by a nasal spray.

Most GH deficiencies are caused by defects in GH release, not primary defects in pituitary synthesis of GH. Therefore, an alternative strategy for normalizing serum GH levels is by stimulating its release from somatotrophs. Increasing GH secretion can be achieved by stimulating or inhibiting various neurotransmitter systems in the brain and hypothalamus. As a result, the development of synthetic growth hormone-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

Physiologic and pharmacologic stimulators of GH secretion include arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GHRF) or an unknown endogenous growth hormone-releasing hormone or all of these.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. WO 94/13696 refers to certain spiropiperidines and homologues which promote release of growth hormone. Preferred compounds are of the general structure shown below.

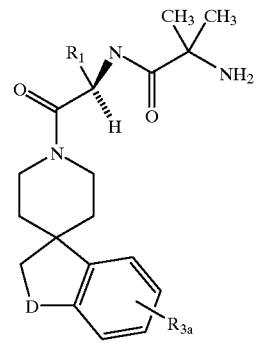

WO 94/11012 refers to certain dipeptides that promote release of growth hormone. These dipeptides have the general structure

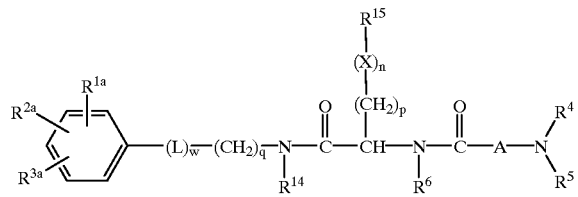

where L is

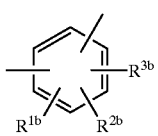

The compounds of WO 94/11012 and WO 94/13696 are reported to be useful in the treatment of osteoporosis in combination with parathyroid hormone or a bisphosphonate.

SUMMARY OF THE INVENTION

This invention provides compounds of the formula:

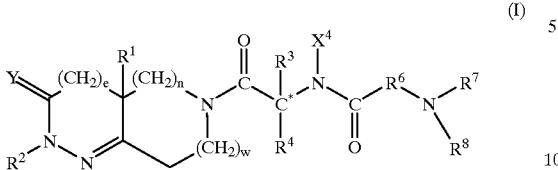

(I)

the racemic-diastereomeric mixtures and optical isomers of said compounds and the pharmaceutically-acceptable salts and prodrugs thereof,
wherein
  e is 0 or 1;
  n and w are each independently 0, 1 or 2, provided that w and n cannot both be 0 at the same time;
  Y is oxygen or sulfur;
  $R^1$ is hydrogen, —CN, —$(CH_2)_q N(X^6)C(O)X^6$, —$(CH_2)_q N(X^6)C(O)(CH_2)_t$—$A^1$, —$(CH_2)_q N(X^6)SO_2(CH_2)_t$—$A^1$, —$(CH_2)_q N(X^6)SO_2 X^6$, —$(CH_2)_q N(X^6)C(O)N(X^6)(CH_2)_t$—$A^1$, —$(CH_2)_q N(X^6)C(O)N(X^6)(X^6)$, —$(CH_2)_q C(O)N(X^6)(X^6)$, —$(CH_2)_q C(O)N(X^6)(CH_2)_t$—$A^1$, —$(CH_2)_q C(O)OX^6$, —$(CH_2)_q C(O)O(CH_2)_t$—$A^1$, —$(CH_2)_q OX^6$, —$(CH_2)_q OC(O)X^6$, —$(CH_2)_q OC(O)(CH_2)_t$—$A^1$, —$(CH_2)_q OC(O)N(X^6)(CH_2)_t$—$A^1$, —$(CH_2)_q OC(O)N(X^6)(X^6)$, —$(CH_2)_q C(O)X^6$, —$(CH_2)_q C(O)(CH_2)_t$—$A^1$, —$(CH_2)_q N(X^6)C(O)OX^6$, —$(CH_2)_q N(X^6)SO_2 N(X^6)(X^6)$, —$(CH_2)_q S(O)_m X^6$, —$(CH_2)_q S(O)_m (CH_2)_t$—$A^1$, —$(C_1-C_{10})$alkyl, —$(CH_2)_t$—$A^1$, —$(CH_2)_q$—$(C_3-C_7)$cycloalkyl, —$(CH_2)_q$—$Y^1$—$(C_1-C_6)$alkyl, —$(CH_2)_q$—$Y^1$—$(CH_2)_t$—$A^1$ or —$(CH_2)_q$—$Y^1$—$(CH_2)_t$—$(C_3-C_7)$cycloalkyl;
    where the alkyl and cycloalkyl groups in the definition of $R^1$ are optionally substituted with $(C_1-C_4)$alkyl, hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl or 1, 2 or 3 fluoro; $Y^1$ is O, $S(O)_m$, —$C(O)NX^6$—, —CH=CH—, —C≡C—, —$N(X^6)$C(O)—, —$C(O)NX^6$—, —C(O)O—, —OC(O)N($X^6$)— or —OC(O)—;
  q is 0, 1, 2, 3 or 4;
  t is 0, 1, 2 or 3;
    said $(CH_2)_q$ group and $(CH_2)_t$ group may each be optionally substituted with hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5yl, 1, 2 or 3 fluoro, or 1 or 2 $(C_1-C_4)$alkyl;
  $R^2$ is hydrogen, $(C_1-C_8)$alkyl, —$(C_0-C_3)$alkyl-$(C_3-C_8)$cycloalkyl, —$(C_1-C_4)$alkyl-$A^1$ or $A^1$; where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1-C_6)$alkyl, —$C(O)A^1$, —$C(O)(X^6)$, $CF_3$, CN or 1, 2 or 3 halogen;
  $R^3$ is $A^1$, $(C_1-C_{10})$alkyl, —$(C_1-C_6)$alkyl-$A^1$, —$(C_1-C_6)$alkyl-$(C_3-C_7)$cycloalkyl, —$(C_1-C_5)$alkyl-$X^1$—$(C_1-C_5)$alkyl, —$(C_1-C_5)$alkyl-$X^1$—$(C_0-C_5)$alkyl-$A^1$ or —$(C_1-C_5)$alkyl-$X^1$—$(C_1-C_5)$alkyl-$(C_3-C_7)$cycloalkyl;
    where the alkyl groups in the definition of $R^3$ are optionally substituted with, —$S(O)_m(C_1-C_6)$alkyl, —$C(O)OX^3$, 1, 2, 3, 4 or 5 halogens, or 1, 2 or 3 $OX^3$;
  $X^1$ is O, $S(O)_m$, —$N(X^2)C(O)$—, —$C(O)N(X^2)$—, —OC(O)—, —C(O)O—, —$CX^2$=$CX^2$—, —$N(X^2)C(O)O$—, —$OC(O)N(X^2)$— or —C≡C—;
  $R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sutfur and nitrogen, or is a bicyclic ring system consisting of a partially saturated or fully saturated 5- or 6-membered ring, fused to a partially saturated, fully unsaturated or fully saturated 5 or 6-membered ring, optionally having 1- to 4 heteroatoms independently selected from the group consisting of nitrogen, sulfur and oxygen;
  $X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;
  $R^6$ is a bond or is

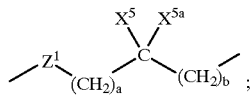

where a and b are independently 0, 1, 2 or 3;
  $X^5$ and $X^{5a}$ are each independently selected from the group consisting of hydrogen, trifluoromethyl, $A^1$ and optionally substituted $(C_1-C_6)$alkyl;
    the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$alkyl, —$C(O)OX^2$, $(C_3-C_7)$cycloalkyl, —$N(X^2)(X^2)$ and —$C(O)N(X^2)(X^2)$;
  or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ or $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom;
  or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;
  or $X^5$ is taken together with $X^{5a}$ and the carbon atom to which they are attached and form a bicydic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
  $Z^1$ is a bond, O or N—$X^2$, provided that when a and b are both 0 then $Z^1$ is not N—$X^2$ or O;

$R^7$ and $R^8$ are independently hydrogen or optionally substituted $(C_1-C_6)$alkyl;
where the optionally substituted $(C_1-C_6)$alkyl in the definition of $R^7$ and $R^8$ is optionally independently substituted with $A^1$, —C(O)O—$(C_1-C_6)$alkyl, —S(O)$_m$($C_1-C_8$)alkyl, 1 to 5 halogens, 1 to 3 hydroxy, 1 to 3 —O—C(O)($C_1-C_{10}$)alkyl or 1 to 3 $(C_1-C_6)$alkoxy; or $R^7$ and $R^8$ can be taken together to form —(CH$_2$)$_r$—L—(CH$_2$)$_r$—;
where L is C(X$^2$)(X$^2$), S(O)$_m$ or N(X$^2$);

$A^1$ for each occurrence is independently $(C_5-C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5 or 6-membered ring, optionally having 1 to 4 heteroatoms independently selected from the group consisting of nitrogen, sulfur and oxygen, fused to a partially saturated, fully saturated or fully unsaturated 5 or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N(X$^6$)(X$^6$), —C(O)O X$^6$, oxo, $(C_1-C_6)$alkyl, nitro, cyano, benzyl, —S(O)$_m$ $(C_1-C_6)$alkyl, 1H-tetrazol-5-yl, phenyl, phenoxy, phenylalkyloxy, halophenyl, methylenedioxy, —N(X$^6$)(X$^6$), —N(X$^6$)C(O)(X$^6$), —SO$_2$N(X$^6$)(X$^6$), —N(X$^6$)SO$_2$-phenyl, —N(X$^6$)SO$_2$X$^6$, —CONX$^{11}$X$^{12}$, —SO$_2$NX$^{11}$X$^{12}$, —NX$^6$SO$_2$X$^{12}$, —NX$^6$CONX$^{11}$X$^{12}$, —NX$^6$SO$_2$NX$^{11}$X$^{12}$, —NX$^6$C(O)X$^{12}$, imidazolyl, thiazolyl or tetrazolyl, provided that if $A^1$ is optionally substituted with methylenedioxy then it can only be substituted with one methylenedioxy;

where X$^{11}$ is hydrogen or optionally substituted $(C_1-C_6)$alkyl;
the optionally substituted $(C_1-C_6)$alkyl defined for X$^{11}$ is optionally independently substituted with phenyl, phenoxy, $(C_1-C_6)$alkoxycarbonyl, —S(O)$_m$($C_1-C_6$)alkyl 1 to 5 halogens, 1 to 3 hydroxy, 1 to 3 $(C_1-C_{10})$alkanoyloxy or 1 to 3 $(C_1-C_6)$alkoxy;

X$^{12}$ is hydrogen, $(C_1-C_6)$alkyl, phenyl, thiazolyl, imidazolyl, furyl or thienyl, provided that when X$^{12}$ is not hydrogen, X$^{12}$ is optionally substituted with one to three substituents independently selected from the group consisting of Cl, F, CH$_3$, OCH$_3$, OCF$_3$ and CF$_3$;

or X$^{11}$ and X$^{12}$ are taken together to form —(CH$_2$)$_r$—L$^1$—(CH$_2$)$_r$—;
L$^1$ is C(X$^2$)(X$^2$), O, S(O)$_m$ or N(X$^2$);

r for each occurrence is independently 1, 2 or 3;

X$^2$ for each occurrence is independently hydrogen, optionally substituted $(C_1-C_6)$alkyl, or optionally substituted $(C_3-C_7)$cycloalkyl, where the optionally substituted $(C_1-C_6)$alkyl and optionally substituted $(C_3-C_7)$cycloalkyl in the definition of X$^2$ are optionally independently substituted with —S(O)$_m$($C_1-C_6$)alkyl, —C(O)OX$^3$, 1 to 5 halogens or 1 to 3 OX$^3$;

X$^3$ for each occurrence is independently hydrogen or $(C_1-C_6)$alkyl;

X$^6$ is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenatedcloalkyl, where optionally substituted $(C_1-C_6)$alkyl and optionally substituted $(C_3-C_7)$cycloalkyl in the definition of X$^6$ is optionally independently substituted by 1 or 2 $(C_1-C_4)$alkyl, hydroxyl, $(C_1-C_4)$alkoxy, carboxyl, CONH$_2$, —S(O)$_m$ $(C_1-C_6)$alkyl, carboxylate $(C_1-C_4)$alkyl ester, or 1H-tetrazol-5-yl; or when there are two X$^6$ groups on one atom and both X$^6$ are independently $(C_1-C_6)$alkyl, the two $(C_1-C_6)$alkyl groups may be optionally joined and, together with the atom to which the two )e groups are attached, form a 4- to 9-membered ring optionally having oxygen, sulfur or NX$^7$;

X$^7$ is hydrogen or $(C_1-C_6)$alkyl optionally substituted with hydroxyl; and m for each occurrence is independently 0, 1 or 2;
with the proviso that:
X$^6$ and X$^{12}$ cannot be hydrogen when it is attached to C(O) or SO$_2$ in the form C(O)X$^6$, C(O)X$^{12}$, SO$_2$X$^6$ or SO$_2$X$^{12}$; and when R$^6$ is a bond then L is N(X$^2$) and each r in the definition —(CH$_2$)$_r$—L—(CH$_2$)$_r$-is independently 2 or 3.

A preferred group of compounds, designated the "A Group", contains those compounds having the formula I as shown hereinabove wherein X$^4$ is hydrogen; R$^4$ is hydrogen or methyl; R$^7$ is hydrogen or $(C_1-C_3)$alkyl; R$^8$ is hydrogen or $(C_1-C_3)$alkyl optionally substituted with one or two hydroxyl groups;

R$^6$ is

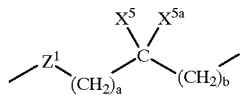

where Z$^1$ is a bond and a is 0 or 1;
X$^6$ and X$^{5a}$ are each independently hydrogen, trifluoromethyl, phenyl, optionally substituted $(C_1-C_6)$alkyl;
where the optionally substituted $(C_1-C_6)$alkyl is optionally substituted with OX$^2$, imidazolyl, phenyl, indolyl, p-hydroxyphenyl, $(C_5-C_7)$cycloalkyl, —S(O)$_m$($C_1-C_6$)alkyl, —N(X$^2$)(X$^2$) or —C(O)N(X$^2$)(X$^2$);

or X$^5$ and R$^7$ are taken together to form a $(C_1-C_5)$alkylene bridge, and the other substituents not defined for the "A Group" compounds are as defined for formula (I) hereinabove.

A group of compounds, which is preferred among the "A Group" of compounds, designated the "B Group", contains those compounds of the "A Group", having the formula I as shown hereinabove, wherein b is 0; X$^5$ and X$^{5a}$ are each independently hydrogen, $(C_1-C_3)$alkyl or hydroxy$(C_1-C_3)$ alkyl; R$^3$ is selected from the group consisting of 1-indolyl-CH$_2$—, 2-indolyl-CH$_2$—, 3-indolyl-CH$_2$—, 1-naphthyl-CH$_2$—, 2-naphthyl-CH$_2$—, 1-benzimidazolyl-CH$_2$—, 2-benzimidazolyl-CH$_2$—, phenyl-$(C_1-C_4)$alkyl-, 2-pyridyl-$(C_1-C_4)$alkyl-, 3-pyridyl-$(C_1-C_4)$alkyl-, 4-pyridyl-$(C_1-C_4)$alkyl-, phenyl-CH$_2$—S—CH$_2$—, thienyl-$(C_1-C_4)$alkyl-, phenyl-$(C_0$-$C_3)$alkyl-O—$CH_2$—, phenyl-$CH_2$—O-phenyl-$CH_2$—, and 3-benzothienyl-$CH_2$—;

where the aryl portion(s) of the groups defined for $R^3$ are optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds, which is preferred among the "B Group" of compounds, designated the "C Group", contain those compounds of the "B Group", having the formula I as shown hereinabove, wherein $R^4$ is hydrogen; a is 0; n is 1 or 2; w is 0 or 1; $X^5$ and $X^{5a}$ are each independently, hydrogen, methyl or hydroxymethyl, provided that when $X^5$ is hydrogen then $X^{5a}$ is not hydrogen;

$R^7$ and $R^8$ are each hydrogen; and $R^3$ is phenyl-$CH_2$—O—$CH_2$—, phenyl-$CH_2$—S—$CH_2$—, 1-naphthyl-$CH_2$—, 2-naphthyl-$CH_2$—, phenyl-$(CH_2)_3$— or 3-indolyl-$CH_2$—;

where the aryl portion of the groups defined for $R^3$ is optionally substituted with one to three substituents, each substituent being independently selected from the group consisting of fluoro, chloro, methyl, $OCH_3$, $OCF_2H$, $OCF_3$ and $CF_3$.

A group of compounds, which is preferred among the "C Group" of compounds, designated the "D Group", contains those compounds of the "C Group", having the formula I as shown hereinabove, wherein $R^1$ is —$(CH_2)_t$—$A^1$, —$CH_2)_q$—$(C_3$-$C_7)$cycloalkyl or $(C_1$-$C_{10})$alkyl;

where $A^1$ in the definiton of $R^1$ is optionally substituted with one to three substituents, each substituent being independently selected from the group consisting of fluoro, chloro, methyl, $OCH_3$, $OCF_2H$, $OCF_3$ and $CF_3$; the cycloalkyl and alkyl groups in the definition of $R^1$ are optionally substituted with $(C_1$-$C_4)$alkyl, hydroxyl, $(C_1$-$C_4)$alkoxy, carboxyl, $CONH_2$, —$S(O)_m(C_1$-$C_6)$alkyl, —$CO_2(C_1$-$C_4)$alkyl ester, 1H-tetrazol-5-yl or 1 to 3 fluoro;

Y is O; $R^2$ is hydrogen, —$(C_0$-$C_3)$alkyl-$(C_3$-$C_8)$ cycloalkyl, phenyl or $(C_1$-$C_8)$alkyl where the $(C_1$-$C_8)$ alkyl group is optionally substituted with hydroxyl, —$CF_3$ or 1 to 3 halogen.

A group of compounds, which is preferred among the "D Group" of compounds, designated the "E Group", contains those compounds of the "D Group" wherein w is 0 and n is 1.

Another group of compounds, which is preferred among the "D Group" of compounds, designated the "F Group", are those compounds of the "D Group", having the formula I as shown hereinabove, wherein e is 0; n and w are each 1;

$R^1$ is —$(CH_2)_t$—$A^1$;

where $A^1$ in the definition of $R^1$ is phenyl, thienyl, thiazolyl, pyridyl or pyrimidyl which is optionally substituted with one to three substituents, each substituent being independently selected from the group consisting of F, Cl, Me, OMe, $CF_3$, $OCF_3$ and $OCF_2H$;

t is 0, 1 or 2;

and $R^3$ is phenyl-$CH_2$—O—$CH_2$—, phenyl$(CH_2)_3$— or 3-indolyl-$CH_2$—, where the aryl portion is optionally substituted with one to three substituents, each substituent being independently selected from the group consisting of F, Cl, Me, OMe, $CF_3$, $OCF_3$ or $OCF_2H$.

A group of compounds, which is preferred among the "F Group" of compounds, designated the "G Group", contains those compounds of the "F Group", having the formula I as shown hereinabove, wherein $X^5$ and $X^{5a}$ are each methyl; $R^1$ is —$CH_2$-phenyl, —$CH_2$-fluoro-phenyl, —$CH_2$-pyridyl or —$CH_2$-thiazolyl and $R^2$ is hydrogen, methyl, ethyl, t-butyl or —$CH_2CF_3$.

A group of compounds, which is preferred among the "G Group" of compounds, designated the "$G^1$ Group", contains those compounds of the "G Group", and have the formula

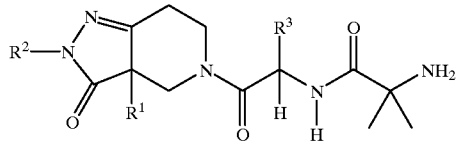

the racemic-diastereomeric mixtures and optical isomers of said compounds wherein $R^1$ is —$CH_2$-phenyl, $R^2$ is methyl and $R^3$ is —$(CH_2)_3$-phenyl;

$R^1$ is —$CH_2$-phenyl, $R^2$ is methyl and $R^3$ is 3-indolyl-$CH_2$—;

$R^1$ is —$CH_2$-phenyl, $R^2$ is ethyl and $R^3$ is 3-indolyl-$CH_2$—;

$R^1$ is —$CH_2$-4-fluoro-phenyl, $R^2$ is methyl and $R^3$ is 3-indolyl-$CH_2$—;

$R^1$ is —$CH_2$-phenyl, $R^2$ is methyl and $R^3$ is —$CH_2$—O—$CH_2$-phenyl;

$R^1$ is —$CH_2$-phenyl, $R^2$ is ethyl and $R^3$ is —$CH_2$—O—$CH_2$-phenyl;

$R^1$ is —$CH_2$-phenyl, $R^2$ is —$CH_2$—$CF_3$ and $R^3$ is —$CH_2$—O—$CH_2$-phenyl;

$R^1$ is —$CH_2$-4-fluoro-phenyl, $R^2$ is methyl and $R^3$ is —$CH_2$—O—$CH_2$-phenyl;

$R^1$ is $CH_2$-phenyl, $R^2$ is t-butyl and $R^3$ is —$CH_2$—O—$CH_2$-phenyl; or $R^1$ is —$CH_2$-phenyl, $R^2$ is methyl and $R^3$ is —$CH_2$—O—$CH_2$-3,4-di-fluoro-phenyl.

The diastereomeric mixture of 2-amino-N-[2-(3a-(R,S) benzyl-2-methyl-3-oxo-2,3,3a,4,6,7-hexahydro-pyrazolo[4, 3-c]pyridin-5-yl)-1-(R)-(3,4-difluoro-benzylboxymethyl)-2-oxo-ethyl]-2-methyl-propionamide is preferred among the "$G^1$ Group" of compounds and the separated 3a-(R) and 3a-(S) isomers are preferred of the diastereomeric mixture.

A group of compounds, which is preferred among the "G Group" of compounds, designated the "H Group", contains those compounds of the "G Group", having the formula I as shown hereinabove, wherein $R^1$ is —$CH_2$-phenyl and $R^3$ is phenyl-$(CH_2)_3$—.

The diastereomeric mixture of 2-amino-N-[1-(3a-(R,S)-benzyl-2-methyl-3-oxo-2,3,3a,4,6,7-hexahydro-pyrazolo[4, 3-c]pyridine-5-carbonyl)-4-phenyl-(R)-butyl]-isobutyramide is preferred among the "H Group" of compounds and the separated 3a-(R) and 3a-(S) isomers are preferred of the diastereomeric mixture.

A group of compounds, which is preferred among the "G Group" of compounds, designated the "I Group", contains those compounds of the "G Group" wherein $R^1$ is —$CH_2$-phenyl or —$CH_2$-4-fluoro-phenyl and $R^3$ is 3-indolyl-$CH_2$—.

The diastereomeric mixture of 2-amino-N-[2-(3a-(R,S)-benzyl-2-methyl-3-oxo-2,3,3a,4,6,7-hexahydro-pyrazolo-[4,3-c]pyridin-5-yl)-1-(R)-(1H-indol-3-ylmethyl)-2-oxo-ethyl]-isobutyramide is preferred among the "I Group" of compounds and the separated 3a-(R) and 3a-(S) isomers are preferred of the diastereomeric mixture.

The diasteromeric mixture of 2-amino-N-[2-(3a-(R,S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide is also preferred among the "I Group" of compounds and the separated 3a-(R) and 3a-(S) isomers are preferred of the diastereomeric mixture.

The diastereomeric mixture of 2-amino-N-[2-[3a-(R,S)-(4-fluoro-benzyl)-2-methyl-3-oxo-2,3,3a,4,6,7-hexahydro-pyrazolo[4,3-c]pyridin-5yl]-1-(R)-(1H-indol-3-ylmethyl)-2-oxo-ethyl]-isobutyramide is also preferred among the "I Group" of compounds and the separated 3a-(R) and 3a-(S) isomers are preferred of the diastereomeric mixture.

A group of compounds which is preferred among the "G Group", designated the "J Group", contains those compounds of the "G Group" wherein $R^1$ is —$CH_2$-phenyl or —$CH_2$-4-fluoro-phenyl and $R^3$ is phenyl-$CH_2$—O—$CH_3$—.

The diastereomeric mixture of 2-amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide is preferred among the "J Group" of compounds, the separated 3a-(R) and 3a-(S) isomers are preferred of the diastereomeric mixture, the 3a-(R) isomer is preferred over the 3a-(S) isomer, and the L-tartaric acid salt of the 3a-(R) isomer is a preferred salt.

The diastereomeric mixture of 2-amino-N-[2-(3a-(R,S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide is also preferred among the "J Group" of compounds and the separated 3a-(R) and 3a-(S) isomers are preferred of the diastereomeric mixture.

The diastereomeric mixture of 2-amino-N-{2-[3a-(R,S)-benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo-ethyl}-isobutyramide is also preferred among the "J Group" of compounds, the separated 3a-(R) and 3a-(S) isomers are preferred of the diastereomeric mixture and the 3a-(R) isomer is preferred over the 3a-(S) isomer.

The diastereomeric mixture of 2-amino-N-{1-(R)-benzyloxymethyl-2-[3a-(R,S)-(4-fluoro-benzyl)-2-methyl-3-oxo-2,3,3a,4,6,7-hexahydro-pyrazolo[4,3-c]pyridin-5-yl]-2-oxo-ethyl}-isobutyramide is also preferred among the "J Group" of compounds and the separated 3a-(R) and 3a-(S) isomers are preferred of the diastereomeric mixture.

The diastereomeric mixture of 2-amino-N-[2-(3a-(R,S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide is also preferred among the "J Group" of compounds and the separated 3a-(R) and 3a-(S) isomers are preferred of the diastereomeric mixture.

A group of compounds which is preferred among the "D Group", designated the "K Group", contains those compounds of the "D Group"

wherein e is 1; n is 1; w is 1; $R^1$ is —$(CH_2)_t$—$A^1$;
where $A^1$ in the definition of $R^1$ is phenyl, thienyl, thiazolyl, pyridyl or pyrimidyl which is optionally substituted with one to three substituents, each substituent being independently selected from the group consisting of F, Cl, Me, OMe, $CF_3$, $OCF_3$ and $OCF_2H$;
t is 0, 1 or 2;
and $R^3$ is phenyl-$CH_2$—O—$CH_2$—, phenyl-$(CH_2)_3$— or 3-indolyl-$CH_2$—, where the aryl portion is optionally substituted with one to three substituents, each substituent being independently selected from the group consisting of F, Cl, Me, OMe, $CF_3$, $OCF_3$ or $OCF_2H$.

A group of compounds which is preferred among the "K Group" of compounds, designated the "L Group", are those compounds of the "K Group" wherein $X^5$ and $X^{5a}$ are each methyl; $R^1$ is —$CH_2$-phenyl, —$CH_2$—4-fluoro-phenyl, —$CH_2$-pyridyl or —$CH_2$-thiazolyl and $R^2$ is hydrogen, methyl, ethyl, t-butyl or —$CH_2CF_3$.

A group of compounds which is preferred among the "L Group", designated the "$L^1$ Group", are those compounds of the "L Group" wherein $R^1$ is —$CH_2$-phenyl; $R^2$ is hydrogen or methyl and $R^3$ is —$CH_2$—O—$CH_2$-phenyl.

The diastereomeric mixture of 2-amino-N-[2-(3a-(R,S)-benzyl-3-oxo-2,3,3a,4,6,7-hexahydro-pyrazolo[4.3-c]pyridin-5-yl)-1-(R)-benzyloxymethyl-2-oxo-ethyl]-isobutyramide is preferred among the "J Group", the separated 3a-(R) and 3a-(S) isomers are preferred of the diastereomeric mixture and the 3a-(R) isomer is preferred over the 3a-(S) isomer.

Another group of compounds, which is preferred among the "A Group" of compounds, designated the "M Group", contains those compounds of the "A Group", having the formula I as shown hereinabove, wherein b is 0; $X^5$ and $X^{5a}$ are each independently hydrogen, $(C_{1\text{-}3})$ alkyl or hydroxy$(C_1$–$C_3)$alkyl;

$R^3$ is selected from the group consisting of 1-indolyl-$CH_2$—, 2-indolyl-$CH_2$—, 3-indolyl-$CH_2$—, 1-naphthyl-$CH_2$—, 2-naphthyl-$CH_2$—, 1-benzimidazolyl-$CH_2$—, 2-benzimidazolyl-$CH_2$—, phenyl-$(C_1$–$C_4)$alkyl-, 2-pyridyl-$(C_1$–$C_4)$alkyl-, 3-pyridyl-$(C_1$–$C_4)$alkyl-, 4-pyridyl-$(C_1$–$C_4)$alkyl-, phenyl-$CH_2$—S—$CH_2$—, thienyl-$(C_1$–$C_4)$alkyl-, phenyl-$(C_0$–$C_3)$alkyl—O—$CH_2$—, phenyl-$CH_2$—O-phenyl-$CH_2$—, 3-benzothienyl-$CH_2$—, thienyl-$CH_2$—O—$CH_2$—, thiazolyl-$CH_2$—O—$CH_2$—, pyridyl-$CH_2$—O—$CH_2$—, pyrimidyl-$CH_2$—O—$CH_2$— and phenyl-O—$CH_2$—$CH_2$;

where the aryl portion(s) of the groups defined for $R^3$ are optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds, which is preferred among the "M Group" of compounds, designated the "$M^1$ Group", contains those compounds of the "M Group", having the formula I as shown hereinabove, wherein $R^4$ is hydrogen; a is 0; n is 1; w is 1; e is 0; $X^5$ and $X^{5a}$ are each independently, hydrogen, methyl or hydroxymethyl, provided that when $X^5$ is hydrogen then $X^{5a}$ is not hydrogen; $R^7$ and $R^8$ are each hydrogen; Y is oxygen; $R^2$ is hydrogen, methyl, ethyl, propyl, i-propyl, t-butyl, —$CH_2CF_3$, $CF_3$ or —$CH_2$-cyclopropyl; $R^1$ is $CH_2$—$A^1$; where $A^1$ in the definition of $R^1$ is phenyl, thienyl, thiazolyl, pyridyl or pyrimidyl which is optionally substituted with one to three substituents, each substituent being independently selected from the group consisting of F, Cl, Me, OMe, $CF_3$, $OCF_3$ and $OCF_2H$; and $R^3$ is phenyl-$CH_2$—O—$CH_2$—, phenyl-$(CH_2)_3$—, 3-indolyl-$CH_2$—, thienyl-$CH_2$—O—$CH_2$, thiazolyl-$CH_2$—O—$CH_2$—, pyridyl-$CH_2$—O—$CH_2$—, pyrimidyl-$CH_2$—O—$CH_2$— or pheny-O—$CH_2$—$CH_2$, where the aryl portion is optionally substituted with one to three substituents, each substituent being independently selected from the group consisting of F, Cl, Me, OMe, $CF_3$, $OCF_3$ and $OCF_2H$.

A group of compounds, which is preferred among the "$M^1$ Group" of compounds, designated the "N Group", contains those compounds of the "$M^1$ Group", having the formula I as shown hereinabove, wherein $X^5$ and $X^{5a}$ are each methyl; $R^2$ is methyl, ethyl, or —$CH_2CF_3$; $A^1$ is phenyl optionally substituted with one to three substituents, each substituent being independently selected from the group consisting of F, Cl, Me, OMe, $CF_3$, $OCF_3$ and $OCF_2H$; $R^3$ is phenyl-$CH_2$—O—$CH_2$—, phenyl-$(CH_2)_3$— or thienyl-$CH_2$—O—$CH_2$— where the aryl portion is optionally substituted with one to three substituents, each substituent being independently selected from; the group consisting of F, Cl, Me, OMe, $CF_3$, $OCF_3$ and $OCF_2H$.

Another group of compounds, which is preferred among the "$M^1$ Group" of compounds, designated the "O Group", contains those compounds of the "$M^1$ Group", having the formula I as shown hereinabove, wherein $X^5$ and $X^{5a}$ are each methyl; $R^2$ is methyl, ethyl, or $CH_2CF_3$; $A^1$ is 2-pyridyl or 3-pyridyl optionally substituted with one to two substituents, each substituent being independently selected from the group consisting of F, Cl, Me, OMe, $CF_3$, $OCF_3$ and $OCF_2H$; $R^3$ is phenyl-$CH_2$—O—$CH_2$—, phenyl-$(CH_2)_3$— or thienyl-$CH_2$—O—$CH_2$— where the aryl portion is optionally substituted with one to three substituents, each substituent being independently selected from the group consisting of F, Cl, Me, OMe, $CF_3$, $OCF_3$ and $OCF_2H$.

Another group of compounds, which is preferred among the "$M^1$ Group" of compounds, designated the "P Group", contains those compounds of the "$M^1$ Group", having the formula I as shown hereinabove, wherein $X^5$ and $X^{5a}$ are each methyl; $R^2$ is methyl, ethyl, or $CH_2CF_3$; $A^1$ is phenyl optionally substituted with one to three substituents, each substituent being independently selected from the group consisting of F, Cl, Me, OMe, $CF_3$, $OCF_3$ and $OCF_2H$; $R^3$ is 2-pyridyl-$CH_2$—O—$CH_2$—, or 3-pyridyl-$CH_2$—O—$CH_2$— where the aryl portion is optionally substituted with one to two substituents, each substituent being independently selected from the group consisting of F, Cl, Me, OMe, $CF_3$, $OCF_3$ and $OCF_2H$.

A group of compounds, which is preferred among the "O Group" of compounds, designated the "Q Group", contains those compounds of the "O Group", having the formula

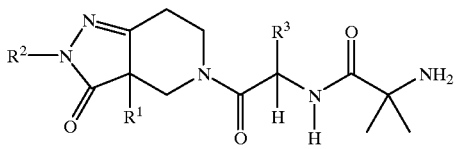

the racemic-diastereomeric mixtures and optical isomers of said compounds wherein $R^2$ is methyl; $A^1$ is 2-pyridyl; and $R^3$ is —$CH_2$—O—$CH_2$-phenyl;

$R^2$ is $CH_2CF_3$; $A^1$ is 2-pyridyl; and $R^3$ is —$CH_2$—O—$CH_2$-3-chloro-phenyl;

$R^2$ is $CH_2CF_3$; $A^1$ is 2-pyridyl; and $R^3$ is —$CH_2$—O—$CH_2$-4-chloro-phenyl;

$R^2$ is $CH_2CF_3$; $A^1$ is 2-pyridyl; and $R^3$ is —$CH_2$—O—$CH_2$-2,4-di-chloro-phenyl;

$R^2$ is $CH_2CF_3$; $A^1$ is 2-pyridyl; and $R^3$ is —$CH_2$—O—$CH_2$-3-chloro-thiophene; or $R^2$ is $CH_2CF_3$; $A^1$ is 2-pyridyl; and $R^3$ is —$CH_2$—O—$CH_2$-2,4-di-fluoro-phenyl.

The diastereomeric mixture of 2-amino-N-[1-(R)-benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(3-chlorbenzyloxy-methyl)-2-oxo-2-[3-oxo-3a-(R,S)-pyridin-2-ylmethyl-2-(2,2,2-trifluoro-ethyl)$_{2,3,3}$a,4,6,7-hexahydro-pyrazolo[4,3-c]pyridin-5-yl]-ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(4-chloro-benzyloxy-methyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide is preferred among the "O Group" of compounds and the separated 3a-(R) and 3a-(S) isomers are preferred of the diastereomeric mixture.

The diastereomeric mixture of 2-amino-N-{1-(R)-(2,4-dichlorobenzyloxymethyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3c]pyridin-5-yl]-ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(4-chloro-thiophen-2-ylmethoxymethyl)-2-oxo-2-[3-oxo-3a-(R,S)-pyridin-2-ylmethyl-2-(2,2,2-trifluoro-ethyl)-2,3,3a,4,5,7-hexahydro-pyrazolo[3,4-c]pyridin-6-yl]-ethyl}-2-methyl-propionamide is preferred among the "Q Group" of compounds and the separated 3a-(R) and 3a-(S) isomers arve preferred of the diastereomeric mixture.

The diastereomefic mixture of 2-amino-N-{1-(R)-(2,4-difluoro-benzyloxy-methyl)-2-oxo-2-[3-oxo-3a-(R,S)-pyridin2-ylmethyl-2-(2,2,2-trifluoro-ethyl)-2,3,3a,4,6,7-hexahydro-pyrazolo[4,3-c]pyridin-5-yl]-ethyl}-2-methyl-propionamide is preferred among the "Q Group" of compounds and the separated 3a-(R) and 3a-(S) isomers are preferred of the diastereomeric mixture.

A group of compounds which contains intermediates useful in synthesizing the compounds of formula (I) are of the formula

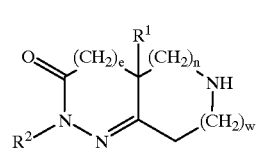

(II)

the racemic-diastereomeric mixtures and optical isomers of said compounds and the pharmaceutically-acceptable salts thereof, wherein e is 0 or 1; n and w are each independently 0, 1 or 2, provided that w and n cannot both be 0 at the same time;

$R^1$ is hydrogen, —CN, —$(CH_2)_q N(X^6)C(O)X^6$, —$(CH_2)_q N(X^6)C(O)(CH_2)_t$—$A^1$, —$(CH_2)_q N(X^6)SO_2(CH_2)_t$—$A^1$, —$(CH_2)_q N(X^6)SO_2 X^6$, —$(CH_2)_q N(X^6)C(O)N(X^6)(CH_2)_t$—$A^1$, —$(CH_2)_q N(X^6)C(O)N(X^6)(X^6)$, —$(CH_2)_q C(O)N(X^6)(X^6)$, —$(CH_2)_q C(O)N(X^6)(CH_2)_t$—$A^1$, —$(CH_2)_q C(O)OX^6$, —$(CH^1)_q C(O)O(CH_2)_t$—$A^1$, —$(CH_2)_q OX^6$, —$(CH_2)_q OC(O)X^6$, —$(CH_2)_q OC(O)(CH_2)_t$—$A^1$, —$(CH_2)_q OC(O)N(X^6)(CH_2)_t$—$A^1$, —$(CH_2)_q OC(O)N(X^6)(X^6)$, —$(CH_2)_q C(O)X^6$, —$(CH_2)_q C(O)(CH_2)_t$—$A^1$, —$(CH_2)_q N(X^6)C(O)OX^6$, —$(CH_2)_q N(X^6)SO_2 N(X^6)(X^6)$, —$(CH_2)_q S(O)_m X^6$, —$(CH_2)_q S(O)_m (CH_2)_t$—$A^1$, —$(C_1–C_{10})$alkyl, —$(CH_2)_t$—$A^1$, —$(CH_2)_q$—$(C_3–C_7)$Cycoalkyl, —$(CH_2)_q$—$Y^1$—$(C_1–C_6)$alkyl, —$(CH_2)_q$—$Y^1$—$(CH_2)_t$—$A^1$ or —$(CH_2)_q$—$Y^1$—$(CH_2)_t$—$(C_3–C_7)$ cycloalkyl;

where the alkyl and cydoalkyl groups in the definition of $R^1$ are optionally substituted with $(C_1–C_4)$alkyl, hydroxyl, ($C_1$–$C_4$)alkoxy, carboxyl, $CONH_2$, —S(O)$_m$($C_1$–$C_6$)alkyl, —$CO_2$($C_1$–$C_4$)alkyl, 1H-tetrazol-5-yl or 1 to 3 fluoro; $Y^1$ is O, S(O)$_m$, —C(O)N$X^6$, —CH=CH—, —C≡C—, —N($X^6$)C(O)—, —C(O)N$X^6$—, —C(O)O—, —OC(O)N($X^6$)— or —OC(O)—; q is 0, 1, 2, 3 or 4; t is 0, 1, 2 or 3;

said $(CH_2)_q$ group and $(CH_2)_t$ group may each be optionally substituted with 1 to 3 fluoro, 1 or 2 ($C_1$–$C_4$)alkyl, hydroxyl, ($C_1$–$C_4$)alkoxy, carboxyl, —$CONH_2$, —S(O)$_m$($C_1$–$C_6$)alkyl, —$CO_2$($C_1$–$C_4$)alkyl ester, or 1H-tetrazol-5-yl;

$R^2$ is hydrogen, ($C_1$–$C_8$)alkyl, —($C_0$–$C_3$)alkyl-($C_3$–$C_8$)cycloalkyl, —($C_1$–$C_4$)alkyl-$A^1$ or $A^1$; where the alkyl groups and the cycloalkyl groups in the definition of $R^2$ are optionally substituted by hydroxyl, —C(O)O$X^6$, —C(O)N($X^6$)($X^6$), —N($X^6$)($X^6$), —S(O)$_m$($C_1$–$C_6$)alkyl, —C(O)$A^1$, —C(O)($X^6$), $CF_3$, CN or 1 to 3 halogen;

$A^1$ for each occurrence is independently ($C_5$–$C_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, or a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —O$X^6$, —C(O)N($X^6$)($X^6$), —C(O)O$X^6$, oxo, ($C_1$–$C_6$)alkyl, nitro, cyano, benzyl, —S(O)$_m$($C_1$–$C_6$)alkyl, 1H-tetrazol-5-yl, phenyl, phenoxy, phenylalkyloxy, halophenyl, methylenedioxy, —N($X^6$)($X^6$), —N($X^6$)C(O)($X^6$), —$SO_2$N($X^6$)($X^6$), —N($X^6$)$SO_2$-phenyl, —N($X^6$)$SO_2X^6$, —CON$X^{11}X^{12}$, —$SO_2NX^{11}X^{12}$, —N$X^6SO_2X^{12}$, —N$X^6CONX^{11}X^2$, —N$X^6SO_2NX^{11}X^{12}$, —N$X^6$C(O)$X^{12}$, imidazolyl, thiazolyl and tetrazolyl, provided that if $A^1$ is optionally substituted with methylenedioxy then it can only be substituted by one methylenedioxy;

where $X^{11}$ is hydrogen or optionally substituted ($C_1$–$C_6$)alkyl;

the optionally substituted ($C_1$–$C_6$)alkyl defined for $X^{11}$ is optionally independently substituted with phenyl, phenoxy, ($C_1$–$C_6$)alkoxycarbonyl, —S(O)$_m$($C_1$–$C_6$)alkyl, 1 to 5 halogens, 1 to 3 hydroxy, 1 to 3 ($C_1$–$C_{10}$)alkanoyloxy or 1 to 3 ($C_1$–$C_6$)alkoxy;

$X^{12}$ is hydrogen, ($C_1$–$C_6$)alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$; or $X^{11}$ and $X^{12}$ are taken together to form —$(CH_2)_r$—$L^1$—$(CH_2)_r$—;

$L^1$ is C($X^2$)($X^2$), O, S(O)$_m$ or N($X^2$);

r for each occurrence is independently 1, 2 or 3;

$X^2$ for each occurrence is independently hydrogen, optionally substituted ($C_1$–$C_6$)alkyl, or optionally substituted ($C_3$–$C_7$)cycloalkyl, where the optionally substituted ($C_1$–$C_6$)alkyl and optionally substituted ($C_3$–$C_7$)cycloalkyl in the definition of $X^2$ are optionally independently substituted with —S(O)$_m$($C_1$–$C_6$)alkyl, —C(O)O $X^3$, 1 to 5 halogens or 1 to 3 O$X^3$;

$X^3$ for each occurrence is independently hydrogen or ($C_1$–$C_6$)alkyl;

$X^6$ for each occurrence is independently hydrogen, optionally substituted ($C_1$–$C_6$)alkyl, ($C_2$–$C_6$) halogenated alkyl, optionally substituted ($C_3$–$C_7$) cycloalkyl, ($C_3$–$C_7$)-halogenatedcycloalkyl, where optionally substituted ($C_1$–$C_6$)alkyl and optionally substituted ($C_3$–$C_7$)cycloalkyl in the definition of $X^6$ is optionally independently substituted by, hydroxyl, ($C_1$–$C_4$)alkoxy, carboxyl, $CONH_2$, —S(O)$_m$($C_1$–$C_6$)alkyl, —$CO_2$($C_1$–$C_4$)alkyl, 1H-tetrazol-5-yl or 1 or 2 ($C_1$–$C_4$)alkyl; or where there are two $X^6$ groups on one atom and both $X^6$ are ($C_1$–$C_6$)alkyl, the two ($C_1$–$C_6$)alkyl groups may be optionally joined and, together with the atom to which the two $X^6$ groups are attached, form a 4- to 9-membered ring optionally having oxygen, sulfur or N$X^7$;

$X^7$ is hydrogen or ($C_1$–$C_6$)alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form C(O)$X^6$, C(O)$X^{12}$, $SO_2X^6$ or $SO_2X^{12}$; and when $R^2$ is hydrogen then $R^1$ is not —CH=CH-phenyl.

A group of intermediate compounds preferred among the foregoing group of formula (II), designated "Group AA", contains those compounds wherein w is 0 or 1; n is 1; $R^1$ is hydrogen, —$(CH_2)_q$—($C_3$–$C_7$)cycloalkyl, —$(CH_2)_r$—$A^1$ or ($C_1$–$C_{10}$)alkyl where the ($C_1$–$C_{10}$)alkyl and ($C_3$–$C_7$) cycloalkyl groups are optionally substituted with 1 to 3 fluoro and $A^1$ in the definition of $R^1$ is optionally substituted with 1 to 3 substituents independently selected from the group consisting of F, Cl, Me, methoxy, $CF_3$, $OCF_3$ and $OCF_2H$; $R^2$ is hydrogen, ($C_1$–$C_8$)alkyl, ($C_0$–$C_3$)alkyl-($C_3$–$C_7$)cycloalkyl, phenyl, or ($C_1$–$C_3$)alkyl-phenyl where the alkyl and phenyl groups are optionally substituted with 1 to 3 substituents independently selected from the group consisting of F, $CF_3$, OH and methoxy.

A group of compounds preferred among the "AA Group" compounds, designated "BB Group", contains those compounds of "AA Group" wherein w is 1; e is 0; $R^1$ is —$CH_2$-pyridyl, —$CH_2$-thiazolyl, or —$CH_2$-phenyl optionally substituted with 1 to 3 substituents independently selected from the group consisting of fluoro and chloro; and $R^2$ is hydrogen, ($C_1$–$C_4$)alkyl or phenyl where the ($C_1$–$C_4$) alkyl or phenyl groups in the definition of $R^2$ is optionally substituted with 1 to 3 substituents independently selected from the group consisting of fluoro, hydroxy or methoxy.

Compounds which are preferred among the "BB Group" compounds is the diastereomeric mixture of a compound wherein $R^1$ is —$CH_2$-phenyl and $R^2$ is methyl or hydrogen; and the separated 3a-(R) and 3a-(S) isomers are preferred of the diastereomeric mixture.

Another group of intermediate compounds which are useful in the synthesis of the compounds of formula (I) have the formula

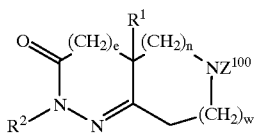

(III)

the racemic-diastereomeric mixtures and optical isomers of said compounds wherein $Z^{100}$ is methyl, BOC, CBZ, $CF_3C(O)$—, FMOC, TROC, trityl, tosyl, $CH_3C(O)$— or optionally substituted benzyl which optionally substituted with methoxy, dimethoxy or nitro; e is 0 or 1; n and w are each independently 0, 1 or 2, provided that w and n cannot both be 0 at the same time;

$R^1$ is hydrogen, —CN, —$(CH_2)_qN(X^6)C(O)X^6$, —$(CH_2)_q N(X^6)C(O)(CH_2)_t$—$A^1$, —$(CH_2)_qN(X)SO_2(CH_2)_t$—$A^1$, —$(CH_2)_qN(X)SO_2X^6$, —$(CH_2)_qN(X^6)C(O)N(X^6)(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)OX^6$, —$(CH_2)_qC(O)O(CH_2)_t$—$A^1$, —$(CH_2)_qOX^6$, —$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_tOC(O)N(X^6)(X^6)$, —$(CH_2)_qC(O)X^6$, —$(CH_2)_qC(O)(CH_2)_t$—$A^1$, —$(CH_2)_qN(X^6)C(O)OX^6$, —$(CH_2)_qN(X^6)SO_2N(X^6)(X^6)$, —$(CH_2)_qS(O)_mX^6$, —$(CH_2)_qS(O)_m(CH_2)_t$—$A^1$, —$(C_1$–$C_{10})$alkyl, —$(CH_2)_t$—$A^1$, —$(CH_2)_q$—$(C_3$–$C_7)$cycloalkyl, —$(CH_2)_q$—$Y^1$—$(C_1$–$C_6)$alkyl, —$(CH_2)_q$—$Y^1$—$(CH_2)_t$—$A^1$ or —$(CH_2)_q$—$Y^1$—$(CH_2)_t$—$(C_3$–$C_7)$cycloalkyl;

where the alkyl and cycloalkyl groups in the definition of $R^1$ are optionally substituted with $(C_1$–$C_4)$alkyl, hydroxyl, $(C_1$–$C_4)$alkoxy, carboxyl, $CONH_2$, —$S(O)_m(C_1$–$C_6)$alkyl, —$CO_2(C_1$–$C_4)$alkyl, 1H-tetrazol-5-yl or 1 to 3 fluoro;

$Y^1$ is O, $S(O)_m$, —$C(O)NX^6$, —CH=CH—, —C≡C—, —$N(X^6)C(O)$, —$C(O)NX^6$, —$C(O)O$, —$OC(O)N(X^6)$ or —$OC(O)$;

q is 0, 1, 2, 3 or 4;

t is 0, 1, 2 or 3;

said $(CH_2)_q$ group and $(CH_2)_t$ group may each be optionally substituted with hydroxyl, $(C_1$–$C_4)$alkoxy, carboxyl, —$CONH_2$, —$S(O)_m(C_1$–$C_6)$alkyl, —$CO_2(C_1$–$C_4)$alkyl, 1H-tetrazol-5-yl, 1 to 3 fluoro or 1 or 2 $(C_1$–$C_4)$alkyl;

$R^2$ is hydrogen, $(C_1$–$C_8)$alkyl, —$(C_0$–$C_3)$alkyl-$(C_3$–$C_8)$cycloalkyl, —$(C_1$–$C_4)$alkyl-$A^1$ or $A^1$; where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1$–$C_6)$alkyl, —$C(O)A^1$, —$C(O)(X^6)$, $CF_3$, CN or 1 to 3 halogen;

$A^1$ for each occurrence is independently $(C_5$–$C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, or a bicyclic ring system consisting of a partially saturated, fully unsaturated or fully saturated 5- or 6-membered ring, optionally having 1 to 4 heteroatoms Independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1$–$C_6)$alkyl, nitro, cyano, benzyl, —$S(O)_m(C_1$–$C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$SO_2N(X^6)(X^6)$, —$N(X^6)SO_2$-phenyl, —$N(X^6)SO_2X^6$, —$CONX^{11}X^{12}$, —$SO_2NX^{11}X^{12}$, —$NX^6SO_2X^{12}$, —$NX^6CONX^{11}X^{12}$, —$NX^6SO_2NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1$–$C_6)$alkyl;

the optionally substituted $(C_1$–$C_6)$alkyl defined for $X^{11}$ is optionally independently substituted with phenyl, phenoxy, $(C_1$–$C_6)$alkoxycarbonyl, —$S(O)_m(C_1$–$C_6)$alkyl, 1 to 5 halogens, 1 to 3 hydroxy, 1 to 3 $(C_1$–$C_{10})$alkanoyloxy or 1 to 3 $(C_1$–$C)$alkoxy;

$X^{12}$ is hydrogen, $(C_1$–$C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$; or $X^{11}$ and $X^{12}$ are taken together to form —$(CH_2)_r$—$L^1$—$(CH_2)_r$—;

$L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1$–$C_6)$alkyl, or optionally substituted $(C_3$–$C_7)$cycloalkyl, where the optionally substituted $(C_1$–$C_6)$alkyl and optionally substituted $(C_3$–$C_7)$cycloalkyl in the definition of $X^2$ are optionally independently substituted with —$S(O)_m(C_1$–$C_6)$alkyl, —$C(O)OX^3$, 1 to 5 halogens or 1 to 3 $OX^3$;

$X^3$ for each occurrence is independently hydrogen or $(C_1$–$C_6)$alkyl;

$X^6$ for each occurrence is independently hydrogen, optionally substituted $(C_1$–$C_6)$alkyl, $(C_2$–$C_6)$ halogenated alkyl, optionally substituted $(C_3$–$C_7)$ cycloalkyl, $(C_3$–$C_7)$-halogenated cydoalkyl, where optionally substituted $(C_1$–$C_6)$alkyl and optionally substituted $(C_3$–$C_7)$cycloalkyl in the definition of $X^6$ is optionally independently substituted with hydroxyl, $(C_1$–$C_4)$alkoxy, carboxyl, $CONH_2$, —$S(O)_m(C_1$–$C_6)$alkyl, —$CO_2(C_1$–$C_4)$alkyl, 1H-tetrazol-5-yl or 1 or 2 $(C_1$–$C_4)$alkyl; or where there are two $X^6$ groups on one atom and both $X^6$ are $(C_1$–$C_6)$alkyl, the two $(C_1$–$C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1$–$C_6)$alkyl optionally substituted with hydroxyl; and m for each occurrence is independently 0, 1 or 2;

with the proviso that:

$X^6$ and $X^{12}$ cannot be hydrogen when it is attached to $C(O)$ or $SO_2$ in the form $C(O)X^6_1$, $C(O)X^{12}$, $SO_2X^6$ or $SO_2X^{12}$;

when R² is hydrogen then R¹ is not —CH=CH-phenyl;
when R² is H and R¹ is —CH₂—CH=CH—Ph, then $Z^{100}$ is not BOC;
when R² is H and R¹ is then $Z^{100}$ is not BOC;
when R² is H and R¹ is —CH₂—C(CH₃)=CH₂, then $Z^{100}$ is not BOC; and
when R² is phenyl and R¹ is —CH₃, then $Z^{100}$ is not CH₃C(O)—.

A group of compounds preferred among the foregoing group of compounds of formula (III), designated "CC Group", are those compounds wherein w is 0 or 1; n is 1; $Z^{100}$ is BOC, methyl, benzyl or CBZ;
R¹ is hydrogen, —(CH₂)$_q$—(C₃-C₇)cycloalkyl, —(CH₂)$_t$—A¹ or (C₁-C₁₀)alkyl where the (C₁-C₁₀)alkyl and (C₃-C₇)cycloalkyl groups are optionally substituted with 1 to 3 fluoro and A¹ in the definition of R¹ is optionally substituted with 1 to 3 substituents independently selected from the group consisting of F, Cl, Me, OMe, CF₃, OCF₃ and OCF₂H;
R² is hydrogen, (C₁-C₈)alkyl, —(C₀-C₃)alkyl-(C₃-C₇)cycloalkyl, phenyl, or —(C₁-C₃)alkylphenyl where the alkyl and phenyl groups are optionally substituted with 1 to 3 substituents independently selected from the group consisting of F, CF₃, OH and OMe.

A group of compounds preferred among the "CC Group" compounds, designated "DD Group", contains those compounds of "CC Group" wherein $Z^{100}$ is BOC; w is 1; e is 0; R¹ is —CH₂-pyridyl, —CH₂-thiazolyl, or —CH₂-phenyl optionally substituted with 1 to 3 substituents independently selected from the group consisting of fluoro and chloro; and R² is hydrogen, (C₁-C₄)alkyl or phenyl where the (C₁-C₄) alkyl or phenyl groups in the definition of R² is optionally substituted with 1 to 3 substituents independently selected from the group consisting of fluoro, hydroxy and methoxy.

Compounds which are preferred among the "DD Group" compounds is the diastereomeric mixture of a compound wherein R¹ is —CH₂-phenyl and R² is methyl or hydrogen; and the separated 3a-(R) and 3a-(S) isomers are preferred of the diastereomeric mixture.

Yet another group of compounds which are useful in the synthesis of the compounds of formula (I) contains those compounds of the formula

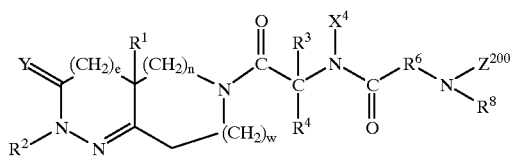

(IV)

the racemic-diastereomeric mixtures and optical isomers of said compounds wherein $Z^{200}$ is t-BOC, CBZ, CF₃C(O)—, FMOC, TROC, trityl, tosyl or optionally substituted benzyl which is optionally substituted with methoxy, dimethoxy or nitro;
e is 0 or 1;
n and w are each independently 0, 1 or 2, provided that w and n cannot both be 0 at the same time;
Y is oxygen or sulfur;
R¹ is hydrogen, —CN, —(CH₂)$_q$N(X⁶)C(O)X⁶, —(CH₂)$_q$N(X⁶)C(O)(CH₂)$_t$—A¹, —(CH₂)$_q$N(X⁶)SO₂(CH₂)$_t$—A¹, —(CH₂)$_q$N(X⁶)SO₂X⁶, —(CH₂)$_q$N(X⁶)C(O)N(X⁶)(CH₂)$_t$—A¹, —(CH₂)$_q$N(X⁶)C(O)N(X⁶)(X⁶), —(CH₂)$_q$C(O)N(X⁶)(X⁶), —(CH₂)$_q$C(O)N(X⁶)(CH₂)$_t$—A¹, —(CH₂)$_q$C(O)OX⁶, —(CH₂)$_q$C(O)O(CH₂)$_t$—A¹, —(CH₂)$_q$OX⁶, —(CH₂)$_q$OC(O)X⁶, —(CH₂)$_q$OC(O)(CH₂)$_t$—A¹, —(CH₂)$_q$OC(O)N(X⁶)(CH₂)$_t$—A¹, —(CH₂)$_q$OC(O)N(X⁶)(X⁶), —(CH₂)$_q$C(O)X⁶, —(CH₂)$_q$C(O)(CH₂)$_t$—A¹¹, —(CH₂)$_q$N(X⁶)C(O)OX⁶, —(CH₂)$_q$N(X⁶)SO₂N((X⁶)(X⁶), —(CH₂)$_q$S(O)$_m$X⁶, —(CH₂)$_q$S(O)$_m$(CH₂)$_t$—A¹, —(C₁-C₁₀)alkyl, —(CH₂)$_t$—A¹, —(CH₂)$_q$—(C₃-C₇)cycloalkyl, —(CH₂)$_q$—Y¹—(C₁-C₆)alkyl, —(CH₂)$_q$—Y¹—(CH₂)$_t$—A¹ or —(CH₂)$_q$—Y¹—(CH₂)$_t$—(C₃-C₇)cycloalkyl;
where the alkyl and cycloalkyl groups in the definition of R¹ are optionally substituted with (C₁-C₄)alkyl, hydroxyl, (C₁-C₄)alkoxy, carboxyl, CONH₂, —S(O)$_m$(C₁-C₆)alkyl, —CO₂(C₁-C₄)alkyl ester, 1H-tetrazol-5-yl or 1 to 3 fluoro;
Y¹ is O, S(O)$_m$, —C(O)NX⁶, —CH=CH—, —C≡C—, —N(X⁶)C(O), —C(O)NX⁶, —C(O)O, —OC(O)N(X⁶) or —OC(O);
q is 0, 1, 2, 3 or 4;
t is 0, 1, 2 or 3;
said (CH₂)$_q$ group and (CH₂)$_t$ group may each be optionally substituted with hydroxyl, (C₁-C₄)alkoxy, carboxyl, —CONH₂, —S(O)$_m$(C₁-C₆)alkyl, —CO₂(C₁-C₄)alkyl, 1H-tetrazol-5-yl, 1 to 3 fluoro or 1 or 2 (C₁-C₄)alkyl;
R² is hydrogen, (C₁-C₈)alkyl, —(C₀-C₃)alkyl-(C₃-C₈)cycloalkyl, —(C₁-C₄)alkyl-A¹ or A¹; where the alkyl groups and the cycloalkyl groups in the definition of R² are optionally substituted with hydroxyl, —C(O)OX⁶, —C(O)N(X⁶)(X⁶), —N(X⁶)(X⁶), —S(O)$_m$(C₁-C₆) alkyl, —C(O)A¹, —C(O)(X⁶), CF₃, CN or 1 to 3 halogen;
R³ is A¹, (C₁-C₁₀)alkyl, —(C₁-C₆)alkyl-A¹, —(C₁-C₆)alkyl-(C₃-C₇)cycloalkyl, —(C₁-C₅)alkyl-X¹—(C₁-C₅)alkyl, —(C₁-C₅)alkyl-X¹—(C₀-C₅)alkyl-A¹ or —(C₁-C₅)alkyl-X¹—(C₁-C₅)alkyl-(C₃-C₇)cycloalkyl;
where the alkyl groups in the definition of R³ is optionally substituted with —S(O)$_m$(C₁-C₆)alkyl, —C(O)OX³, 1 to 5 halogens or 1 to 3 OX³; X¹ is O, S(O)$_m$, —N(X²)C(O)—, —C(O)N(X²)—, —OC(O)—, —C(O)O—, —CX²=CX²—, —N(X²)C(O)O—, —OC(O)N(X²)— or —C≡C—;
R⁴ is hydrogen, (C₁-C₆)alkyl or (C₃-C₇)cycloalkyl, or R⁴ is taken together with R³ and the carbon atom to which they are attached and form (C₅-C₇)cycloalkyl, (C₅-C₇) cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
X⁴ is hydrogen or (C₁-C₆)alkyl or X⁴ is taken together with R⁴ and the nitrogen atom to which X⁴ is attached and the carbon atom to which R⁴ is attached and form a five to seven membered ring;

$R^8$ is a bond or is

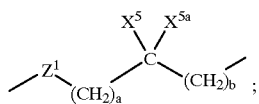

where a and b are independently 0, 1, 2 or 3;
$X^5$ and $X^{5a}$ are each independently selected from the group consisting of hydrogen, trifluoromethyl, $A^1$ and optionally substituted $(C_1-C_6)$alkyl;
the optionally substituted $(C_1-C_6)$alkyl in the definition of $X^5$ and $X^{5a}$ is optionally substituted with a substituent selected from the group consisting of $A^1$, $-OX^2$, $-S(O)_m(C_1-C_6)$alkyl, $-C(O)OX^2$, $(C_3-C_7)$cycloalkyl, $-N(X^2)(X^2)$ and $-C(O)N(X^2)(X^2)$;
or the carbon bearing $X^5$ and $X^{5a}$ forms an alkylene bridge with the nitrogen atom bearing $Z^{200}$ and $R^8$ where the alkylene bridge contains 1 to 5 carbon atoms provided that $X^5$ or $X^{5a}$ but not both may be on the carbon atom and $Z^{200}$ or $R^8$ but not both may be on the nitrogen atom;
or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;
or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
$Z^1$ is a bond, O or $N-X^2$, provided that when a and b are both 0 then $Z^1$ is not $N-X^2$ or O;
$R^8$ is hydrogen or optionally substituted $(C_1-C_6)$alkyl;
where the optionally substituted $(C_1-C_6)$alkyl in the definition of $R^8$ is optionally independently substituted with $A^1$, $-C(O)O-(C_1-C_6)$alkyl, $-S(O)_m(C_1-C_6)$alkyl, 1 to 5 halogens, 1 to 3 hydroxy, 1 to 3 $-O-C(O)(C_1-C_{10})$alkyl or 1 to 3 $(C_1-C_6)$alkoxy; or
$A^1$ for each occurrence is independently $(C_5-C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, or a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $-OX^6$, $-C(O)N(X^6)(X^6)$, $-C(O)OX^6$, oxo, $(C_1-C_6)$alkyl, nitro, cyano, benzyl, $-S(O)_m(C_1-C)$alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-SO_2N(X^6)(X^6)$, $-N(X^6)SO_2$-phenyl, $-N(X^6)SO_2X^6$, $-CONX^{11}X^{12}$, $-SO_2NX^{11}X^{12}$, $-NX^6SO_2X^{12}$, $-NX^6CONX^{11}X^{12}$, $-NX^6SO_2NX^{11}X^{12}$, $-NX^6C(O)X^{12}$, imidazolyl, thiazolyl and tetrazolyl, provided that if $A^1$ is optionally substituted with methylenedioxy then it can only be substituted with one methylenedioxy;
where $X^{11}$ is hydrogen or optionally substituted $(C_1-C_6)$alkyl;
the optionally substituted $(C_1-C_6)$alkyl defined for $X^{11}$ is optionally independently substituted with phenyl, phenoxy, $(C_1-C_6)$alkoxycarbonyl, $-S(O)_m(C_1-C_6)$alkyl, 1 to 5 halogens, 1 to 3 hydroxy, 1 to 3 $(C_1-C_{10})$alkanoyloxy or 1 to 3 $(C_1-C_6)$alkoxy;
$X^{12}$ is hydrogen, $(C_1-C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$; or $X^{11}$ and $X^{12}$ are taken together to form $-(CH_2)_r-L^1-(CH_2)_r-$;
$L^1$ is $C(X^2)(X^2)$, O, $S(O)_m$ or $N(X^2)$;
r for each occurrence is independently 1, 2 or 3;
$X^2$ for each occurrence is independently hydrogen, optionally substituted $(C_1-C_6)$alkyl, or optionally substituted $(C_{3-7})$cycloalkyl, where the optionally substituted $(C_1-C_6)$alkyl and optionally substituted $(C_3-C_7)$ cycloalkyl in the definition of $X^2$ are optionally independently substituted with $-S(O)_m(C_1-C_6)$alkyl, $-C(O)OX^3$, 1 to 5 halogens or 1 to 3 $-OX^3$;
$X^3$ for each occurrence is independently hydrogen or $(C_1-C_6)$alkyl;
$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenatedcycloalkyl, where optionally substituted $(C_1-C_6)$alkyl and optionally substituted $(C_3-C_7)$cycloalkyl in the definition of $X^6$ is optionally independently substituted with hydroxyl, $(C_1-C_4)$alkoxy, carboxyl, $CONH_2$, $-S(O)_m(C_1-C_6)$ alkyl, $-CO_2(C_1-C_4)$alkyl, 1H-tetrazol-5-yl or 1 or 2 $(C_1-C_4)$alkyl; or
when there are two $X^6$ groups on one atom and both $X^6$ are $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;
$X^7$ is hydrogen or $(C_1-C_6)$alkyl optionally substituted by hydroxyl; and m for each occurrence is independently 0, 1 or 2;
with the proviso that:
$X^6$ and $X^{12}$ cannot be hydrogen when it is attached to $C(O)$ or $SO_2$ in the form $C(O)X^6$, $C(O)X^{12}$, $SO_2X^6$ or $SO_2X^{12}$; and
when $R^6$ is a bond then L is $N(X^2)$ and each r in the definition $-(CH_2)_r-L-(CH_2)_r-$ is 2 or 3.
Compounds which are preferred of the foregoing compounds of formula (IV) is the compound wherein e is 0; Y is O; $R^1$ is —$CH_2$-phenyl; $R^2$ is methyl or hydrogen; n is 1; w is 1; $R^3$ is —$CH_2$—O—$CH_2$-phenyl; $R^4$ is hydrogen; $X^4$ is hydrogen; $R^6$ is —$C(CH_3)_2$—; $Z^{200}$ is BOC and $R^8$ is hydrogen.

This invention also provides:

- a method for increasing levels of endogenous growth hormone in a human or other animal which comprises administering to such human or other animal an effective amount of a compound of Formula I;
- a pharmaceutical composition useful for increasing the endogenous production or release of growth hormone in a human or other animal which comprises an inert carrier and an effective amount of a compound of Formula I;
- a pharmaceutical composition useful for increasing the endogenous production or release of growth hormone in a human or other animal which comprises an inert carrier, an effective amount of a compound of Formula I and another growth hormone secretagogue such as, GHRP-6, Hexarelin, GHRP-1, IGF-1, IGF-2, B-HT920 or growth hormone releasing factor (GRF) or an analog thereof;
- a method for the treatment or prevention of osteoporosis which comprises administering to a human or other animal in need of such treatment or prevention an amount of a compound of Formula I which is effective in treating or preventing osteoporosis;
- a method for the treatment or prevention of osteoporosis which comprises administering to a human or other animal with osteoporosis a combination of a bisphosphonate compound such as alendronate, and especially preferred is the bisphosphonate compound ibandronate, and a compound of Formula I;
- a method for the treatment or prevention of osteoporosis which comprises administering to a human or other animal with osteoporosis a combination of estrogen or Premarin® and a compound of Formula I and optionally progesterone;
- a method to increase IGF-1 levels in IGF-1 deficient humans or other animals which comprises administering to a human or other animal with IGF-1 deficiency a compound of Formula I;
- a method for the treatment of osteoporosis which comprises administering to a human or other animal with osteoporosis a combination of an estrogen agonist or antagonist such as tamoxifen, droloxifene, raloxifene and idoxifene and a compound of Formula I;
- a particularly preferred method for the treatment of osteoporosis comprises administering to a human or other animal with osteoporosis a combination of an estrogen agonist or antagonist such as Cis-6-(4-fluorophenyl)-5-[4-(2-piperidin-1-yl-ethoxy)-phenyl]-5,6,7,8-tetrahydro-naphthalene-2-ol;
  (−)-cis-6-phenyl-5-[4-(2-pyrrolidin-1-yl-ethoxy)phenyl]-5,6,7,8-tetrahydronaphthalene-2-ol;
  cis-6-phenyl-5-[4-(2-pyrrolidin-1-yl-ethoxy)-phenyl]-5,6,7,8-tetrahydronaphthalene-2-ol;
  cis-1-[6'-pyrrolodinoethoxy-3'-pyrdyl]-2-phenyl-6-hydroxy-1,2,3,4-tetrahydronaphthalene;
  1-(4'-pyrrolidinoethoxyphenyl)-2-(4"-fluorophenyl)-6-hydroxy-1,2,3,4-tetrehydroisoquinoline;
  cis-6-(4-hydroxyphenyl)-5-[4-(2-piperidin-1-yl-ethoxy)-phenyl]-5,6,7,8-tetrahydronaphthalene-2-ol; or
  1-(4'-pyrrolidinolethoxyphenyl)-2-phenyl-6-hydroxy-1,2,3,4-tetrahydroisoquinoline and a compound of Formula I;
- a method for the treatment of osteoporosis which comprises administering to a human or other animal with osteoporosis a combination of calcitonin and a compound of Formula I;
- a method for increasing muscle mass, which method comprises administering to a human or other animal in need of such treatment an amount of a compound of Formula I which is effective in promoting release of endogenous growth hormone; and
- a method for promoting growth in growth hormone deficient children which comprises administering to a growth hormone deficient child a compound of Formula I which is effective in promoting release of endogenous growth hormone.

This invention further provides a method for treating or preventing diseases or conditions which may be treated or prevented by growth hormone which comprises administering to a human or other animal in need of such treatment or prevention an amount of a compound of Formula I which is effective in promoting release of endogenous growth hormone.

In another aspect, this invention provides methods for treating or preventing congestive heart failure, frailty associated with aging, and obesity which comprise administering to a human or other animal in need of such treatment or prevention an amount of a compound of Formula I which is effective in promoting release of endogenous growth hormone; of the instant method it is preferred that the disease or condition to be treated or prevented is congestive heart failure or frailty associated with aging.

In another aspect, this invention provides methods for accelerating bone fracture repair, attenuating protein catabolic response after a major operation, reducing cachexia and protein loss due to chronic illness such as AIDS and cancer, accelerating wound healing, and accelerating the recovery of bum patients or patients having undergone major surgery, which comprise administering to a human or other animal in need of such treatment an amount of a compound of Formula I which is effective in promoting release of endogenous growth hormone; of the instant method a preferred method of use is to accelerate bone fracture repair or for accelerating the recovery of patients having undergone major surgery.

In yet another aspect, this invention provides methods for improving muscle strength, mobility, maintenance of skin thickness, metabolic homeostasis and renal homeostasis, which comprise administering to a human or other animal in need of such treatment an amount of a compound of claim 1 which is effective in promoting release of endogenous growth hormone.

The instant compounds promote the release of growth hormone which are stable under various physiological conditions and may be administered parenterally, nasally or by the oral route.

DETAILED DESCRIPTION OF THE INVENTION

One of ordinary skill will recognize that certain substituents listed in this invention may have reduced chemical stability when combined with one another or with heteroatoms in the compounds. Such compounds with reduced chemical stability are not preferred.

In general the compounds of Formula I can be made by processes which include processes known in the chemical arts for the production of compounds. Certain processes for the manufacture of Formula I compounds are provided as further features of the invention and are illustrated by the following reaction schemes.

In the above structural formulae and throughout the instant application, the following terms have the indicated meanings unless expressly stated otherwise:

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by one or more halogen atoms as defined hereinabove.

The term "aryl" is intended to include phenyl and naphthyl and aromatic 5- and 6-membered rings with 1 to 4 heteroatoms or fused 5- or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

The expression "prodrug" refers to compounds that are drug precursors, which following administration, release the drug in vivo via some chemical or physiological process (e.g., a prodrug on being brought to the physiological pH is converted to the desired drug form). Exemplery prodrugs upon cleavage release the corresponding free acid, and such hydrolyzable ester-forming residues of the compounds of this invention include but are not limited to carboxylic acid substituents (e.g., $R^1$ is —$(CH_2)_qC(O)_2X^6$ where $X^6$ is hydrogen, or $R^2$ or $A^1$ contains carboxylic acid) wherein the free hydrogen is replaced by $(C_{1-4})$alkyl, $(C_2-C_{12})$ alkanoyloxymethyl, $(C_4-C_9)$1-(alkanoyloxy)ethyl, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methy-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$-alkylcarbamoyl-$(C_1-C_2)$alkyl and piperidino-, pyrrolidino- or morpholino$(C_2-C_3)$alkyl.

Other exemplary prodrugs release an alcohol of Formula I wherein the free hydrogen of the hydroxyl substituent (e.g., $R^1$ contains hydroxyl) is replaced by $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N-($C_1-C_6$)alkoxycarbonylaminomethyl, succinoyl, $(C_1-C_6)$alkanoyl, α-amino$(C_1-C_4)$alkanoyl, arylacetyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

Prodrugs of this invention where a carboxyl group in a carboxylic acid of Formula (I) is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Certain of the above defined terms may occur more than once in the above formula and upon such occurrence each term shall be defined independently of the other.

Throughout the specification and appendent claims the following abbreviations are used with the following meanings:

| | |
|---|---|
| BOC | t-butyloxycarbonyl |
| BOP | Benzotriazol-1-yloxytris(dimethylamino)phosphonium hexafluorophosphate |
| CBZ | Benzyloxycarbonyl |
| CDI | N,N'-Carbonyldiimidazole |
| $CH_2Cl_2$ | Methylene chloride |
| $CHCl_3$ | Chloroform |
| DCC | Dicyclohexylcarbodiimide |
| DMF | Dimethylformamide |
| EDC | 1-(3-dimethylaminopropyl)-3-ethylcarbodiimide hydrochloride |
| EtOAc | Ethyl acetate |

| | |
|---|---|
| FMOC | 9-Fluorenylmethoxycarbonyl |
| h | hours |
| Hex | Hexane |
| HOAT | 1-Hydroxy-7-azabenzotriazole |
| HOBT | Hydroxybenzotriazole hydrate |
| HPLC | High pressure liquid chromatography |
| MHz | Megahertz |
| MS | Mass Spectrum |
| NMR | Nuclear Magnetic Resonance |
| PTH | Parathyroid hormone |
| TFA | Trifluoroacetic acid |
| THF | Tetrahydrofuran |
| TLC | Thin layer chromatography |
| TRH | Thyrotropin releasing hormone |
| TROC | 2,2,2-Trichloroethoxycarbonyl |

The compounds of the instant invention all have at least one asymmetric center as noted by the asterisk in the structural Formula I, above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and thus more preferred isomer is shown in Formula IA. This preferred absolute configuration also applies to Formula I.

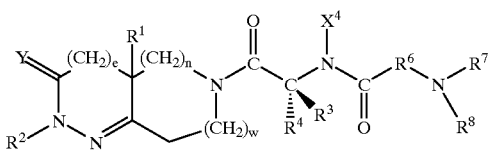

(IA)

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The instant compounds are generally isolated in the form of their pharmaceutically acceptable acid addition salts, such as the salts derived from using inorganic and organic adds. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula (I) and contacting it with about 1 equivalent of the appropriate corresponding acid of the salt which is desired. Work-up and isolation of the resulting salt is well-known to those of ordinary skill in the art.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release.

The compounds of Formula I can be administered to animals, including humans, to release growth hormone in vivo. The compounds are useful for treatment of symptoms related to GH deficiency; stimulate growth or enhance feed efficiency of animals raised for meat production to improve carcass quality; to increase milk production in dairy cattle; improvement of bone or wound healing and improvement in vital organ function. The compounds of the present invention by inducing endogenous GH secretion will alter body composition and modify other GH-dependent metabolic, immunologic or developmental processes. For example, the compounds of the present invention can be given to chickens, turkeys, livestock animals (such as sheep, pigs, horses, cattle, etc.), companion animals (e.g., dogs) or may have utility in aquaculture to accelerate growth and improve the protein/fat ratio. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutically acceptable carrier. Optionally, the pharmaceutical compositions can further comprise an anabolic agent in addition to at least one of the compounds of Formula I or another compound which exhibits a different activity, e.g., an antibiotic growth permittant or an agent to treat osteoporosis or with other pharmaceutically active materials wherein the combination enhances efficacy and minimizes side effects.

Growth promoting and anabolic agents include, but are not limited to, TRH, PTH, diethylstilbesterol, estrogens, β-agonists, theophylline, anabolic steroids, enkephalins, E series prostaglandins, compounds disclosed in U.S. Pat. No. 3,239,345, the disclosure of which is hereby incorporated by reference, e.g., zeranol; compounds disclosed in U.S. Pat. No. 4,036,979, the disclosure of which is hereby incorporated by reference, e.g., sulbenox; and peptides disclosed in U.S. Pat. No. 4,411,890, the disclosure of which is hereby incorporated by reference.

The growth hormone secretagogues of this invention in combination with other growth hormone secretagogues such as the growth hormone releasing peptides GHRP-6 and GHRP-1 as described in U.S. Pat. No. 4,411,890, the disclosure of which is hereby incorporated by reference, and publications WO 89/07110, WO 89/07111 and B-HT920 as well as hexarelin and the newly discovered GHRP-2 as described in WO 93104081 or growth hormone releasing hormone (GHRH, also designated GRF) and its analogs or growth hormone and its analogs or somatomedins including IGF-1 and IGF-2 or μ-adrenergic agonists such as clonidine or serotonin 5HTID agonists such as sumitriptan or agents which inhibit somatostatin or its release such as physostigmine and pyridostigmine, are useful for increasing the endogenous levels of GH in mammals. The combination of a GH secretagogue of this invention with GRF resufts in synergistic increases of endogenous growth hormone.

As is well known to those skilled in the art, the known and potential uses of growth hormone are varied and muflitudinous [See "Human Growth Hormone", Strobel and Thomas, Pharmacological Reviews, 4, pg. 1–34 (1994); T. Rosen et al., Horm Res, 1995; 43: pp. 93–99; M. Degerblad et al., European Journal of Endocrinology, 1995, 133: pp.180–188; J. O. Jorgensen, European Journal of Endocrinology, 1994, 130: pp. 224–228; K. C. Copeland et al., Journal of Clinical Endocrinology and Metabolism, Vol. 78 No. 5, pp. 1040–1047; J. A. Aloi et al., Journal of Clinical Endocrinology and Metabolism, Vol. 79 No. 4, pp. 943–949; F. Cordido et al., Metab. Clin. Exp., (1995), 44(6), pp. 745–748; K. M. Fairhall et al., J. Endocrinol., (1995), 145(3), pp. 417–426; R M. Frieboes et al., Neuroendocrinology, (1995), 61(5), pp. 584–589; and M. Llovera et al., Int. J. Cancer, (1995), 61(1), pp. 138–141]. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adufts: preventing catabolic side effects of glucocorticoids, treating osteoporosis, stimulating the immune system, acceleration of wound healing, accelerating bone fracture repair, treating growth retardation, treating congestive heart failure as disclosed in PCT publications WO 95128173 and WO 95/28174 (an example of a method for assaying growth hormone secretagogues for efficacy in treating congestive heart failure is disclosed in R. Yang et al., Circulation, Vol. 92, No. 2, p.262, 1995), treating acute or chronic renal failure or insufficiency, treatment of physiological short stature, including growth hormone deficient children, treating short stature associated with chronic illness, treating obesity, treating growth retardation associated with Prader-Willi syndrome and Tumer's syndrome; accelerating the recovery and reducing hospitalization of bum patients or following major surgery such as gastrointestinal surgery; treating intrauterine growth retardation, skeletal dysplasia, hypercortisonism and Cushings syndrome; replacing growth hormone in stressed patients; treating osteochondrodysplasias, Noonans syndrome, sleep disorders, Alzheimer's disease, delayed wound healing, and psychosocial deprivation; treating of pulmonary dysfunction and ventilator dependency; attenuating protein catabolic response after a major operation; treating malabsorption syndromes, reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers: stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal hemeostasis in the frail elderly; stimulating osteoblasts, bone remodelling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; stimulating the immune system in companion animals and treating disorders of aging in companion animals; growth promotant in livestock; and stimulating wool growth in sheep.

It will be known to those skilled in the art that there are numerous compounds now being used in an effort to treat the diseases or therapeutic indications enumerated above. Combinations of these therapeutic agents, some of which have also been mentioned above, with the growth promotant, exhibit anabolic and desirable properties of these various therapeutic agents. In these combinations, the therapeutic agents and the growth hormone secretagogues of this invention may be independently and sequentially administered or co-administered in dose ranges from one one-hundredth to one times the dose levels which are effective when these compounds and secretagogues are used singly. Combined therapy to inhibit bone resorption, prevent osteoporosis, reduce skeletal fracture, enhance the healing of bone fractures, stimulate bone formation and increase bone mineral density can be effectuated by combinations of bisphosphonates and the growth hormone secretagogues of this invention, see PCT publication WO 95/11029 for a discussion of combination therapy using bisphosphonates and GH secretagogues. The use of bisphosphonates for these utilities has been reviewed, for example, by Hamdy, N. A. T., Role of Bisphosphonates in Metabolic Bone Diseases, Trends In Endocrinol. Metab., 1993, 4, pages 19–25. Bisphosphonates with these utilities include but are not limited to alendronate, tiludronate, dimethyl-APD, risedronate, etidronate, YM-175, clodronate, pamidronate, and BM-210995 (ibandronate). According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods (see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other estrogen agonists/antagonists will be known to those skilled in the art. A preferred estrogen agonist/antagonist is droloxifene: (phenol, 3-[1-[4[2-(dimethylamino)ethoxy]-phenyl]-2-phenyl-1-butenyl]-, (E)-) and associated compounds which are disclosed in U.S. Pat. No. 5,047,431 (the disclosure of which is hereby incorporated by reference).

Another preferred estrogen agonistantagonist is tamoxifen: (ethanamine,2-[-4-(1,2-diphenyl-1-butenyl)phenoxy]-

N,N-dimethyl, (Z)-2-, 2-hydroxy-1,2,3-propanetricarboxylate (1:1)) and associated compounds which are disclosed in U.S. Pat. No. 4,536,516 (the disclosure of which is hereby incorporated by reference). Another related compound is 4-hydroxy tamoxifen which is disclosed in U.S. Pat. No. 4,623,660 (the disclosure of which is hereby incorporated by reference).

Another preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl]-hydrochloride) and associated compounds which are disclosed in U.S. Pat. No. 4,418,068 (the disclosure of which is hereby incorporated by reference).

Another preferred estrogen agonist/antagonist is idoxifone: Pyrrolidine, 1-[-[4-[[1-(4-iodophenyl)-2-phenyl-1-Butenyl]phenoxy]ethyl] and associated compounds which are disclosed in U.S. Pat. No. 4,839,155 (the disclosure of which is hereby incorporated by reference).

Other preferred estrogen agonist/antagonists include compounds as described in commonly assigned U.S. Pat. No. 5,552,412 the disclosure of which is hereby incorporated by reference. Especially preferred compounds which are described therein are:

cis-6-(4-fluoro-phenyl)-5-[4-(2-piperidin-1-yl-ethoxy)-phenyl]-5,6,7,8-tetrahydronaphthalene-2-ol;

(-)-cis-6-phenyl-5-[4-(2-pyrrolidin-1-yl-ethoxy)-phenyl]-5,6,7,8-tetrahydronaphthalene-2-ol;

cis-6-phenyl-5-[4-(2-pyrrolidin-1-yl-ethoxy)-phenyl]-5,6,7,8-tetrahydronaphthalene-2-ol;

cis-1-[6'-pyrrolodinoethoxy-3'-pyridyl]-2-phenyl6-hydroxy-1,2,3,4-tetrahydronaphthalene;

1-(4'-pyrrolidinoethoxyphenyl)2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl-]5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is hereby incorporated by reference). U.S. Pat. No. 4.133,814 discloses derivatives of 2-phenyl-3-aroyl-benzothiophene and 2-phenyl-3-aroylbenzothiophene-1-oxide.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as those referenced above.

In general an efective dosage for the activities of this invention, for example the treatment of osteoporosis, for the estrogen agonists/antagonists (when used in combination with a compound of Formula I of this invention) is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for
cis-6-(4-fluoro-phenyl)-5-[4-(2-piperidin-1-yl-ethoxy)-phenyl]-5,6,7,8-tetrahydronaphthalene-2-ol;

(−)cis-6-phenyl-5-[4-(2-pyrrolidin-1-yl-ethoxy)-phenyl]-5,6,7,8-tetrahydronaphthalene-2-ol;

cis-6-phenyl-5-[4-(2-pyrrolidin-1-yl-ethoxy)-phenyl]-5,6,7,8-tetrahydronaphthalene2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydronaphthalene-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced saft solution without calcium or magnesium (HBSS). Tissues are finely minced, then subjected to two cycles of mechanically assisted enzymatic dispersion using 10 U/mL bacterial protease (EC 3.4.24.4, Sigma P-6141) in HBSS. The tissue-enzyme mixture is stirred in a spinner flask at 30 rpm in a 5% $CO_2$ atmosphere at about 37° C. for about 30 min, with manual trituration after about 15 min and about 30 min using a 10-mL pipet. This mixture is centrifuged at 200×g for about 5 min. Horse serum is added to the supernatant to neutralize excess protease. The pellet is resuspended in fresh protease, stirred for about 30 min more under the previous conditions, and manually triturated, ultimately through a 23-gauge needle. Again, horse serum is added, then the cells from both digests are combined, pelleted (200×g for about 15 min), washed, resuspended in culture medium and counted. Cells are plated at $6.0–6.5 \times 10^4$ cells per $cm^2$ in 48-well Costar dishes and cultured. for 3–4 days in Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate before assaying for GH secretion.

Just prior to assay, culture wells are rinsed twice, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the culture medium, which is centrifuged at 2000×g for about 15 minutes to remove cellular material. Rat growth hormone concentrations in the supematants are determined by a standard radioimmunoassay protocol using a rat growth hormone reference preparation (NIDDK-rGH-RP-2) and rat growth hormone antiserum raised in monkey (NIDDK-anti-rHS-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu Ci/\mu g$ by the chloramine T method for use as tracer. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.06–2.5 µg rat growth hormone per tube above basal levels. Active compounds typically stimulate growth hormone release by greater than 1.4 fold. Reference: Cheng, K., Chan, W.-S., Barreto, Jr., A., Convey, E. M., Smith, R. G. 1989. Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each compound is tested with n=3. Rats are weighed and anesthetized via intraperitoneal injection of sodium pentobarbital (Nembutol, 50 mg/kg body weight). Fourteen minutes after anesthetic administration, a blood sample is taken by nicking the tip of the tail and allowing the blood to drip into a microcentrifuge tube (baseline blood sample, approximately 100 µl). Fifteen minutes after anesthetic administration, test compound is delivered by intravenous injection into the tail vein, with a total injection volume of 1 ml/kg body weight. Additional blood samples are taken from the tail at 5, 10 and 15 minutes after compound administration. Blood samples are kept on ice until serum separation by oentrifugation (1430×g for 10 minutes at 10° C.). Serum is stored at −80° C. until serum growth hormone determination by radio-immunoassay as described above and below.

Assessment of Exogenously-Stimulated Growth Hormone Release in the Dog after Oral Administration On the day of experimentation, the test compound is weighed out for the appropriate dose and dissolved in water. Doses are delivered at a volume of 0.5 ml/kg by gavage to 4 dogs for each dosing regimen. Blood samples (2 ml) are collected from the jugular vein by direct vena puncture pre-dose and at 0.08, 0.17, 0.25, 0.5, 0.75, 1, 2, 4, 6, and 8 hours post dose using 2 ml vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 µCi/µg. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.08–2.5 µg canine GH/tube.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range is 0.01 to 5.0 mg/kg of body weight daily which can be administered as a single dose or divided into multiple doses.

The preparation of the compounds of Formula I of the present invention can be carried out in sequential or convergent synthetic routes. Syntheses detailing the preparation of the compounds of Formula I in a sequential manner are presented in the reaction schemes shown hereinbelow.

Many protected amino acid derivatives are commercially available, where the protecting groups Prt, $Z^{100}$ and $Z^{200}$ are, for example, BOC, CBZ, benzyl, ethoxycarbonyl groups, $CF_3C(O)$—, FMOC, TROC, trityl or tosyl. Other protected amino acid derivatives can be prepared by literature methods. Some 3-oxo-2-carboxyl pyrrolidines, and 4-oxo-3-carboxyl piperidines are commercially available, and many other related pyrrolidines and 4-substituted piperidines are known in the literature.

Many of the schemes illustrated below describe compounds which contain protecting groups Prt, $Z^{100}$ or $Z^{200}$.

Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi may be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane, ethyl acetate, ether or methanol at a temperature of about −30 to 70° C., preferably about −5 to about 35° C.

Benzyl esters of amines can be removed by a number of methods including, catalytic hydrogenation with hydrogen in the presence of a palladium catalyst in a protic solvent such as methanol. Hydrogen pressures from 1–1000 psi may be employed; pressures from 10 to 70 psi are preferred. The addition and removal of these and other protecting groups are discussed by T. Greene in Protective Groups in Organic Synthesis, John Wiley & Sons, New York, 1981.

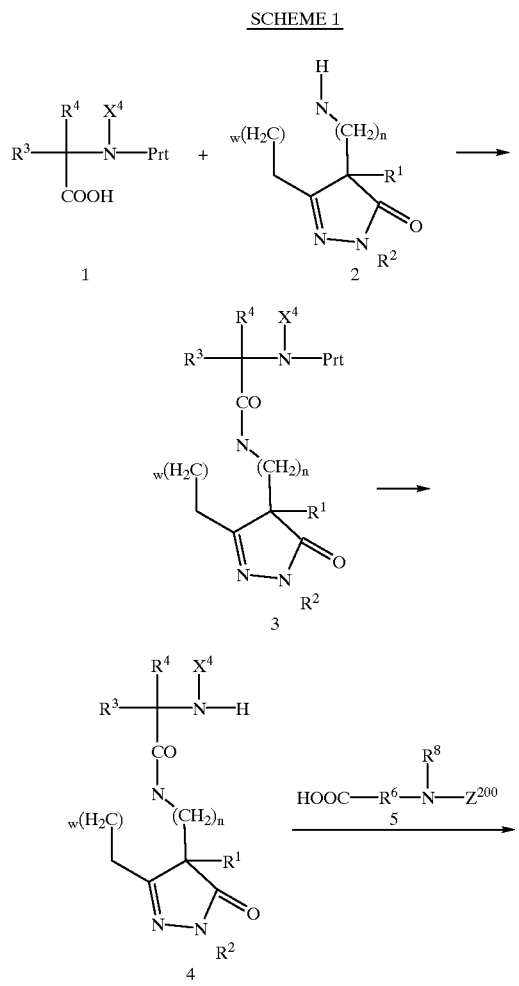

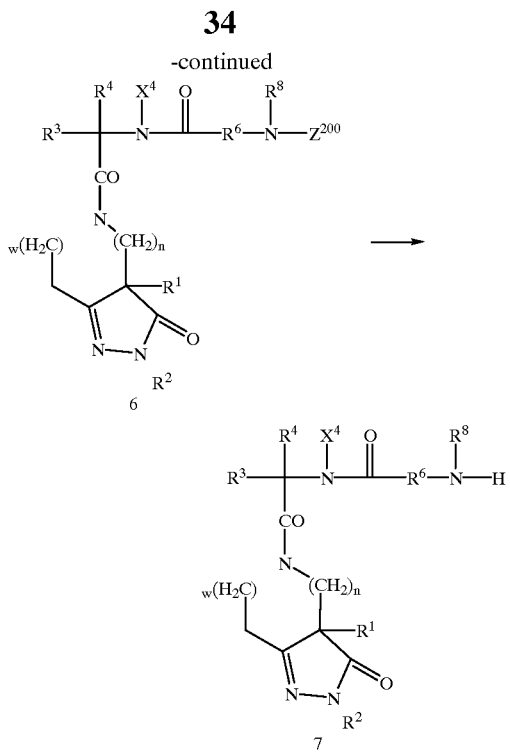

SCHEME 1: The protected amino acid derivatives 1 are in many cases commercially available, where the protecting group Prt is, for example, BOC, FMOC or CBZ groups. Other amino acids can be prepared by literature methods.

As illustrated in Scheme 1, coupling of amines of formula 2 with protected amino acids of formula 1, where Prt is a suitable protecting group, is conveniently carried out in an inert solvent such as dichloromethane or DMF by a coupling reagent such as EDC or DCC in the presence of HOBT or HOAT. In the case where the amine is present as the hydrochloride salt, it is preferable to add one or two equivalents of a suitable base such as triethylamine to the reaction mixture. Alternatively, the coupling can be effected with a coupling reagent such as BOP in an inert solvent such as methanol. Such coupling reactions are generally conducted at temperatures of about −30° to about 80° C., preferably −10° to about 25° C. For a discussion of other conditions used for coupling peptides see Houben-Weyl, Vol. XV, part II, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization or by trituration.

Transformation of the compound of formula 3 into intermediates of formula 4 can be carried out by removal of the protecting group Prt as described above. Coupling of intermediates of formula 4 to amino acids of formula 5 can be effected as described above to give intermediates of formula 6. Deprotection of the amine 6 affords compounds of formula 7.

SCHEME 2

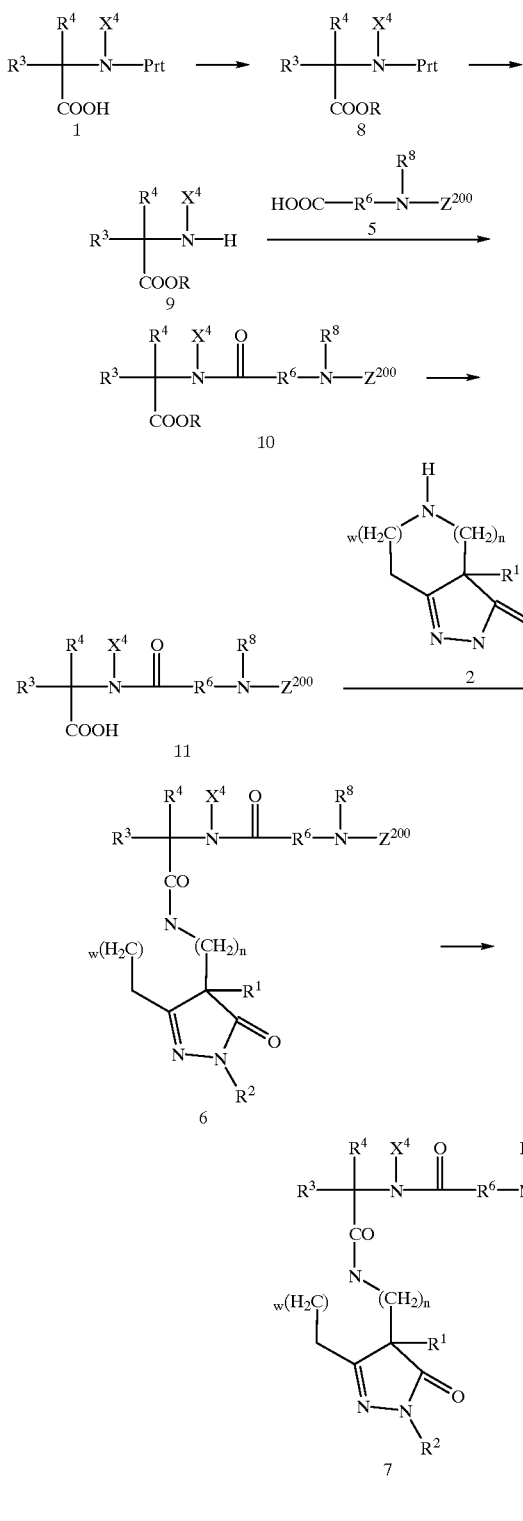

SCHEME 2: Alternatively, compounds of formula 7 can be prepared by a convergent route as shown in Scheme 2. Intermediate esters of formula 8 can be prepared by treating amino acids 1, where Prt is a suitable protecting group, with a base such as potassium carbonate followed by an alkyl halide such as iodomethane in a suitable solvent such as DMF. Deprotection of the amine transforms 8 into 9. Alternatively, many amino acids of formula 9 are commercially available. Intermediate 10 is generated by coupling 9 to amino acid 5. The ester of intermediate 10 can be converted to intermediate acid 11 by a number of methods known in the art; for example, methyl and ethyl esters can be hydrolyzed with lithium hydroxide in a protic solvent such as aqueous methanol or aqueous THF at a temperature of about $-20°$ to $120°$ C., preferably about $0°$ to $50°$ C. In addition, removal of a benzyl group can be accomplished by a number of reductive methods including hydrogenation in the presence of platinum or palladium catalyst in a protic solvent such as methanol. Acid 11 can then be coupled to amine 2 to give intermediates of formula 6. Transformation of 6 to 7 can be achieved by removal of the protecting group $Z^{200}$.

SCHEME 3

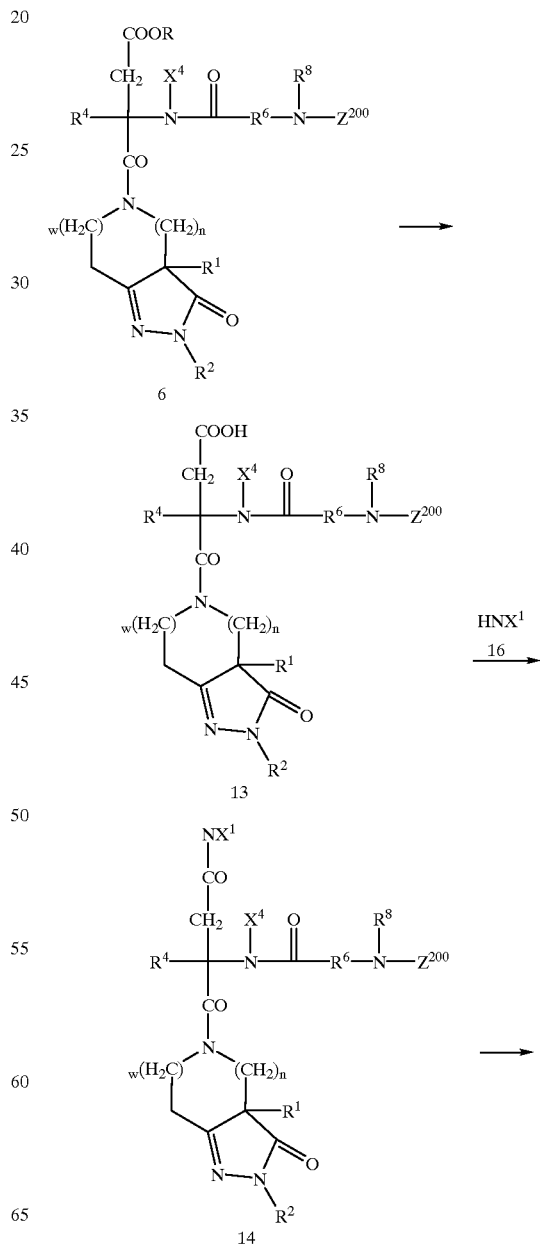

-continued

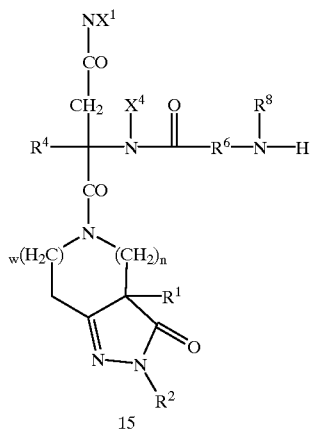

15

SCHEME 5

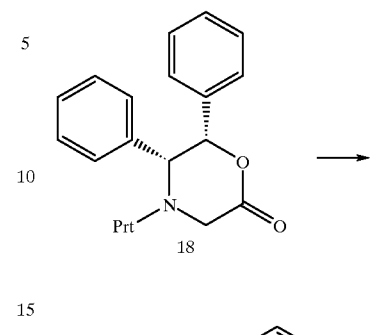

SCHEME 3: The esters of formula 6 can be converted to intermediate acids of formula 13 by a number of methods known in the art; for example, methyl and ethyl esters can be hydrolyzed with lithium hydroxide in a protic solvent such as aqueous methanol or aqueous THF at a temperature of about −20° to 120° C., preferably about 0° to 50° C. In addition, removal of a benzyl group can be accomplished by a number of reductive methods including hydrogenation in the presence of platinum or palladium catalyst in a protic solvent such as methanol. Coupling the acid 13 to amine 16 generates the intermediates of formula 14. Transformation of 14 to 15 can be achieved by removal of the protecting group $Z^{200}$.

SCHEME 4

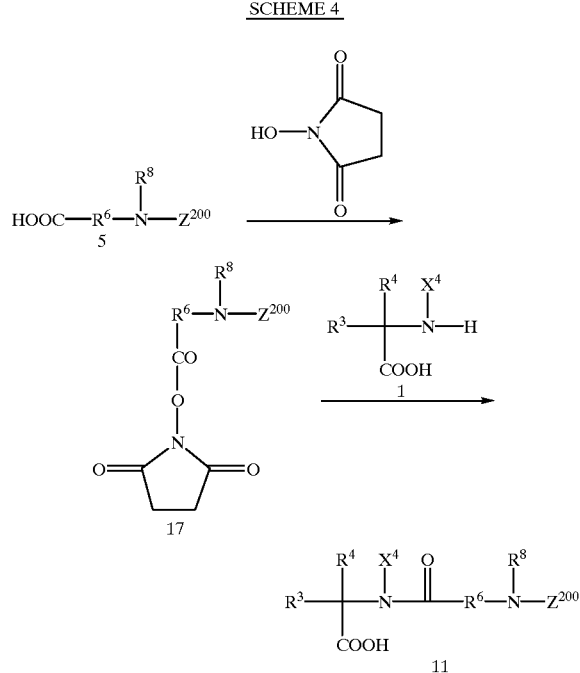

SCHEME 4: Esters of formula 17 can be prepared by treating an acid of formula 5 with hydroxysuccinimide in the presence of a coupling agent such as EDC in an inert solvent such as methylene chloride as illustrated in Scheme 4. Treatment of an ester 17 with an amino acid of formula 1 in a solvent such as dioxane, THF or DMF in the presence of a base such as diisopropylethylamine produces 11.

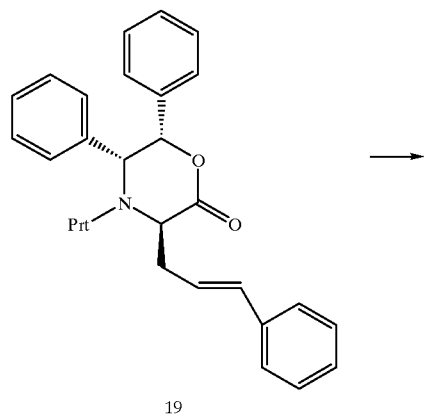

SCHEME 5: As illustrated in Scheme 5, alkylation of the diphenyloxazinone of formula 18 with cinnamyl bromide in the presence of sodium bis(trimethylsilyl)amide generates 19 which is then converted to the desired (D)-2-amino-5-phenylpentanoic acid 20 by removing the protecting group (Prt) and hydrogenation over a $PdCl_2$ catalyst.

SCHEME 6

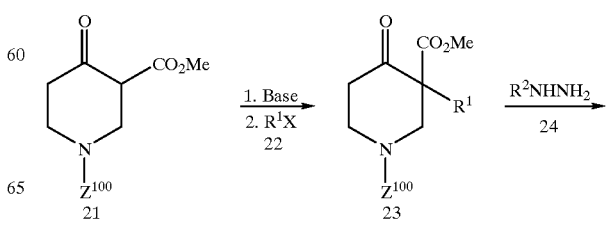

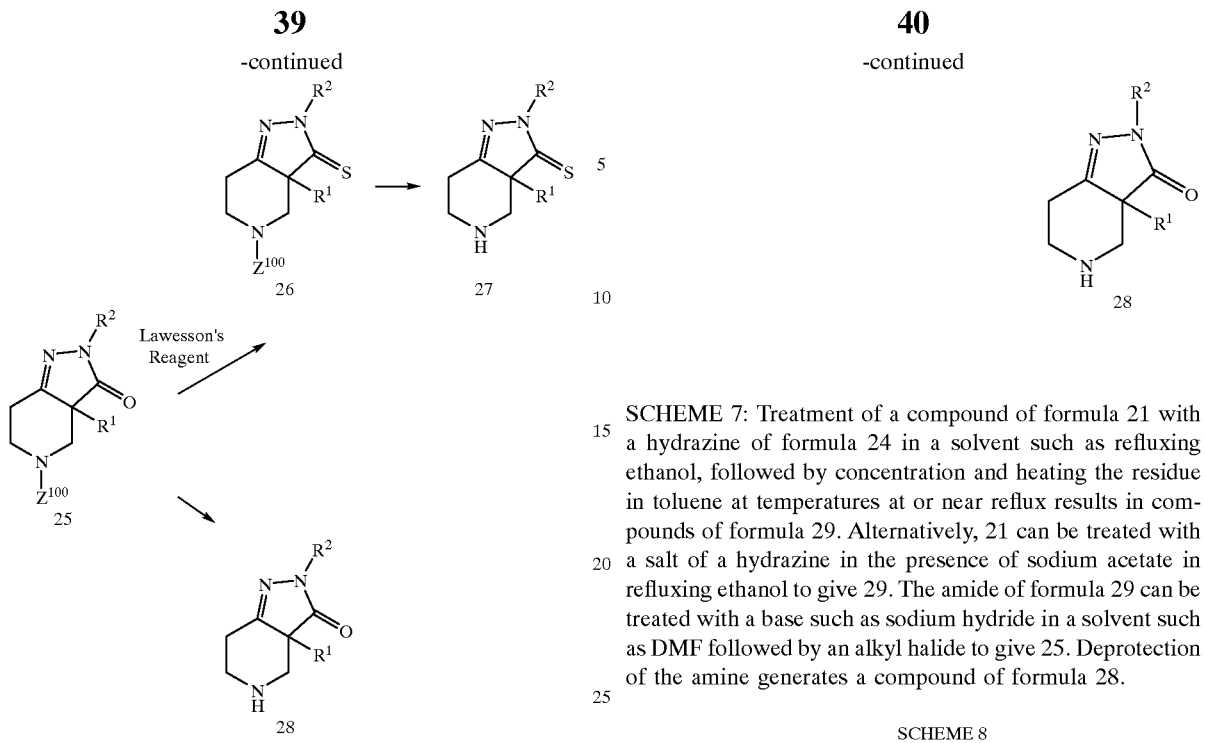

SCHEME 6: Treatment of an ester of formula 21 with a base such as sodium hydride in a solvent such as DMF followed by an alkyl halide 22 generates a compound of formula 23 as illustrated in Scheme 6. Treating a compound of formula 23 with a hydrazine of formula 24 such as hydrazine or methyl-hydrazine in a solvent such as refluxing ethanol, followed by concentration and heating the residue in tolune at temperatures at or near reflux results in a compound of formula 25. Alternatively, 23 can be treated with a salt of a hydrazine in the presence of sodium acetate in refluxing ethanol to give 25. Deprotection of the amine generates a compound of formula 28. Thioamides of formula 26 can be formed by treating 25 with Lawesson's reagent in refluxing toluene or benzene. Removal of the protecting group transforms 26 into 27.

SCHEME 7

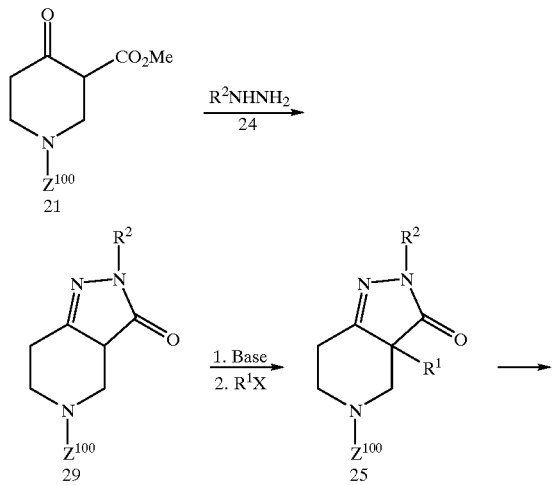

SCHEME 7: Treatment of a compound of formula 21 with a hydrazine of formula 24 in a solvent such as refluxing ethanol, followed by concentration and heating the residue in toluene at temperatures at or near reflux results in compounds of formula 29. Alternatively, 21 can be treated with a salt of a hydrazine in the presence of sodium acetate in refluxing ethanol to give 29. The amide of formula 29 can be treated with a base such as sodium hydride in a solvent such as DMF followed by an alkyl halide to give 25. Deprotection of the amine generates a compound of formula 28.

SCHEME 8

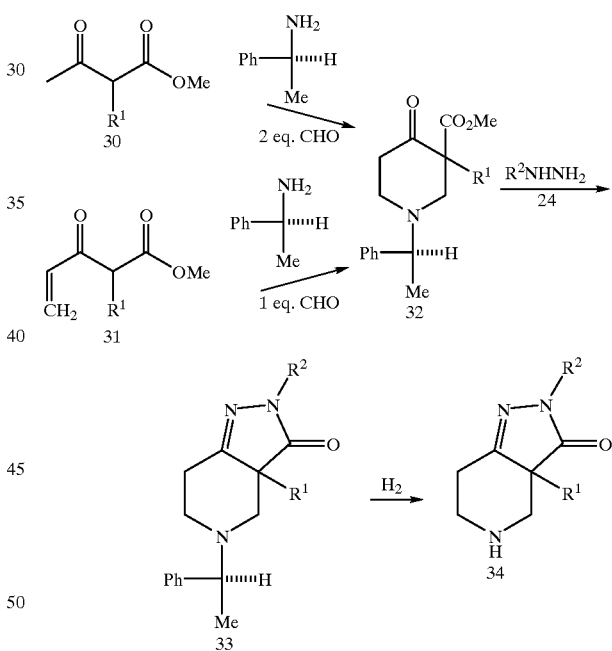

SCHEME 8: Reaction of a ketoester of formula 30 with a chiral amine such as alpha-methylbenzylamine with a suitable aldehyde such as formaldehyde, or reaction of a vinyl ketoester of formula 31 with a chiral amine such as alpha-methylbenzylamine with a suitable aldehyde such as formaldehyde, affords a compound of formula 32 via a double Mannich reaction. Reaction of 32. with a hydrazine generates a chiral compound of formula 33. Deprotection of the nitrogen with hydrogen and a suitable catalyst such as palladium affords compounds of formula 34.

SCHEME 9

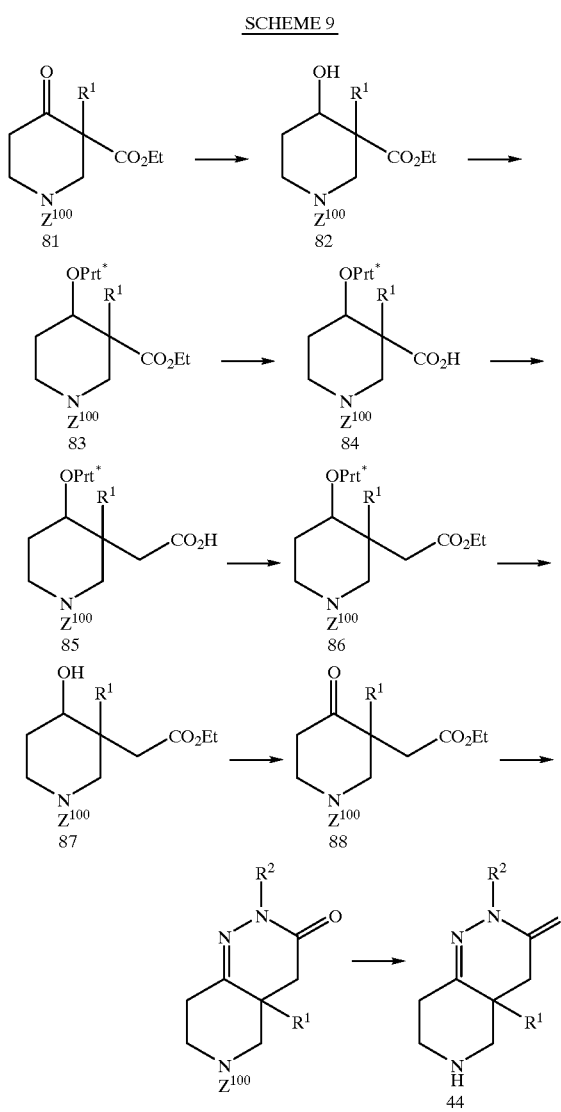

SCHEME 10

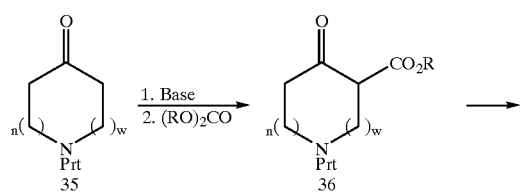

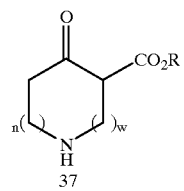

SCHEME 10: Treatment of a compound of formula 35 with a base such as sodium hydride in a solvent such as DMF followed by treatment with diethylcarbonate generates the ethyl ester of compound 36. Deprotection of the amine transforms 36 into 37.

SCHEME 11

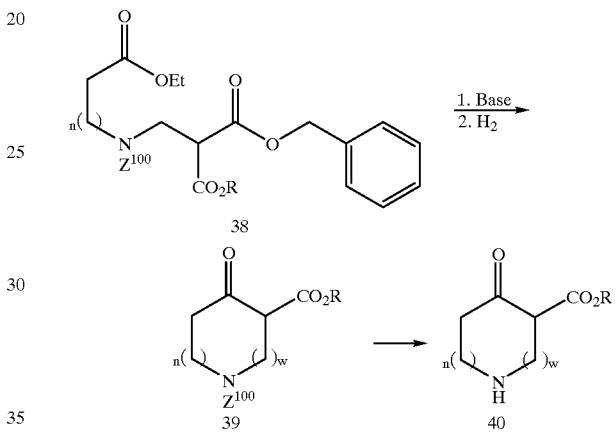

SCHEME 9: Treatment of a compound of formula 81 with a reducing agent such as sodium borohydride and protection of the nitrogen affords a compound of formula 82. Protection of the alcohol affords 83. Saponification of the ester affords a compound of formula 84. Reaction of 84 with thionyl chloride followed by treatment with diazomethane affords the homologated acid of formula 85. Esterification of 85 affords a compound of formula 86, which is O-deprotected to give 87. Oxidation of 87 affords a ketone of formula 88. Reaction of 88 with a hydrazine, followed by nitrogen deprotection affords a compound of formula 44.

SCHEME 11: Treatment of a malonic ester of formula 38 with a base such as sodium hydride in a solvent such as DMF and subsequent hydrogenolysis of the benzyl group with hydrogen and a catalyst such as palladium in a suitable solvent such as methanol produces the ester of formula 39. Deprotection of the amine generates compounds of formula 40.

SCHEME 12

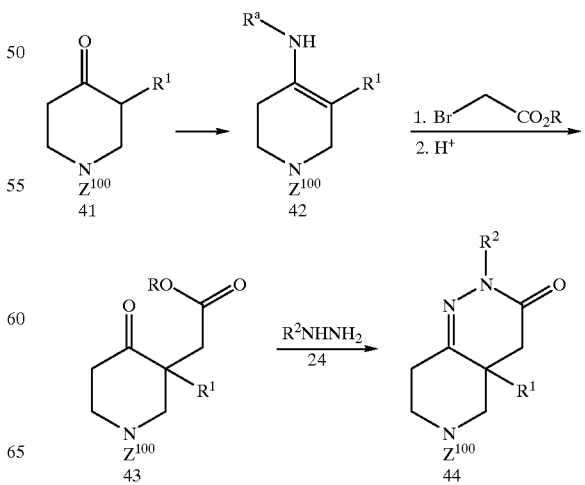

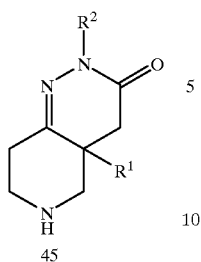

45

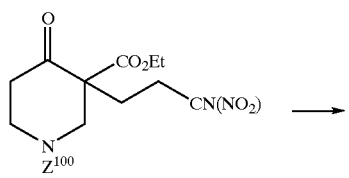

49

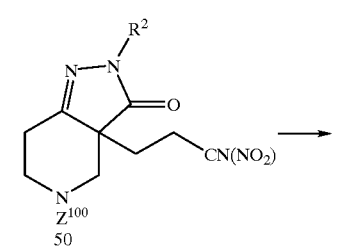

50

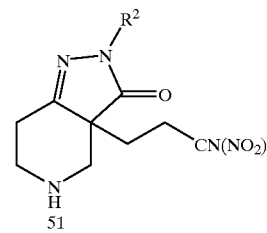

51

SCHEME 12: Treatment of a ketone of formula 41 with a secondary amine such as piperidine in a suitable solvent such as benzene with removal of water affords an enamine of formula 42. Alkylation of the enamine with an alpha-haloester such as ethylbromoacetate in a suitable solvent such as benzene or THF using a suitable base such as LDA or NaN(SiMe$_3$)$_2$ affords a ketoester of formula 43. Reaction with a hydrazine of formula 24 affords the compound of formula 44. Deprotection of the nitrogen affords compounds of formula 45.

SCHEME 13

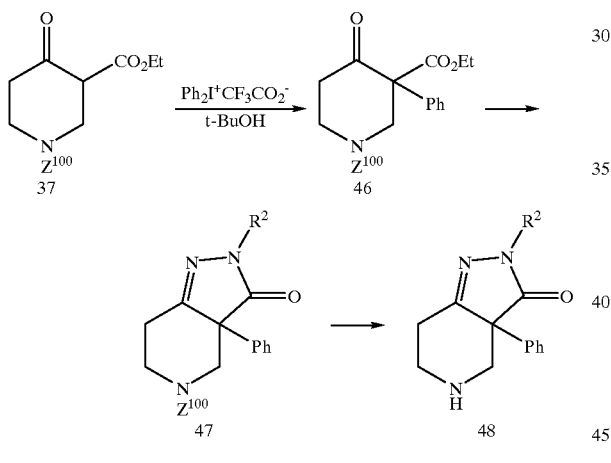

SCHEME 14: Treatment of a ketoester of formula 37 with an olefin such as acrylonitrile generates a ketoester of formula 49. Reaction of 49 with a hydrazine generates a compound of formula 50. Deprotection of the nitrogen affords compounds of formula 51.

SCHEME 15

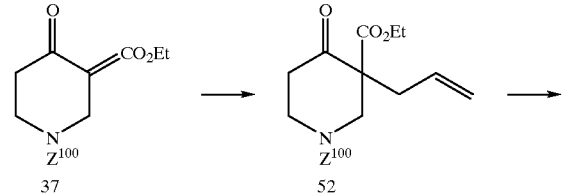

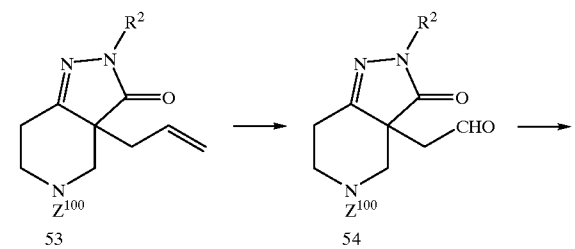

SCHEME 13: Treatment of a ketoester of formula 37 with an iodonium salt such as diphenyliodonium trifluoroacetate in a suitable solvent such as t-butanol generates a ketoester of formula 46. Reaction of 46 with a hydrazine generates a compound of formula 47. Deprotection of the nitrogen affords compounds of formula 48, see Synthesis, (9), 1984 p. 709 for a detailed description.

SCHEME 14

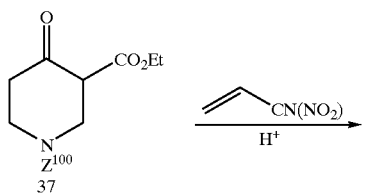

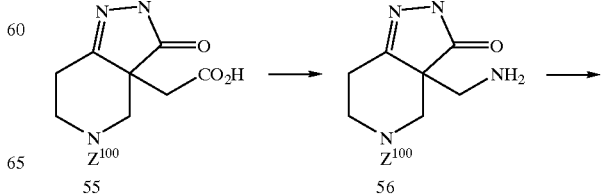

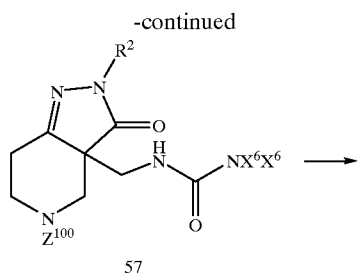

57

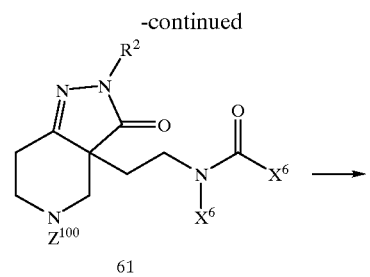

61

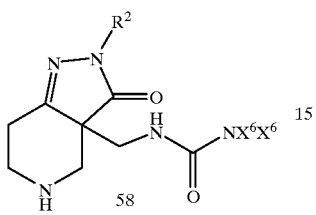

58

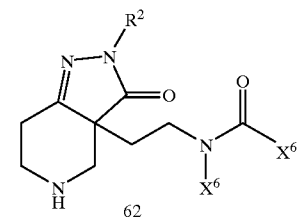

62

SCHEME 15: Treatment of a ketoester of formula 37 with allyl bromide and a suitable base such as sodium hydride in a suitable solvent such as DMF affords a ketoester of formula 52. Reaction of 52 with a hydrazine generates a compound of formula 53. Ozonolysis of 53 in a suitable solvent such as methylene chloride followed by treatment with a reducing agent such as dimethylsulfide affords an aldehyde of formula 54. Oxidation of 54 affords a carboxylic acid of formula 55. Curtius rearrangement of 55, followed by hydrolysis of the intermediate isocyanate affords a primary amine of formula 56. Treatment of a compound of formula 56 with an isocyanate or carbamate affords a urea of formula 57. Deprotection of the nitrogen affords compounds of formula 58.

SCHEME 16: Treatment of a compound of formula 54 with a primary amine affords an imine of formula 59. Reduction of a compound of formula 59 affords a compound of formula 60. Treatment of a compound of formula 60 with an acylating agent affords a compound of formula 61. Deprotection of the nitrogen affords compounds of formula 62.

SCHEME 17

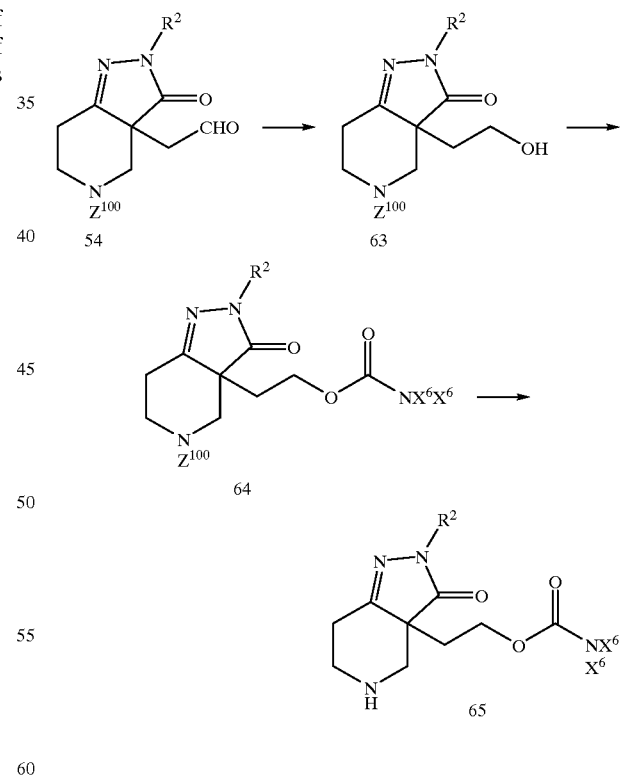

SCHEME 16

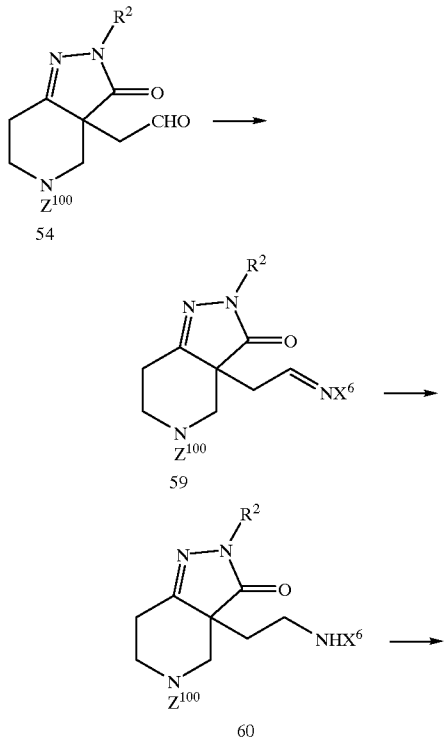

SCHEME 17: Treatment of a compound of formula 54 with a reducing agent such as sodium borohydride affords a compound of formula 63. Reaction of 63 with an acylating agent such as an isocyanate or carbamate affords compounds of formula 64. Deprotection of the nitrogen affords compounds of formula 65.

SCHEME 18

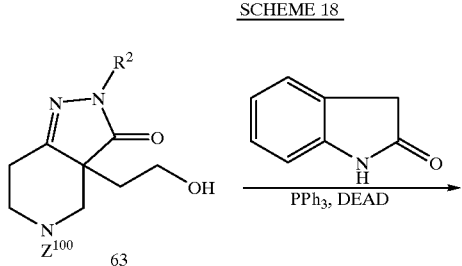

SCHEME 18: Treatment of a compound of formula 63 with a phosphine such as triphenyl phosphine and an azo compound such as diethylazodicarboxylate and an oxindole affords a compound of formula 66. Deprotection of the nitrogen affords the compound of formula 67.

SCHEME 19

SCHEME 19: Treatment of a ketoester of formula 37 with a chiral diol and acid catalyst with removal of water in a suitable solvent such as benzene affords a chiral ketal formula 68. Alkylation of 68 with an alkyl halide in the presence of a base such as LDA followed by acid-catalyzed hydrolysis of the ketal affords chiral ketoesters of formula 69. Reaction of 69 with a hydrazine generates chiral compounds of formula 70. Deprotection of the nitrogen affords compounds of formula 71.

SCHEME 20

SCHEME 20: Treatment of a ketoester of formula 37 with a chiral amino acid ester such as valine t-butyl ester affords a chiral enamine of formula 72. Alkylation of 72 with an alkyl halide in the presence of a base such as LDA followed by acid-catalyzed hydrolysis of the enamine affords chiral ketoesters of formula 69. Reaction of 69 with a hydrazine generates chiral compounds of formula 70. Deprotection of the nitrogen affords compounds of formula 71.

SCHEME 21

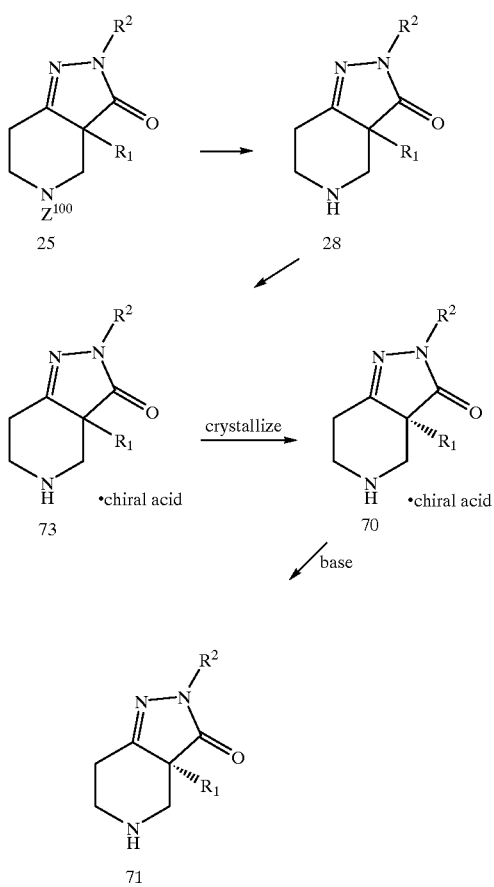

SCHEME 21: Deprotection of the nitrogen of 25 affords compounds of formula 28. Salt formation of 28 with chiral acid affords a mixture of diastereomeric salts of formula 73. Crystallization of the diastereomeric salts affords the acid salt of chiral compounds of formula 70. Decomposition of the salt 70 with base liberates chiral compounds of formula 71.

SCHEME 22

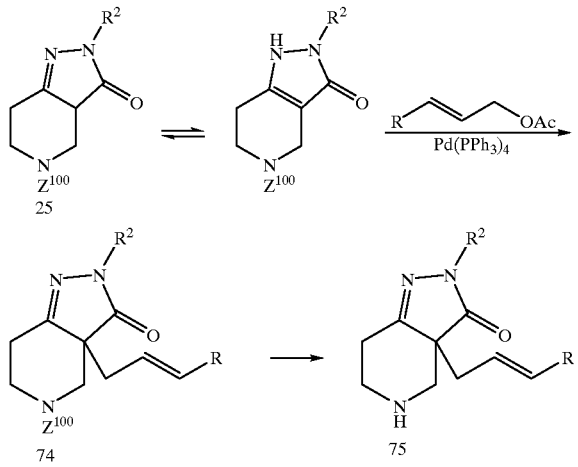

SCHEME 22: Alkylation of compounds of formula 25 with an allylic acetate in the presence of a suitable catalyst such as palladium tetrakis(triphenylphosphine) affords compounds of formula 74. Deprotection of the nitrogen affords compounds of formula 45, see Tetrahedron (50) p.515, 1994 for a detailed discussion.

SCHEME 23

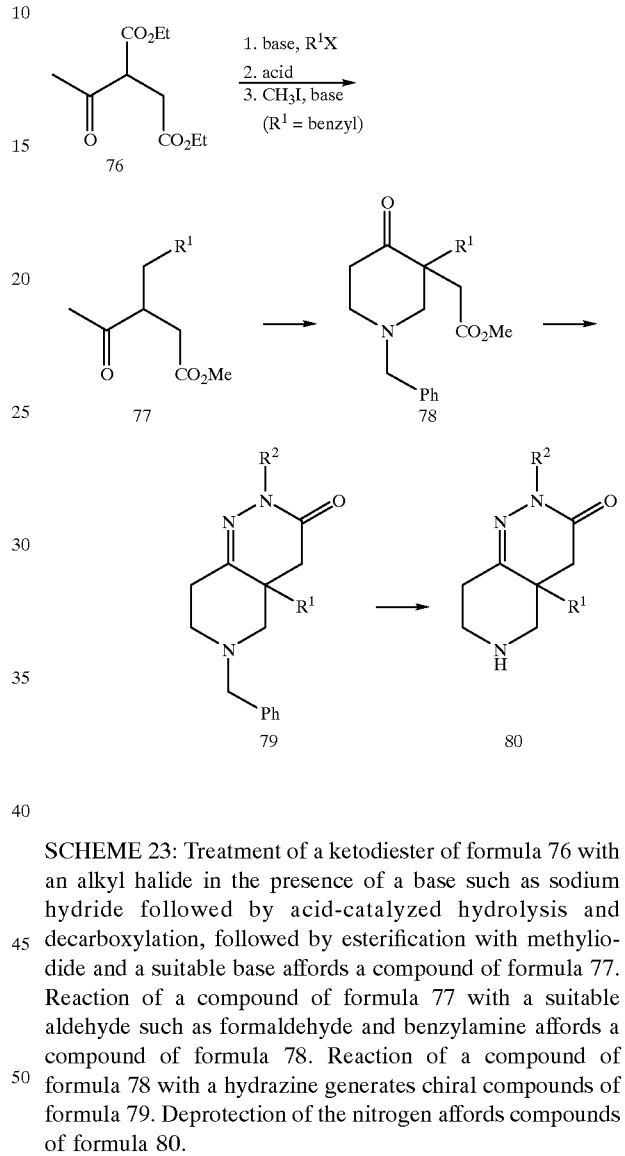

SCHEME 23: Treatment of a ketodiester of formula 76 with an alkyl halide in the presence of a base such as sodium hydride followed by acid-catalyzed hydrolysis and decarboxylation, followed by esterification with methyliodide and a suitable base affords a compound of formula 77. Reaction of a compound of formula 77 with a suitable aldehyde such as formaldehyde and benzylamine affords a compound of formula 78. Reaction of a compound of formula 78 with a hydrazine generates chiral compounds of formula 79. Deprotection of the nitrogen affords compounds of formula 80.

SCHEME 24

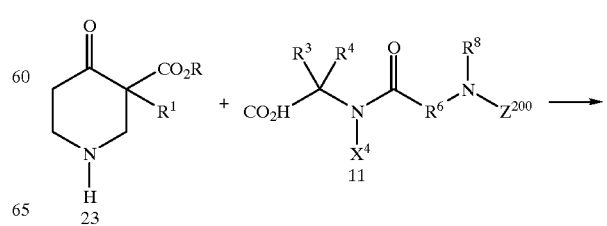

SCHEME 25

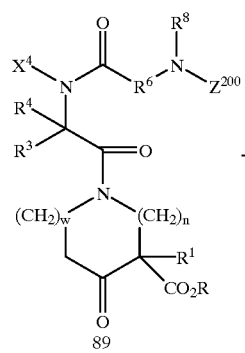

89

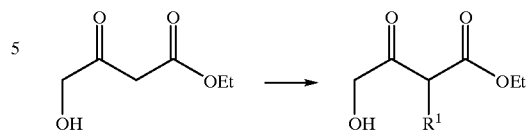

90 → 91

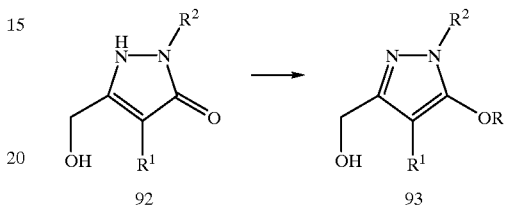

92 → 93

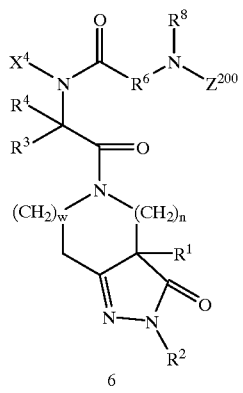

6

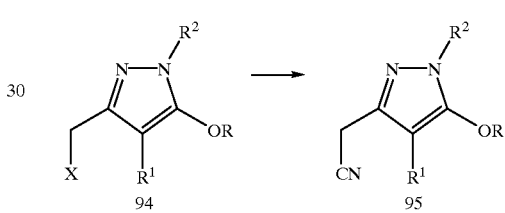

94 → 95

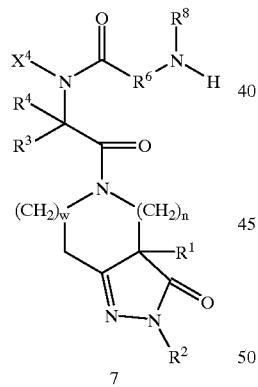

7

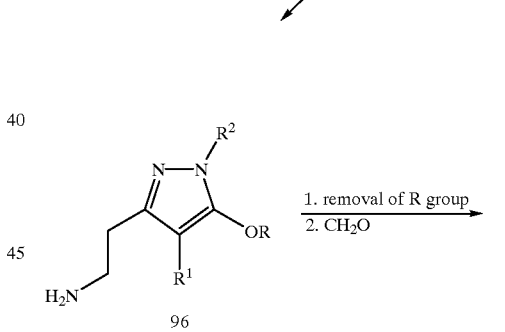

96

1. removal of R group
2. $CH_2O$

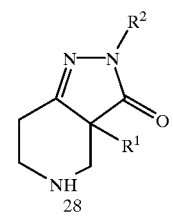

28

SCHEME 24: Treatment of an amine of formula 23 with an acid of formula 11 in an inert solvent such as dichloromethane or DMF by a coupling reagent such as EDC or DCC in the presence of HOBT affords compounds of formula 89. Reaction of compounds of formula 89 with a hydrazine generates compounds of formula 6. Deprotection of the nitrogen affords compounds of formula 7.

SCHEME 25: Treatment of a hydroxyacetoacetate ester of formula 90 with an alkyl halide in the presence of a suitable base such as sodium hydride affords compounds of formula 91. Reaction of 91 with a hydrazine generates compounds of formula 92. O-Alkylation of the carbonyl oxygen of 92 affords 93 which is converted to the halide 94. Displacement of the halide X by cyanide ion affords the nitrile 95. Reduction of 95 gives the primary amine 96 which is deprotected and cyclized in the presence of formaldehyde to afford 28.

SCHEME 26

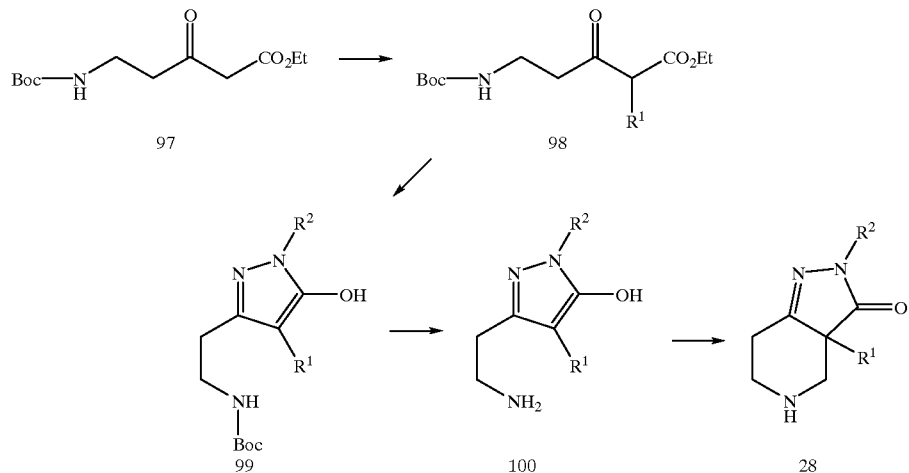

SCHEME 26: Treatment of a beta-keto-protected aminovalerate such as 97 with an alkyl halide in the presence of a suitable base such as sodium hydride affords compounds of formula 98. Reaction of compounds of formula 98 with a hydrazine generates compounds of formula 99. Deprotection of compounds of formula 99 affords primary amines of formula 100. Cyclization of compounds of formula 100 in the presence of formaldehyde affords compounds of formula 28.

SCHEME 27

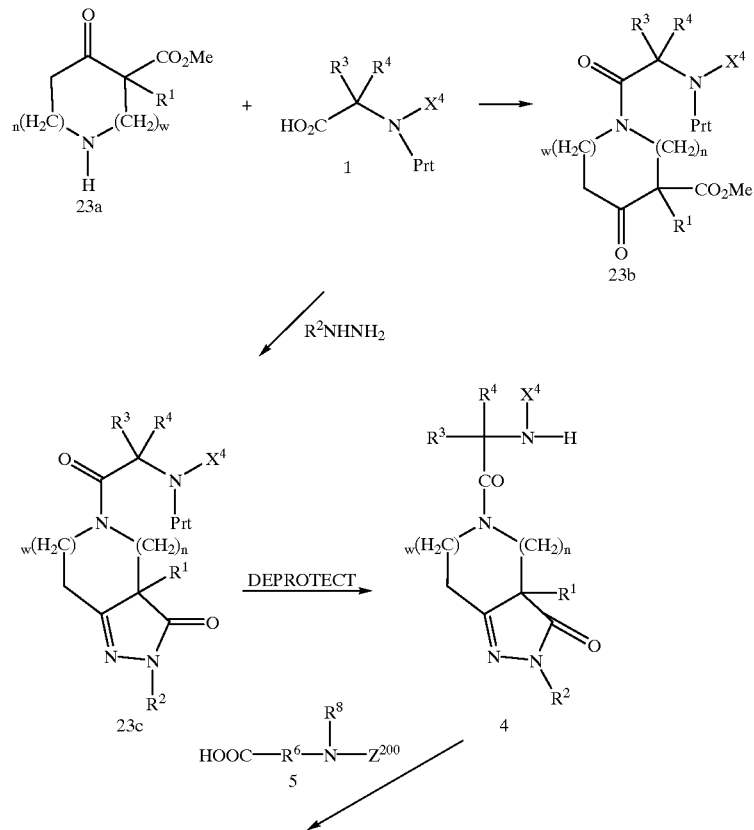

-continued

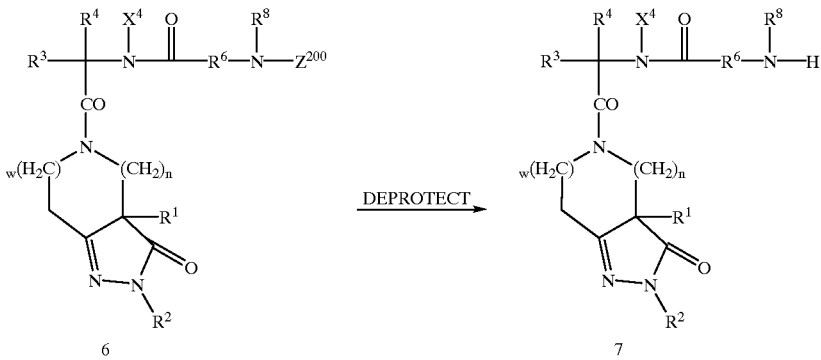

SCHEME 27: Treatment of the amine of formula 23a with an acid such as 1 in the presence of EDC and HOAT in a suitable solvent provides keto-esters of formula 23b. The keto-ester 23b can be treated with a salt of hydrazine in the presence of sodium acetate in refluxing ethanol to give hydrazines of formula 23c. Deprotection under suitable conditions gives amines of formula 4. Coupling of intermediates of formula 4 to amino acids of formula 5 can be effected as described above to give intermediates of formula 6. Deprotection of amine 6 affords compounds of formula 7.

The following examples are provided for the purpose of further illustration only and are not intended to be limitations on the disclosed invention.

General Experimental Procedure

Amicon silica 30 μM, 60 Å pore size, was used for column chromatography. Melting points were taken on a Buchi 510 apparatus and are uncorrected. Proton and carbon NMR spectra were recorded on a Varian XL-300, Bruker AC-300, Varian Unity 400 or Bruker AC-250 at 25° C. Chemical shifts are expressed in parts per million down field from trimethylsilane. Particle beam mass spectra were obtained on a Hewlett-Packard 5989A spectrometer using ammonia as the source of chemical ionization. For initial sample dissolution, chloroform or methanol was employed. Liquid secondary ion mass spectra (LSIMS) were obtained on a Kratos Concept-1S high resolution spectrometer using cesium ion bombardment on a sample dissolved in a 1:5 mixture of dithioerythritol and dithiothreitol or in a thioglycerol matrix. For initial sample dissolution chloroform or methanol was employed. Reported data are sums of 3–20 scans calibrated against cesium iodide. TLC analyses were performed using E. Merck Kieselgel 60 F254 silica plates visualized (after elution with the indicated solvent(s)) by staining with 15% ethanolic phosphomolybdic acid and heating on a hot plate.

General Procedure A (Peptide coupling using EDC): A 0.2–0.5 M solution of the primary amine (1.0 equivalent) in dichloromethane (or a primary amine hydrochloride and 1.0–1.3 equivalents of triethylamine) is treated sequentially with 1.0–1.2 equivalents of the carboxylic acid coupling partner, 1.5–1.8 equivalents hydroxybenzotriazole hydrate (HOBT) or HOAT and 1.0–1.2 equivalents (stoichiometrically equivalent to the quantity of carboxylic acid) 1-(3-dimethylaminopropyl)-3-ethylcarbodiimide hydrochloride (EDC) and the mixture is stirred overnight in an ice bath (the ice bath is allowed to warm, thus the reaction mixture is typically held at about 0–20° C. for about 4–6 h and about 20–25° C. for the remaining period). The mixture is diluted with ethyl acetate or other solvent as specified, and the resulting mixture washed twice with 1N NaOH, twice with 1N HCl (if the product is not basic), once with brine, dried over $Na_2SO_4$, and concentrated giving the crude product which is purified as specified. The carboxylic acid component can be used as the dicyclohexylamine salt in coupling to the primary amine or hydrochloride of the latter; in this case no triethylamine is employed.

EXAMPLE 1

2-Amino-N{1(R)-benzyloxymethyl-2-[3a-(R)-(4-fluoro-benzyl)-2-methyl-3-oxo-2,3,3a,4,6,7-hexahydro-pyrazolo[4,3-c]pyridin-5-yl]-2-oxo-ethyl}-isobuyramide Hydrochloride and 2-Amino-N-{1-(R)-benyloxymethyl-2-[3a-(S)-(4-fluorobenzyl)-2-methyl-3-oxo-2,3,3a,4,6,7-hexahydro-pyrazolo[4,3-c]pyhdin-5-yl]-2-oxo-ethyl}-isobeyramide Hydrochloride A. 4-Oxo-piperidine-1.3-dicarboxylic Acid 1-tert-butyl Ester 3-ethyl Ester A mixture of 8.00 g (38.5 mmol) of 4-oxo-piperidine-3-carboxylic acid ethyl ester hydrochloride, 9.23 g (42.4 mmol) of di-tert-butyidicarbonate, and 3.89 g (38.5 mmol) of triethylamine in 150 mL of THF was stirred at room temperature for about 72 h. The mixture was concentrated and the residue was dissolved in ethyl acetate and washed three times each with 10% aqueous HCl, saturated aqueous sodium bicarbonate solution, and brine, dried over $MgSO_4$, and concentrated to give 10.0 g of 1A as a white solid. MS (Cl, $NH_3$) 272 (MH$^+$).

B. 3-(R,S)-(4-Fluoro-benzy)-4-oxo-piperidine-1.3-dicarboxylic Acid 1-tert-butyl Ester 3-ethyl Ester To a solution of 2.00 g (7.4 mmol) 1A in 10 mL of DMF was added 282 mg (7.4 mmol) of sodium hydride (60% oil dispersion) and the mixture was stirred at room temperature for about 15 min. A solution of 1.39 g (7.4 mmol) 4-fluorobenzyl bromide in 7 mL of DMF was added to the stirring solution and the mixture was stirred for about 72 h at room temperature. The mixture was diluted with ethyl acetate and washed once with water and four times with brine, dried over $MgSO_4$, and concentrated to give 2.8 g of 1B. MS (Cl, $NH_3$) 380 (MH$^+$).

C. 3a-(R,S)-(4-Fluoro-benzyl)-2-methyl-3-oxo-2,3,3a,4,6,7-hexahydro-pyrazolo[4.3-c]pyridine-5-carboxylic Acid Tert-butyl Ester A mixture of 2.54 g (6.7 mmol) of 1B and 309 mg (6.7 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography using an elution gradient of (18:82 v/v ethyl acetate:hexane) to (75:25 v/v ethyl acetate:hexane) to give 1.0 g of 1C as a clear colorless oil. MS (Cl, $NH_3$) 362 ($MH^+$).

D. 3a-(R S)-(4-Fluoro-benzyl)-2-methyl-2,3a,4,5,6,7-hexahydrmpyrazolo[4,3-c]pyridin-3-one Trifluoroacetate To 1.00 g (2.8 mmol) of 1C was added 10 mL of trifluoroacetic acid at about 0° C. and the mixture was stirred for about 1 h. Ethyl acetate was added and the mixture was concentrated to give 1.0 g of 1D. MS (Cl, $NH_3$) 263 ($MH^+$).

E. (R)-3-Benzyloxy-2-(2-tert-butoxycarbonylamino-2-methyl-propionylamino)-propionic Acid To 1.83 g (6.2 mmol) of N-t-BOCO-benzyl-D-serine in 35 mL of DMF was added 1.02 g (7.4 mmol) of potassium carbonate followed by 0.92 g (6.5 mmol) of iodomethane. The mixture was stirred overnight at about 24° C. under an atmosphere of nitrogen. The reaction mixture was diluted with 200 mL of water, and extracted three times with ethyl acetate. The combined organics were washed five times with water and once with brine, dried over $MgSO_4$ and concentrated. The crude (R)-3-benzyloxy-2-tert-butoxycarbonyl-amino-propionic acid methyl ester was dissolved in 15 mL of cold trifluoroacetic acid at about 0° C. and the mixture was stirred for about 2 h. The mixture was concentrated and the residue was diluted with 1N NaOH and extracted three times with ethyl acetate. The combined organic extracts were washed with brine and dried over $Na_2SO_4$ to give 0.84 g (4.02 mmol) of the resulting (R)-2-amino-3-benzyloxy-propionic add methyl ester which was coupled to 0.81 g (4.02 mmol) of N-t-BOC-α-methylalanine to give 1.80 g of (R)-3-benzyloxy-2-(2-tert-butoxycarbonylamino-2-methyl-propionylamino)propionic acid methyl ester. The crude product was dissolved in 20 mL of 4:1 THF:water and a solution of 335 mg (7.98 mmol) of lithium hydroxide hydrate in 1 mL of water was added to the solution and the mixture was stirred overnight at room temperature. The mixture was concentrated and the residue was diluted with ethyl acetate and acidified with aqueous HCl and extracted three times with ethyl acetate. The organic extracts were combined and washed once with brine, dried over $Na_2SO_4$ and concentrated to give 1.60 g of 1E as an oil which solidified on standing. $^1H$ NMR ($CDCl_3$ 300 MHz) δ 7.30 (m, 5H), 7.10 (d, 1H), 5.07 (bs, 1H), 4.68 (m, 1H), 4.53 (q, 2H) 4.09 (m, 1H), 3.68 (m, 1H), 1.3–1.5 (m, 15H).

F. (1-{1-(R)-Benzyloxymethyl-2-[3a-(R,S)-(4-fluoro-benzyl)-2-methyl-3-oxo-2,3a,4,6,7-exahydrho-pyrazolo[4,3-c]pyridin-5-yl]-2-oxo-ethylcarbamoyl}-1-methyl-ethyl)-carbamic Acid Tert-butyl Ester According to the method outlined in General Procedure A, 193 mg (0.51 mmol) of 1D and 196 mg (0.51 mmol) of 1E were coupled to give a mixture of diastereomers. The residue was purified by silica gel chromatography using an elution gradient of (1:1 v/v ethyl acetate:hexane) to 100% ethyl acetate to give 60 mg of less polar 1F isomer 1 and 100 mg of more polar 1F isomer 2. MS (Cl, $NH_3$) 624 ($MH^+$) for both isomers.

G. 2-Amino-N-{1(R)-benzyloxymethyl-2-[3a-(R)-(4-fluoro-benzyl)-2-methy-3-oxo-2,3,3a,4,6,7-hexahydropyrazolo[4,3-c]pyndin-5-yl]-2-oxo-ethyl}isobldyramode Hydrochloride To 60 mg (0.10 mmol) of 1F isomer 1 in 10 mL of ethanol was added 4 mL of concentrated HCl and the mixture was stirred at room temperature for about 2 h. The mixture was concentrated and the residue was precipitated from etha-novhexane to give 50 mg of 1G isomer 1 as a white powder. MS (Cl, $NH_3$) 524 ($MH^+$). $^1HNMR$ ($CD_3OD$): (partial) δ 7.32 (m, 5 H), 7.12 (m, 2 H), 6.91 (m, 2 H), 5.15 (m, 1H), 4.54 (s, 2 H), 3.78 (m, 2 H)3.02 (m, 7 H), 2.66 (m, 2 H), 1.57 (s, 6 H).

H. 2-Amino-N-{1(R)-benzyloxymethyl-2-[3a-(S)-(4-fluoro-benzyl)-2-methyl-3-oxo-2,3,3a,4,6,7-hexahydropyrazolo[4.3c]pyridin-5-yl]-2-oxo-ethyl}-isobtramode Hydrochloride To 100 mg (0.16 mmol) of 1F isomer 2 in 10 mL of ethanol was added 4 mL of concentrated HCl and the mixture was stirred at room temperature for about 2 h. The mixture was concentrated and the residue was precipitated from ethanolihexane to give 60 mg of 1H isomer 2 as a white powder. MS (Cl, $NH_3$) 524 ($MH^+$). $^1HNMR$ ($CD_3OD$): (partial) δ 7.32 (m, 5 H), 7.08 (m, 2 H), 6.95 (m, 2 H), 6.80 (m, 2 H), 5.30 (m, 1 H), 4.61 (m, 3 H), 3.80 (m, 2 H), 2.58 (m, 3 H), 1.58 (s, 6 H).

EXAMPLE 2

2-Amino-N-[2-[3a-(R,S)-(4-fluoro-benzyl)-2-methyl-3oxo-2,3,3a,4,6,7-hexahydro-pyrazolo[4,3-c]pyridin-5-yl]-1(R)-(1H-indol-3-ylmethyl)-2-oxo-ethyl]-osobutyramide Hydrochloride A. (R)-2-Amino-3-[1H-indol-3-yl)-propionic Acid Methyl Ester To 4.92 g (16.2 mmol) of N-α-t-BOC-D-tryptophan in 100 mL of DMF was added 2.46 g (17.8 mmol) of potassium carbonate followed by 2.41 g (17.0 mmol) of iodomethane, and the mixture was stirred overnight at 24° C. under an atmosphere of nitrogen. The reaction mixture was diluted with water, and extracted three times with ethyl acetate. The combined organics were washed five times with 500 mL of water and once with brine, dried over $MgSO_4$ and concentrated to give 4.67 g of a white solid. To the crude (R)-2-tert-butoxycarbonylamino-3-(1H-indol-3yl)-propionic acid methyl ester was added 15 mL of cold trifluoroacetic acid at about 0° C. and the mixture was stirred for about 2 h. The mixture was concentrated and the residue was diluted with 1N NaOH and extracted three times with ethyl acetate. The combined organic extracts were washed with brine and dried over $Na_2SO_4$ to give (R)-2-amino-3-(1H-indol-3-yl)-propionic acid methyl ester as an orange oil in quantitative yield.

B. (R)-2-(2-tert-Butoxycarbonylamino-2-methyl-2-dropionylamono)-3-(1H-indol-3-yl)-propionic Acid Methyl Ester.

The crude product from 2A 1.55 g (7.1 mmol) was coupled to 1.44 g (7.1 mmol) of N-t-BOC-α-methylalanine according to Procedure A to give an oil which was purified by silica gel chromatography using a gradient of 10%, 20%, 30%, 40% and 50% ethyl acetate in hexane to elute. Recovered 1.32 g of (R)-2-(2-tert-butoxycarbonylamino-2-methyl-propionylamino)-3-(1H-indol-3-ylpropionic acid methyl ester.

C. (R)-2-(2-tert-Butoxycarbonylamino-2-methyl-propionylamino)-3-(1H-indol-3-yl)-propionic Acid To a solution of 1.03 g (2.64 mmol) of 2B in 10 mL of THF was added 381 mg (9.1 mmol) of lithium hydroxide hydrate in 2 mL of water and the mixture was stirred overnight at room temperature. Excess THF was removed by evaporation, and the basic aqueous mixture was extracted three times with ethyl acetate, and then acidified to pH 4 with dilute acetic or hydrochloric acid. The product was extracted with ethyl acetate and the combined organic extracts were washed with brine, dried over $MgSO_4$ and evaporated to give 1.03 g of 2C as an orange foam. MS (Cl, $NH_3$) 390 ($MH^+$). $^1H$ NMR ($CDCl_3$ 300 MHz) δ 7.61 (d, 1H), 7.48 (d, 1H), 7.27 (t, 1H), 7.10 (t, 1H), 4.81 (bs, 1H), 3.35 (m, 1H), 1.49 (s, 6H), 1.32 (s, 9H).

D. {1-[2-[3a-(R,S)-(4-Fluoro-benzyl)-2-methyl-3-oxo-2,3,3a,4,6,7-hexahydro-pyrazolo[4.3-c]pyridin-5-yl]-1-(R)-(1H-indol-3-ylmethyl]-2-oxo-ethycarbamoyl]-1-methyethyl}-carbamic Acid Tert-butyl Ester According to the method outlined in General Procedure A, 193 mg (0.51 mmol) of 1D and 200 mg (0.51 mmol) of 2C were coupled and the residue was purified by silica gel chromatography using an elution gradient of (1:1 v/v ethyl acetate:hexane) to 100% ethyl acetate to give 230 mg of 2D. MS (Cl, NH$_3$) 633 (MH$^+$).

E. 2-Amino-N-[2-[3a-(R,S)-(4-fluoro-benzyl)-2-methyl-3-oxo-2,3,3a,4,6,7-hexahydro-pyrazolo[4,3-c]pyridin-5-yl]-1(R)(1H-indol-3ylmethyl)-2-oxo-ethyl]-isobutyramide hydrochloride To 230 mg (0.36 mmol) of 20 in 10 mL of ethanol was added 4 mL of concentrated HCl and the mixture was stirred at room temperature for about 2 h. The mixture was concentrated and the residue was precipitated from ethanolihexane to give 130 mg of 2E as a white powder. MS (Cl, NH$_3$) 533 (MH$^+$). $^1$HNMR (CD$_3$OD): (partial) δ 7.79 (d, 1 H), 7.48 (m, 1 H), 7.33 (m, 2 H), 7.19–6.77 (m, 7 H), 6.54 (m, 1 H), 5.17 (m, 1 H), 4.02 (m, 1 H, 3.11–2.68 (m, 6 H), 2.47 (m, 2 H), 2.03 (m, 2 H), 1.59 (m, 6 H).

EXAMPLE 3

2-Amino-N-[2-(3a-(R,S)-benzyl-2-methyl-3-oxo-2,3,3a,4,6,7-hexahydro-pyrazolo[4,3-c]pyridin-5-yl)-1R-(1H-indol-3-ylmethyl)-2-oxothyl]-isobutyramide A. 4-Oxo-piperidine-1,3-dicarboxylic acid 1-tert-butyl Ester 3-methyl Ester To a mixture of 7.00 g (36.2 mmol) of 4-oxo-piperidine-3-carboxylic acid methyl ester and 8.82 g (72.3 mmol) of 4,4-dimethylaminopyridine in 200 mL of methylene chloride at about 0° C. was added a solution of 7.88 g (36.2 mmol) of di-tert-butyidicarbonate in 150 mL of methylene chloride over about 30 min. The mixture was warmed to room temperature and then stirred for about 17 h. The mixture was concentrated and the residue was diluted with chloroform and washed three times each with 10% aqueous HCl, saturated aqueous sodium bicarbonate solution and brine, dried over MgSO$_4$ and concentrated to give 9.18 g of a clear yellow oil.

B. 3-(R,S)-Benzyl-4-oxo-piperidine-1,3-dicarboxylic Acid 1-tert-butyl Ester 3-methyl Ester To a solution of 5.00 g (19.4 mmol) 3A in 10 mL of DMF was added 745 mg (7.4 mmol) of sodium hydride (60% oil dispersion) and the mixture was stirred at room temperature for about 15 min. A solution of 3.32 g (19.4 mmol) benzylbromide in 15 mL of DMF was added to the stirring solution by cannula and the mixture was stirred for about 42 h at room temperature. The mixture was diluted with ethyl acetate and washed once with water and four times with brine, dried over MgSO$_4$, and concentrated to give 6.0 g of 3B as a yellow oil. MS (Cl, NH$_3$) 348 (MH$^+$).

C. 3a-(R,S)-Benzyl-2-methyl-3-oxo-2,3,3a,4,6,7-hexahydropyrazolo[4.3-c]-pyridine-5-carboxylic Acid Tert-butyl Ester A mixture of 4.00 g (11.5 mmol) of 3B and 530 mg (11.5 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography using an elution gradient of (15:85 v/v ethyl acetate:hexane) to (75:25 v/v ethyl acetate:hexane) to give 2.6 g of 3C as a clear colorless oil. MS (Cl, NH$_3$) 344 (MH$^+$).

D. 3a-(R,S)-Benzyl-2-methyl-2,3a,4,5,6,7-hexahydropyrazolo[4,3-c]pyridin-3-one

To 2.60 g (7.6 mmol) of 3C was added 20 mL of trifluoroacetic acid at about 0° C. and the mixture was stirred for about 2.5 h. Ethyl acetate was added and the solution was washed with 6N NaOH, dried over MgSO$_4$ and concentrated to give 1.8 g of 3D. MS (Cl, NH$_3$) 244 (MH$^+$).

E. {1-[2-(3a-(R,S)-Benzyl-2-methyl-3-oxo-2,3,3a,4,6,7-hexahydo-pyrazolo[4,3-c]pyridin-5-yl)-1R-(1H-indol-3-ylmethyl)-2-oxoethylcarbamoyl]-1-methyl-ethyl}-carbamic Acid Tert-butyl Ester According to the method outlined in General Procedure A, 125 mg (4.6 mmol) of 3C and 1.75 g (0.51 mmol) of 2C were coupled and the residue was purified by silica gel chromatography using an elution gradient of (6:4 v/v ethyl acetate:hexane) to 7% methanol in ethyl acetate to give 150 mg of 3E.

F. 2-Amino-N-[2-(3a-(R,S)-benzyl-2-methyl-3-oxo-2,3,3a,4,6,7-hexahydro-pyrazolo[4,3-c]pyridin-5-yl)-1R-(1H-indol-3ylmethyl)-2-oxo-ethyl]-isobutyramide Hydrochloride To 150 mg (0.24 mmol) of 3E in 15 mL of ethanol was added 5 mL of concentrated HCl and the mixture was stirred at room temperature for about 3 h. The mixture was concentrated and the residue was crystallized from ethanol/hexane to give 100 mg of 3F. MS (Cl, NH$_3$) 515 (MH$^+$). $^1$HNMR (CD$_3$OD): δ 7.20–6.91 (m, 9 H), 6.56 (m, 1), 5.17 (m, 1 H), 4.05 (m, 1 H), 2.96 (s, 3 H), 2.62 (m, 1H, 2.38 (m, 1H, 2.06 (m, 2 H), 1.61 (m, 8 H).

EXAMPLE 4

2-Amino-N-[2-(3a-(R)-benzyl-2-methyl-3-oxo-2,3,3a,4,6,7-hexahydro-pyrazolo[4.3-c]pyridin-yl)-1-(R)-benzyloxymethy-2-oxo-ethyl]-isobutyramide Hydrochloride and 2-Amino-N-[2-(3a-(S)-benzyl-2-methyl-3-oxo-2,3,3a,4,6,7-hexahydro-pyrazolo[3,4-c]pyridin-5-yl)-1-(R)-benzyloxymethly-2-oxo-ethyk]-isobutyramede Hydrochloride {1-[2-(3a-(R,S)-Benzyl-2-methyl-3-oxo-2,3,3a,4,6,7-hexahydro-pyrazolo[4,3-c]pyridin-5-yl)-1-(R)-benzyloxymethly-2-oxo-ethylcarbamoyl]-1-methyl-ethyl}-carbamic Acid Tert-butyl Ester According to the method outlined in General Procedure A, 1.12 g (4.6 mmol) of 3C and 1.75 g (0.51 mmol) of 1E were coupled to give a mixture of diastereomers. The residue was purified by silica gel chromatography using an elution gradient of (1:1 v/v ethyl acetate:hexane) to 100% ethyl acetate to give 350 mg of less polar 4A isomer 1 and 250 mg of more polar 4A isomer 2. MS (Cl, NH$_3$) 606 (MH$^+$) for both isomers.

B. 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isoblyramide Hydrochloride To 250 mg (0.41 mmol) of 4A isomer 1 in 15 mL of ethanol was added 5 mL of concentrated HCl and the mixture was stirred at room temperature for about 5 h. The mixture was concentrated and the residue was precipitated from ethanol/hexane and dried under vacuum to give 130 mg of 4B isomer 1. MS (Cl, NH$_3$) 506 (MH$^+$). $^1$HNMR (CD$_3$OD): δ 7.33 (m, 5 H), 7.14 (m, 5 H), 5.22 (m, 1 H), 4.57 (m, 3 H), 3.80 (m, 2 H) 3.14 (m, 1 H, 3.04 (s, 3 H), 2.96 (m, 2 H), 2.61 (m, 2 H), 1.63 (m, 7 H).

C. 2-Amino-N-[2-(3a-(S)-benzyl-2-methyl-3oxo-2,3,3a,4,6,7-hexahydro-pyrazolo[4,3-c]pyridin-5-yl-1-(R)-benzyloxymethyl-2oxothy]-isobutyramide Hydrochloride To 250 mg (0.41 mmol) of 4A isomer 2 in 15 mL of ethanol was added 5 mL of concentrated HCl and the mixture was stirred at room temperature for about 5 h. The mixture was concentrated and the residue was precipitated from ethanol/hexane and dried under vacuum to give 120 mg of 4C isomer 2. MS (Cl, NH$_3$) 506 (MH$^+$). $^1$HNMR (CD$_3$OD): δ 7.31 (m, 5 H), 7.13 (m, 5 H), 6.78 (m, 1 H, 5.28 (m, 1 H, 4.62 (m, 3 H), 3.81 (M, 2 H), 3.14 (m,1 H), 2.62 (m, 3 H), 1.58 (m, 7 H).

D. 2-Amino-N-[2-(3a-(R)-beuzyl-2-methyl-3-oxo-2,3,3a,4, 6,7hexahyro-pyrazolo[4,3-c]pyridin-5-yl)-1-(R)-benzyloxymethyl-2-oxo-ethyl]-isobutyramide Methanesulfonate Saturated aqueous sodium bicarbonate was added to 3.60 g (6.6 mmol) of 4B isomer 1 and the mixture was extracted with ethyl acetate. The organic layer was dried over MgSO$_4$ and concentrated. The residue was dissolved in ethyl acetate, cooled to about 0° C. and 0.43 mL (6.6 mmol) of methanesulfonic acid was added and the mixture was stirred for about 0.5 h. Hexane (200 mL) was added to the solution and the mixture was stirred for about lh and filtered to give 3.40 g of a white solid. The solid was recrystallized from 3% aqueous ethyl acetate to give 2.55 g of 4D isomer 1 as a white crystalline solid. MS (Cl, NH$_3$) 506 (MH$^+$).

EXAMPLE 5

2-Amino-N-[1-(3a-(R)-benzyl-2-methyl-3-oxo-2,3, 3a 4,6,7-hexahydro-pyrazolo[4,3-c]pyridine-5-carbonyl)-4-phenyl-(R)-butyl]-isobutyramide Hydrochloride and 2-Amino-N-[1-(3a-(S)-benzyl-2-methyl-3-oxo-2,3,3a,4,6,7-hexahydro-Pyrazolo[4,3-c]pyridine-5-carbonyl)-4-phenyl-(R)-butyl]-isobutyramide Hydrochloride A. 2-Oxo-5,6-diphenyl-3-(3-henylallyl)-morpholine-carboxylic Acid T-butyl Ester To an about −78° C. solution of 13.8 g (70.0 mmol) of cinnamoyl bromide and 4.94 g (14.0 mmol) of t-butyl-(2S, 3R)-(+)-oxo-2,3-diphenyl-4-morpholine carboxylate in 350 mL of anhydrous THF was added 28 mL (28 mmol) of 1M sodium bistrimethylsilylamide in THF. The mixture was stirred at about −78° C. for about 1.5 h and then poured into 750 mL of ethyl acetate. The mixture was washed twice with brine, dried over MgSO$_4$ and concentrated to give a yellow oil. The oil was stirred in 150 mL of hexane overnight and the precipitated solid was then collected by filtration to give 3.2 g of 5A as a white solid.

B. 5(S),6(R)-Diphenyl-3(R)-(3-phenyl-allyl)-morpholin-2-one

To 2.97 g (6.33 mmol) of 5A was added 20 mL of trifluoroacetic acid at about 0° C. and the mixture was stirred for about 2 h and then concentrated. The residue was dissolved in water and basified with aqueous NaOH until a pH of 10 was maintained. The mixture was extracted three times with ethyl acetate and the combined organic extracts were washed with brine, dried over MgSO$_4$ and concentrated to give an orange oil which was purified by silica gel chromatography (10:90 v/v ethyl acetate:hexane) to give 880 mg of 5B as a white solid.

C. 2-(R)-Amino-5-phenyl-pentanoic Acid

A mixture of 440 mg (1.19 mmol) of 5B and 120 mg of palladium chloride in 20 mL of ethanol and 10 mL of THF was hydrogenated at 45 psi. for about 16 h. The mixture was filtered through diatomaceous earth and concentrated, and the residue was triturated with ether to give 240 mg of 5C as a white solid.

D. 2-tert-Butoxycarbonylamino-2-methyl-propionic acid 2,5-dioxo-pyrrolidin-1-yl Ester To a slurry of 5.0 g (24.6 mmol) of N-t-BOC-α-methylalanine in 13.5 mL of methylene chloride was added 3.40 g (29.6 mmol) of N-hydroxysuccinimide and 5.65 g (29.6 mmol) of EDC. The slurry was stirred for about 17 h at room temperature. The mixture was diluted with ethyl acetate and washed twice each with water, saturated sodium bicarbonate solution and brine. Dried over MgSO$_4$ and concentrated. The product was purified by silica gel chromatography (1:1 v/v ethyl acetate:hexanes) to give 5.2 g of the title compound of this part D as a white solid.

E. (R)-2-(2-tert-Butoxyrarbonylamino-2-methylpropionylamino)-5-phenyl-pentanoic Acid A mixture of 203 mg (1.05 mmol) of 5D, 378 mg (1.26 mmol) of 5C and 434 mg (3.36 mmol) of diisopropylethylamine in 2 mL of DMF was stirred over-night. The mixture was diluted with ethyl acetate and extracted twice with 1N HCl. The aqueous phase was extracted once with ethyl acetate. The pooled organic extracts were washed three times with water and once with brine. The mixture was dried over MgSO$_4$ and concentrated. The residue was purified by silica gel chromatography using 80% chloroform in hexane followed by 100% chloroform followed by 10% methanol in chloroform to give 127 mg of 5E.

F. {1-[1-(3a-(R,S)-Benzyl-2-methyl-3-oxo-2,3,3a,4,6,7-hexahydro-pyrazolo[4,3-c]pyridine-5-carbonyl)-4-phenyl-(R)-butylcarbamoyl]-1-methyl-ethyl}-carbamic Acid Tert-butyl Ester According to the method outlined in General Procedure A, 130 mg (0.53 mmol) of 3C and 200 mg (0.53 mmol) of 5E were coupled to give a mixture of diastereomers. The residue was purified by silica gel chromatography using an elution gradient of (1:1 v/v ethyl acetate:hexane) to 100% ethyl acetate to give 40 mg of less polar 5F isomer 1 and 40 mg of more polar 5F isomer 2. MS (Cl, NH$_3$) 604 (MH$^+$) for both isomers.

G. 2-Amino-N-[1-(3a-(R)-benzyl-2-methyl-3-oxo-2.3,3a,4, 6,7-hexahydro-pyrazolo[4,3-c]pyridine-carbonyl)-4-phenyl-(R)-butyl]-isobutyramide Hydrochloride To 40 mg (0.07 mmol) of 5F isomer 1 in 10 mL of ethanol was added 4 mL of concentrated HCl and the mixture was stirred at room temperature for about 4 h. The mixture was concentrated and the residue was precipitated from methylene chloride/hexane and dried under vacuum to give 30 mg of 5G isomer 1. MS (Cl, NH$_3$) 504 (MH$^+$). $^1$HNMR (CD$_3$OD): (partial) δ 7.19 (m, 10 H), 4.37 (m, 1 H), 3.02 (m, 6 H), 2.67 (m, 4 H), 1.83 (m, 4 H), 1.62 (s, 6 H), 1.28 (m, 1 H).

H. 2-Amino-N-[1-(3a-(S)-benzyl-2-methyl-3oxo-2,3,3a,4,6, 7-hexahydro-pyrazolo[4.3c]pyridine-5-carbonyl)-4-phenyl-(R)-butyl]-isobutyramide Hydrochloride To 40 mg (0.07 mmol) of 5F isomer 2 in 10 mL of ethanol was added 4 mL of concentrated HCl and the mixture was stirred at room temperature for about 4 h. The mixture was concentrated and the residue was precipitated from methylene chloridelhexane and dried under vacuum to give 30 mg of 6H isomer 2. MS (Cl, NH$_3$) 504 (MH$^+$). $^1$HNMR (CD$_3$OD): (partial) 7.25 (m, 9 H), 6.88 (m, 1 H, 3.04 (s, 3 H), 2,71 (m, 4 H), 2.48 (m, 2 H), 1.75 (m, 4 H), 1.62 (m, 6 H), 1.28 (m, 1 H.

EXAMPLE 6

2-Amino-N-[2-(3a-(R,S)-benzyl-2-methyl-3-oxo-2,3,3a,4, 6,7-hexahydro-pyrazolo[4,3-c]pyridin-5-yl)-1-(R)-benzyloxymethyl-2-oxo-ethyl]-isobutyramide Hydrochloride A. {1-[2-(3a-(R,S)-Benzy-2-methyl-3-oxo-2,3,3a,4,6,7-hexahydro-pyrazolo[4,3-c]pyridin-5-yl)-1-(R)-benzyloxymethyl-2-oxo-ethylcarbamoy]-1-methyl-ethyl}-carbamic Acid Tert-butyl Ester According to the method outlined in General Procedure A, 200 mg (0.82 mmol) of 3C and 320 mg (0.82 mmol) of 1E were coupled to give a mixture of diastereomers. The residue was purified by silica gel chromatography using an elution gradient of (1:1 v/v ethyl acetate:hexane) to 10% methanol in ethyl acetate to give 170 mg of 6A.

B. 2-Amino-N-[2-(3a-(R,S)-benzyl-2-methyl-3-oxo-2,3,3a, 4,6,7-hexahydro-pyrazolo[4.3-c]pyridin-5-yl)-1-(R)-benzyloxymethyl-2-oxo-ethyl]isobutyramide Hydrochloride To 170 mg (0.28 mmol of 6A in 20 mL of ethanol was added 5 mL of concentrated HCl and the mixture was stirred at room temperature for about 2.5 h. The mixture was concentrated and the residue was precipitated from ethanol/hexane to give 70 mg of 6B. MS (Cl, NH$_3$) 506 (MH$^+$). $^1$HNMR (CD$_3$OD): δ 7.32 (m, 5 H); 7.16 (m, 5 H), 5.22 (m, 1 H, 4.67 (m, 1 H), 4.55 (m, 2 H), 3.79 m, 2 H), 3.12 (m, 2 H), 3.00 (m, 6 H), 2.71 (m, 3 H), 1.56 (m, 8 H).

EXAMPLE 7

2-Amino-N-[2-(3a-benzyl-2-ethyl-3-oxo-2,3,3a,4,6,7-hexahydro-pyrazolo[4,3-c]pyridin-5-yl)-1-(1H-indol-3-ylmethyl)-2-oxo-ethyl]-isobutyramide Hydrochloride A. 3a-(R,S)-Benzyl-2-ethyl-3-oxo-2,3,3a,4,6,7-hexahydro-pyrazolo[4.3-c]pyridine-5-carboxylic Acid Tert-butyl Ester To 555 mg (1.60 mmol) of 3B in 27 mL of ethanol was added 240 mg (1.60 mmol) of ethylhydrazineoxalate and the mixture was heated at reflux for about 4 h. The mixture was concentrated and the residue was purified by silica gel chromatography using an elution gradient of (10:1 v/v hexane:ethyl acetate) to (3:7 v/v hexane:ethyl acetate) to give 357 mg of 7A. MS (Cl, NH$_3$) 358 (MH$^+$).

B. 3a-(R,S)-Benzyl-2-ethyl-2,3a,4,5,6,7-hexahydro-pyrazolo[4,3-c]pyridin-3-one

To 350 mg (0.98 mmol) of 7A in 3 mL of ethanol was added 1.5 mL of concentrated HCl and the mixture was stirred at room temperature for about 2 h. The mixture was concentrated to give 257 mg of 7B. MS (Cl, NH$_3$) 258 (MH$^+$).

C. {1-[2-(3a-(R,S)-Benzyl-2-ethyl-3-oxo-2,3,3a,4,6,7-hexahydropyrazolo[4,3-c]pyridin-5-yl)-1-(R)-(1H-indol-3-ylmethyl)-2-axo-ethylcarbamoyl]-1-methyl-ethyl}-carbamic Acid Tert-butyl Ester According to the method outlined in General Procedure A, 82 mg (0.28 mmol) of 7B and 100 mg (0.26 mmol) of 2C were coupled and the residue was purified by silica gel chromatography using an elution gradient of 100% methylene chloride to 2% methanol in methylene chloride to give 110 mg of 7C. MS (Cl, NH$_3$) 629 (MH$^+$).

D. 2-Amino-N-[2-(3a-(R,S)-benzyl-2-ethyl-3-oxo-2,3,3a,4, 6,7-hexahydro-pyrazolo[4,3-c]pyridin-5-yl)-5-(R)-(1 Hndolylmethyn-2-oxo-ethyl]-isobutyramide Hydrochloride To 100 mg (0.15 mmol) of 7C in 2 mL of ethanol was added 1 mL of concentrated HCl and the mixture was stirred at room temperature for about 2 h. The mixture was concentrated to give 72 mg of 7D as a colorless foam. MS (Cl, NH$_3$) 529 (MH$^+$).

EXAMPLE 8

2-Amino-N-[2-(3a-(R)-benzyl-2ethyl-3-oxo-2,3,3a, 4,6,7-hexahydro-pyrazolo[4,3-c]pyridin-5-yl)-1-(R)-benzyloxymethyl-2-oxo-ethyl]-isobutyramide Hydrochloride and 2-Amino-N-[2-(3a-(S)benzyl-2-ethyl-3-oxo-2,3,3a,4,6,7-hexahydro-pyrazolo[4,3-c]pyridin-5-yl)-1-(R)-benzyloxymethyl-2-oxyethyl]-isobutyramide Hydrochloride A. {1-[2-(3a-Benzyl-2-ethyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic Acid Tert-butyl Ester According to the method outlined in General Procedure A, 85 mg (0.29 mmol) of 7B and 100 mg (0.26 mmol) of 1E were coupled to give a mixture of diastereomers. The residue was purified by silica gel chromatography using an elution gradient of 100% methylene chloride to 2% methanol in methylene chloride to give 6 mg of less polar 8A isomer 1 and 11 mg of more polar 8A isomer 2. MS (Cl, NH$_3$) 620 (MH$^+$) for both isomers.

B. 2-Amino-N-[2-(3a-(R)-benzyl-2-ethyl-3-oxo-2,3,3a,4,6, 7-hexahydro-pyrazolo[4,3-c]pyridin-5y)-1-(R)-benzyloxymethyl-2-oxo-ethyl]-isobutyramide Hydrochloride To 5.7 mg (0.009 mmol) of 8A isomer 1 in 1 mL of ethanol was added 0.4 mL of concentrated HCl and the mixture was stirred at room temperature for about 3 h. The mixture was concentrated to give 4.7 mg of 8B isomer 1. MS (Cl, NH$_3$) 520 (MH$^+$). $^1$HNMR (CD$_3$OD): (partial) δ 7.41–7.05 (m, 10 H), 5.20 (m, 1 H), 4.61 (m, 1 H), 4.52 (s, 2 H), 3.71 (m, 1 H, 3.60 (m, 1 H), 2.61 (m, 3 H), 1.39 (m, 9 H).

C. 2-Amino-N-[2-(3a-(S)-benzy-2-ethyl-3-oxo-2,3,3a,4,6, 7-hexahydro-pyrazolo[4,3-c]pyridin-5-yl)-1-(R)-benzyloxymethyl-2-oxo-ethyl]-isobutyramide Hydrohloride To 10 mg (0.016 mmol) of 8A isomer 2 in 1 mL of ethanol was added 0.4 mL of concentrated HCl and the mixture was stirred at room temperature for about 3 h. The mixture was concentrated to give 8 mg of 8C isomer 2. MS (Cl, NH$_3$) 520 (MH$^+$). $^1$HNMR (CD$_3$OD): (partial) δ 7.43–7.00 (m, 10 H), 6.81 (m, 1 H, 5.32 (m, 1 H), 4.63 (m, 2 H), 4.53 (m, 1 H), 3.72 (m, 1 H, 1.37 (m, 9 H).

EXAMPLE 9

2-Amino-N-[2-(2-benzyl-3-oxo-2,3,3a,4,6,7-hexahydro-pyrazolo[4,3-c]pridin-5-yl)-1-(R)-benzyloxymethyl-2-oxo-ethyl]-isobutyramide Hydrochloride A. 2-Benzyl-3-hydroxy-2,4,6,7-tetrahydro-pyrazolo[4,3-c] yridine-5carboxylic Acid Tert-butyl Ester A mixture of 800 mg (3.11 mmol) of 3B and 495 mg (3.11 mmol) of benzylhydrazine dihydrochloride and 423 mg (3.11 mmol) of sodium acetate trihydrate in 15 mL of ethanol was heated at reflux for about 17 h. The mixture was concentrated and the residue was dissolved in 100 mL of toluene and heated at reflux for about 48 h. The mixture was diluted with ethyl acetate and washed with brine, dried over MgSO$_4$ and concentrated and the residue was purified by silica gel chromatography using 100% ethyl acetate followed by 5% methanol in methylene chloride to give 530 mg of 9A as a light brown solid. MS (Cl, NH$_3$) 330 (MH$^+$).

B. 2-Benzyl-4,5,6,7-tetrahydro-2H-pyrazolo[4,3-c]pyridin-3-ol

To 411 mg (1.24 mmol) of 3E in 30 mL of ethanol was added 10 mL of concentrated HCl and the mixture was stirred at room temperature for about 30 min. The mixture was concentrated and the residue was crystallized from methanovethyl acetate to give 353 mg of 98. MS (Cl, NH$_3$) 230 (MH$^+$).

C. {1-[2-(2-Benzyl-3-hydroxy-2,4,6,7-tetrahydro-pyrazolo [4,3-c]pyridin-5-yl)-1-R-benzyloxymethyl-2-oxo-ethylcarbamoy]-1-meth-ethyl}-carbamic Acid Tert-butyl According to the method outlined in General Procedure A, 100 mg (0.38 mmol) of 9B and 145 mg (0.38 mmol) of 1E were coupled and the residue was purified by silica gel chromatography (95:5 v/v methanol:methylene chloride) to give 42 mg of 9C as a white solid. MS (Cl, NH$_3$) 592 (MH$^+$).

D. 2-Amino-N-[2-(2-benzl-3-oxo-2,3a-4,6,7-hexahydro-pyrazolo[4,3-c]pridin-5-yl)-(R)-benzylogyethyl-2-oxo-ethyl]-isormide Hydrochloride To 42 mg (0.07 mmol) of 90 in 20 mL of ethanol was added 6 mL of concentrated HCl and the mixture was stirred at room temperature for about 30 min. The mixture was diluted with ethanol concentrated and the residue was precipitated from methanol/ethyl acetate to give 35 mg of 9D as a white solid. MS (Cl, NH$_3$) 492 (MH$^+$). $^1$HNMR (CD$_3$OD): (partial) 7.41–7.16 (m, 10 H), 5.19 (m, 3 H), 4.48 (m, 4 H), 3.88 (m, 1 H, 3.74 (m, 2 H), 2.68 (m, 2 H), 1.58 (m, 6 H).

EXAMPLE 10

2-Amino-N-{2-[3a-(R)-benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo-ethyl}-isobutyramide Hydrochloride and 2-Amino-N-{2-[3a-(S)-benzyl-3-oxo-2-(2,2,2-trifluoro-ethyl)-2,3,3a,4,6,7-hexahydro-pyrazolo[4,3-c]pyridin-5yl]-1-(R)-benzyloxymethyl-2-oxo-ethyl}-isobutyramide Hydrochloride A. 3a-(R,S)-Benzyl-3-oxo-2-(2.2.2-trifluoro-ethyl)-2,3,3a,4,6,7-hexahydro-pyrazolo[4,3-c]pyridine-5-carboxylic Acid Tert-butyl Ester A mixture of 840 mg (2.42 mmol) of 3B and 276 mg (2.42 mmol) of 2,2,2-trifluoroethylhydrazine (70% in water) in 20 mL of ethanol was heated at reflux for about 5 h and then concentrated. The residue was dissolved in 40 mL of toluene and heated at reflux for about 17 h. The mixture was concentrated and the residue was purified by silica gel chromatography (9:1 v/v hexane:ethyl acetate) to give 703 mg of 10A as a yellow oil. MS (Cl, NH$_3$) 412 (MH$^+$).

B. 3a-(R,S)-Benzyl-2-(2,2,2-triuoroethyl)-2,3a,4,5,6,7-hexahydro-pyrazol[4,3-ci]pyridin-3one To 600 mg (1.46 mmol) of 10A at about 0° C. was added 3 mL of cold trifluoroacetic acid and the mixture was stirred for about 3 h, allowing the solution to reach room temperature as it did so. The mixture was concentrated and the residue was dissolved in water and the solution was basified to pH 11 with 5N NaOH and then saturated with potassium carbonate. The solution was extracted three times with ethyl acetate and the combined organic extracts were washed with brne, dried over MgSO$_4$ and concentrated to give 345 mg of 10B as an opaque oil. MS (Cl, NH$_3$) 312 (MH$^+$).

C. (1-{2-[3a-(R,S)-Bezyl-3-oxo-2-(2,2,2-trifluoro-ethyl)-2,3,3a,4,6,7-hexahydro-pyrazolo[4,3-c]pyridin-yl]-1-(R)-benzyloxymethyl-2-oxo-ethylcarbamoyl}-1-methyl-metyl)-carbamic Acid Tertul Ester According to the method outlined In General Procedure A, 137 mg (0.44 mmol) of 10B and 167 mg (0.44 mmol) of 1E were coupled to give a mixture of diastereomers. The residue was purified by silica gel chromatography using an elution gradient 100% methylene chloride to 5% methanol in methylene chloride to give 128 mg of less polar 10C isomer 1 and 63 mg of more polar 10C isomer 2. MS (Cl, NH$_3$) 674 (MH$^+$) for both isomers D. 2-Amino-N-{2-[3a-(R)-benzyl-3-oxo-2-(2,2,2-trifluoro-ethyl)-2,3,3a,4,6,7-hexahydro-oyrazolo[4,3-c]pyridin-5-yl]-1-(R)-benzyloxymethyl-2-oxothy}-isobutyramide Hydrochloride To 120 mg (0.18 mmol) of 10C isomer 1 in 3.5 mL of ethanol was added 1.5 mL of concentrated HCl and the mixture was stirred at room temperature for about 2 h. The mixture was concentrated to give 94 mg of 10D isomer 1 as an off-white powder. MS (Cl, NH$_3$) 574 (MH$^+$). $^1$HNMR (CD$_3$OD): (partial) 6 7.31 (m, 5 H), 7.18 (m, 5 H), 5.21 (m, 1 H), 4.57 (m, 3 H), 4.26 (m, 1H, 4.08 (m, 1 H), 3.79 (m, 2 H) 3.09 (m. 4 H), 2.65 (m, 2 H), 1.63 (m, 6 H).

E. 2-Ammno-N-{2-[3a-(S)-benzyl-3-oxo-2-(2.2.2-trifluoroethyl)-2,3,3a,4,6,7-hexahydro-pyrozolo[4,3-c]pyridin-5-yl]-1-(R)-benzyloxymethyl-2-axo-ethy}-isobutyramide Hydrochloride To 53 mg (0.079 mmol) of 10C isomer 2 in 3.5 mL of ethanol was added 1.5 mL of concentrated HCl and the mixture was stirred at room temperature for about 2 h. The mixture was concentrated to give 41 mg of 10E isomer 2 as a light yellow solid. MS (Cl, NH$_3$) 574 (MH$^+$). $^1$HNMR (CD$_3$OD): (partial) 6 7.33 (m, 5 H), 7.15 (m, 4 H), 6.81 (m, 1 H), 5.30 (m, 1 H), 4.67 (m, 4 H), 4.15 (m, 2 H), 3.77 (m, 2 H), 3.09 (m, 3 H), 2.64 (m, 3 H), 1.58 (m, 6 H).

Example 11

2-Amino-N-[2-(3a-(R)-benzyl-2-tert-butyl-oxo-2,3,3a,4,6,7-hexahydro-pyrzolo[4,3-c]pyridin-5-yl)-1-(R)-benzyloxymethyl-2-oxo-ethyl]-isobutyramide Methanesulfonate and 2-Amino-N-[2-(3a(S)-benzyl-2-tert-butyl-3-oxo-23.33a,4 .6.7-hexahydro-pyrazolo [4,3-c]pyridin-5-yl)1-(R)-benzyloxymethyl-2-oxo-ethyl-isobutyramide methanesulfonate 3a-(R,S)-Benzy-2-tert-butyl-3-oxo-2,3,3a,4,6,7-hexahydropyrazolo[4,3-c]pyridine-5-carboxylic Acid Tert-butyl Ester To 2.07 g (5.95 mmol) of 14B in 40 mL of ethanol was added 0.97 g (7.7 mmol) of tert-butylhydrazine hydrochloride and 0.63 g (7.7 mmol) of sodium acetate and the mixture was heated at about 70° C. for about 17 h. The mixture was cooled and the solution decanted from the precipitate and concentrated. The residue was dissolved in 80 mL of toluene and heated at reflux for about 6 h. The mixture was concentrated and the residue was purified by silica gel chromatography (9:1 v/v hexane:ethyl acetate) to give 1.7 g of 11A. MS (Cl, NH$_3$) 386 (MH$^+$).

B. 3a-(R,S)-Benzyl-2-tert-butyl-2,3a,4,5,6,7-hexahydro-pyrazolo[4,3-c]pyridin-3-one To 535 mg (1.39 mmol) of 11A in 20 mL of methylene chloride was added 225 μL of methanesulfonic acid and the mixture was stirred for about 1.5 h at room temperature. The mixture was diluted with ethyl acetate and washed twice with 1N NaOH and once with brine, dried over Na$_2$SO$_4$ and concentrated to give 246 mg of 11B. MS (Cl, NH$_3$) 286 (MH$^+$).

C. {1-[2-(3a-(R,S)-Benzyl-2-tert-butyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic Acid Tert-butyl Ester According to the method outlined in General Procedure A, 246 mg (0.86 mmol) of 11 B and 328 mg of 14F were coupled to give a mixture of diastereomers. The residue was purified by silica gel chromatography (6:4 v/v hexane/ethyl acetate) to give 250 mg of less polar 11C isomer 1 and 90 mg more polar 11C isomer 2. MS (Cl, NH$_3$) 648 (MH$^+$) for both isomers.

D. 2-Amino-N-[2-(3a-(R)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide Methanesulfonate To 210 mg (0.32 mmol) of 11C isomer 1 in 15 mL of methylene chloride at about 0° C. was added 28 μL (0.44 mmol) of methanesulfonic acid. The ice bath was removed and the mixture was stirred for about 3 h, diluted with 15 mL of diethyl ether and the precipitated solid was collected by filtration to give 100 mg of 11D isomer 1. MS (Cl, NH$_3$) 548 (MH$^+$). $^1$H NMR (CD$_3$OD): (partial) δ 7.33 (m, 5 H), 7.27–7.07 (m, 5 H), 5.21 (m, 1 H), 4.54 (m, 3 H), 3.86 (m, 3 H), 3.10 (m, 4 H), 2.61 (s, 3 H) 1.62 (m, 6 H), 1.18 (s, 9 H).

E. 2-Amino-N-[2-(3a-(S)-benzyl-2-tert-butyl-3-oxo-2,3,3a, 4,6,7-hexahydro-pyrazolo[4,3-c]pyridin-5-yl)-1-(R)-benzyloxymethyl-2-oxo-ethyl]-isobutyramide Methanesulfonate To 85 mg (0.13 mmol) of 11C isomer 2 in 10 mL of methylene chloride at about 0° C. was added 21 μL (0.32 mmol) of methanesulfonic acid. The ice bath was removed and the mixture was stirred for about 3 h, diluted with 20 mL of diethyl ether and the precipitated solid was collected by filtration to give 46 mg of 11E isomer 2. MS (Cl, NH$_3$) 548 (MH$^+$). $^1$H NMR (CD$_3$OD): (partial) δ 8.28 (br d, 1 H), 7.32 (m, 5 H), 7.18 (m, 4 H), 6.84 (m, 1 H), 5.31 (m, 1 H), 4.60 (m, 3 H), 3.70 (m, 3 H), 3.18–2.92 (m, 3 H), 2.68 (s, 3 H), 1.57 (m, 6 H), 1.13 (s, 9 H).

EXAMPLE 12

2-Amino-N-[1-(R)-(1H-indol-3-ylmethyl)-2-(2-methyl-3-oxo-3a4-(R,S)-pyridin-2-ylmethyl-2,3,3a,4,6,7-hexahydro-pyrazolo[4,3-c]pyridin-5yl)-2-oxo-ethyl]-isobutyramide Dihydrochloride A. 4-Oxo-3-(R,S)-pyridin-2-ylmethyl-piperidine-1.3-dicarboxylic Acid 1-tert-buty Ester 3-methyl Ester To a solution of 2.00 g (7.8 mmol) of 3A in 32 mL of THF was added 468 mg (11.7 mmol) of sodium hydride (60% oil dispersion) at about 0° C. and the mixture was stirred for about 30 min. A solution of 762 mg (6.0 mmol) 2-picolyl chloride in 5 mL of THF was added to the stirring solution over about 5 min, followed by the addition of 432 mg (2.6 mmol) of potassium iodide. The ice bath was removed and the mixture was heated for about 17 h at reflux. The mixture was diluted with ethyl acetate and washed once with water and once with brine, dried over MgSO$_4$, and concentrated. The residue was purified by silica gel chromatography using (6:4 v/v ether/hexane) followed by (6:4 v/v ethyl acetate:hexane) to give 1.2 gof 12A. MS (Cl, NH$_3$) 349 (MH$^+$).

B. 2-Methyl-3-oxo-3a-(RS)-pyridin-2-ylmethyl-2,3,3a,4,6,7-hexahydro-pyrzolo[4,3-c]pyridine-5-carboxylic Acid Tert-buty Ester A mixture of 1.20 g (3.45 mmol) of 12A and 159 mg (3.45 mmol) of methylhydrazine in 20 mL of ethanol was heated at reflux for about 6.5 h. The mixture was concentrated and the residue was dissolved in 25 mL toluene and heated at reflux for about 17 h. The mixture was concentrated and the residue was purified by silica gel chromatography (65:35 v/v ethyl acetate:hexane) to give 450 mg of 12B. MS (Cl, NH$_3$) 345 (MH$^+$).

C. 2-Methyl-3a-(R,S)-pyridin-2-ylmethyl-2,3a,4. 5.6.7-hexahydro-pyrazolo[4,3-c]pyridin-3-one Dihydrochloride A mixture of 450 mg (1.30 mmol) of 12B in 2 mL of 4M HClIdioxane was stirred at room temperature for about 4.5 h. The mixture was concentrated to give 450 mg of 12C. MS (Cl, NH$_3$) 245 (MH$^+$).

D. {1-[1-(1-(R)-H-Indol-3-ylmethyl)-2-(2-methyl-3-oxo-3a-(R,S)-pyridin-2-ylmethyl-2,3,3a,4,6,7-hexahydro-pyrazolo[4,3-c]pyrdin-5-yl)-2-oxo-ethylcatbamoy]-1-methylethyl}-carbamic Acid Tert-butyl Ester According to General Procedure A, 108 mg (0.31 mmol) of 12C and 122 mg (0.31 mmol) of 2C were coupled and the residue was purified by silica gel chromatography (95:5 v/v ethyl acetate:methanol) to give 118 mg of 12D. MS (Cl, NH$_3$) 616 (MH$^+$).

E. 2-Amino-N-[1-(R)-(1H-indol-3-ylmethyl)-2-(2-methyl-3-oxo-3a-(R,S)-pyridin-2-ylmethyl-2,3,3a,4,6,7-hexahydro-pyrazolol4,3-clgaridin-5-yl)-2-oxo-ethy]-isobutyamide Dihydrochloride A mixture of 110 mg (0.18 mmol) of 12D in 1 mL of 4M HCl/dioxane was stirred at room temperature for 17 h. The mixture was concentrated to give 51 mg of 12E. MS (Cl, NH$_3$) 516 (MH$^+$). $^1$HNMR (CD$_3$OD): (partial) 8 8.91–8.52 (m, 2 H), 8.04 (m, 2 H), 7.76–7.50 (m, 3 H), 6.82 (m, 1 H), 4.62 (m, 1 H, 3.36 (s, 3 H), 1.63 (s, 6 H).

EXAMPLE 13

2-Amino-N-[1-(R)-benzyloxymethy-2-(2-methyl-3-oxo-3a-(R,S)-pyridin-2-ylmethyl-2,3a,4,6, 7hexahydro-pyrazolo[4,3-c]pyridin-2-oxo-ethyl]-isobutyramide Dihydrochloride A. {1-[1-(R)-Benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethy]-carbamoyl]-1-methyl-ethyl}-carbamic Acid Tert-butyl Ester According to General Procedure A, 86 mg (0.27 mmol) of 12C and 103 mg (0.27 mmol) of 1E were coupled and the residue was purified by silica gel chromatography (95:5 v/v ethyl acetate:hexane) to give 82 mg of 13A.

B. 2-Amino-N-[1-(R)-benzyloxymethyl-2-(2-methyl-3-oxo-3a-(R,S)-pyridin-2-ylmethyl-2.3.3a,4,6,7-hexahydro-pyrazolo[4,3-c]pyridin-5-yl)-2-oxo-ethyl]-sobutyramide Dihydrochloride A mixture of 75 mg (0.12 mmol) of 13A in 1 mL of 4M HCl/dioxane was stirred at room temperature for about 17 h. The mixture was concentrated to give 80 mg of 13B. MS (Cl, NH$_3$) 507 (MH$^+$). $^1$HNMR (CD$_3$OD): (partial) 5 8.78 (m, 1 H), 8.46 (m, 1 H), 8.13–7.82 (m, 2 H), 7.32 (m, 5 H), 4.57 (m, 3 H), 3.96 (m, 1 H), 3.82 (m, 2 H), 1.63 (m, 6 H).

EXAMPLE 14

2-Amino-N-[2-(3a-(R)-benzyl-2-methyl-3-oxo-2,3, 3a,4,6,7-hexahydro-pyrazolo[4,3-c]pyridin-5-yl)-1-(R)-benzyloxymethyl-2-oxo-ethyl]-isobutyramide.

4-Oxo-piperidine-1,3-dicarboxylic Acid 1-tert-butyl Ester 3-methyl Ester

To a mixture of 100.0 g (516.4 mmol) of 4-oxo-piperidine-3-carboxylic add methyl ester and 63 g (516.4 mmol) of 4,4-dimethylaminopyridine in 1 L of methylene chloride at about 0° C. was added a solution of 113.0 g (516.4 mmol) of di-tert-butyidicarbonate in 100 mL of methylene chloride over about 90 min. The mixture was slowly warmed to room temperature and then stirred for about 19 h. The mixture was washed three times each with 10% aqueous HCl, saturated aqueous sodium bicarbonate solution and brine, dried over MgSO$_4$ and concentrated to give 130.5 g of 14A as an amorphous solid. $^1$HNMR (CDCl$_3$): δ 4.03 (br, 2H); 3.74 (s, 3H), 3.56 (t, 2H), 2.36 (t, 2H), 1.42 (s, 9H).

B. 3-(R)-Benzyl-4-oxo-piperidine-1,3-dicarboxylic Acid 1-tert-butyl Ester 3-methyl Ester To a stirred suspension of 11.7 g (293 mmol) of sodium hydride (60% oil dispersion washed twice with 100 mL of hexane) in 100 mL of DMF was added a solution of 65.4 g (254 mmol) of 14A in 150 mL of DMF at about 0° C. over about 45 min. The ice bath was removed and the mixture was stirred at room temperature for about 45 min. The mixture was recooled to about 0° C. and 35.2 mL (296 mmol) of benzylbromide in 200 mL of DMF was added dropwise to the stirring solution and the mixture was stirred for about 23 h at room temperature. To the solution was carefully added 550 mL of water and the mixture was stirred for about 30 min. The mixture was extracted three times with ethyl acetate and the combined organic extracts were washed five times with water, once with brine, dried over MgSO$_4$ and concentrated to give 98 g of a yellow oil. The oil was crystallized from hexane to give 71 g of 14B as a white solid. MS (Cl, NH$_3$) 348 (MH$^+$). $^1$HNMR (CDCl$_3$): (partial) δ 7.23 (m, 3 H), 7.13 (m, 2 H), 4.58 (br m, 1 H), 4.18 (br, 1 H), 3.63 (s, 3 H), 3.28–2.96 (m, 4 H), 2.72 (m, 1 H), 2.43 (m, 1 H), 1.44 (s, 9 H).

C. 3a-(R)-Benzyl-2-methyl-3-oxo-2,3,3a,4,6,7-hexahydro-pyrazolo[4,3-c]pyridine-5-carboxylic acid Tert-butyl Ester A mixture of 47.0 g (135 mmol) of 14B, 38.9 g (270 mmol) of methylhydrazine sulfate and 44,3 g (540 mmol) of sodium acetate in 900 mL of ethanol was heated at reflux for about 17 h under nitrogen. The mixture was concentrated and the residue was dissolved in ethyl acetate and washed three times with water and once with brine, dried over $MgSO_4$ and concentrated to give a yellow oil. The oil was stirred in 750 mL of hexane for about 3 h to give 41.17 g of 14C as a white solid. MS (Cl, $NH_3$) 344 ($MH^+$). $^1HNMR$ ($CDCl_3$): (partial) δ 7.19 (m, 3 H), 7.05 (m, 2 H), 4.61 (br m, 2 H), 3.24 (m, 1 H, 3.09 (s, 3 H), 3.01 (m, 1 H, 2.62 (m, 4 H), 1.52 (s, 9 H).

D. 3a-(RS)-Benzyl-2-methyl-2,3a,4,5,6,7-hexahydropyrazolo[4,3-c]pyridin-3-one Hydrochloride Anhydrous HCl was bubbled through a solution of 24.55 g (71.5 mmol) of 14C in 800 mL of diethyl ether at about 0° C. for about 12 min. The mixture was stirred for about 3 h, during which time a white precipitate formed. The precipitated solid was collected by filtration and to give 19.2 9 of 14D. MS (Cl, $NH_3$) 244 ($MH^+$). $^1HNMR$ ($CD_3OD$): (partial) δ 7.25 (m, 3 H), 7.05 (m, 2 H), 3.77 (m, 2 H), 3.51 (d, 1 H, 3.25 (m, 1 H, 3.17 (m, 3 H), 3.03 (8, 3 H), 2.81 (m, 1H.

E. 2-tert-Butoxycarbonylamino-2-methyl-propionic Acid 2.5-dioxopyrrolidin-1-yl Ester To a stirring solution of 100.0 g (492 mmol) of Boca-methylaianine and 94.0 g (492 mmol) of EDC in 2 L of methylene chloride at about 0° C. was added 56.63 g (492 mmol) of N-hydroxysuccinimide in portions and the reaction was then allowed to warm to room temperature. The mixture was stirred for about 24 h and washed twice each with saturated aqueous sodium bicarbonate solution and brine, dried over $Na_2SO_4$ and concentrated to give 124.0 g of 14E as a white solid. $^1HNMR$ ($CDCl_3$): δ 4.96 (br, 1 H), 2.82 (s, 4H), 1.66 (s, 6H), 1.48 (s, 9H).

F. 3-(R)-Benzyloxy-2-(2-tert-butoxycarbonylamino-2-methyl-propionylamino)-propionic Acid A mixture of 50.5 g (168 mmol) of 14E, 33.5 g (168 mmol) of O-benzyl-D-serine, and 51.05 g (505 mmol) of triethylamine in 400 mL of dioxane and 100 mL of water was heated at about 45° C. for about 16 h. The mixture was diluted with ethyl acetate and acidified to pH 2 with acetic acid. The layers were separated and the organic phase was washed with brine, dried over $Na_2SO_4$ and concentrated to give 650 g of 14F as a white solid. $^1HNMR$ ($CD_3OD$): (partial) δ 7.55 (d, 1 H, 7.29 (m, 5 H). 4.52 (m, 1 H, 4.48 (s, 2 H), 3.84 (d of d, 1 H, 3.69 (d of d, 1 H, 1.42 (s, 6 H), 1.38 (s, 9 H).

G. 3a-(R)-Benzyl-2-2,3a,4,5,6,7-hexahydro-pyazolo[4.3-c]pyrdin-3-one L-tartrate

To a mixture of 5.00 g(20.6 mmol) of the free base of 14D and 3.09 g (20.6 mmol) of L-tartaric acid in 80 mL of acetone and 3.2 mL of water was heated under nitrogen at about 70° C. for about 70 h, during which time the reaction mixture became a thick suspension and an additional 20 mL of acetone was added. The reaction mixture was cooled slowly to room temperature and then filtered. The solid that was collected was washed with acetone and dried under vacuum to give 7.03 g of 14G as a white solid.

H. 3a-(R)-Benzyl-2-methyl-2,3a,4,5,6,7-hexahydro-pyrazolo[4,3-c]pyridin-3one

To a suspension of 5.00 g (12.7 mmol) of 14G in 80 mL of methylene chloride at about 0° C. was added 1.72 mL (25.4 mmol) of ammonium hydroxide and the mixture was stirred for about 15 min. The cold solution was filtered and used immediately in the next step.

I. {1-[2-(3a-(R)-Benzyl-2-methyl-3-oxo-2,3,3a,4,6,7-hexahydro-pyrazolo[4,3-c]pyridin-5-yl)-1-(R)-benzyloxymethyl-2-oxo-ethylcarbamoy]-1-methyl-ethyl}-carbamic Acid Tert-butyl Ester A mixture of 4.83 g (12.7 mmol) of 14F, the solution from 14H, 2.60 g (19.1 mmol) of HOAT, and 2.45 g (12.8 mmol) of EDC was stirred at about 0° C. under nitrogen for about 1 h and then warmed to room temperature and stirred for about 16 h. The mixture was filtered and the filtrate was washed with saturated aqueous sodium bicarbonate and water, dried over $MgSO_4$ and concentrated to give 7.35 g of 14I as a white solid.

J. 2-Amino-N-[2-(3a-(R)-benzyl-2-methyl-3-oxo-2,3,3a,4,6,7-hexahydro-pyrazolo[4,3-c]pyridin-5-yl)-1-(R)-benzylomethyl-2-oxo-ethyl]-isobutyramide To 755 mg (1.25 mmol) of 14I in 7 mL of methylene chloride at about 0° C. was added 3.5 mL of cold trifluoroacetic acid and the mixture was stirred for about 1 h at about 0° C. The mixture was allowed to warm to room temperature and stirred for about 2 h. The mixture was concentrated and co-evaporated twice with toluene. The residue was dissolved in chloroform and washed twice with saturated aqueous sodium bicarbonate and once each with water and brine. The mixture was dried over $MgSO_4$ and concentrated to give 594 mg of 14J as an oil.

EXAMPLE 15

2-Amino-N-[1-(R)-benzloxyethyl-2-(2-methyl-3 oxo-2,3,3a,4,6,7-hexahydro-pyrazolo[4,3-c]pyridin-5-yl)-2-oxo-ethyl]-isobutyramide Hydrochloride A. 2-Methyl-3-oxo-2,3,3a,4,6,7-hexahydro-pyrazolo[4,3-c]pyridine-5-carboxyfic acid Tert-butyl Ester A mixture of 3.00 g (11.66 mmol) of 3A and 537 mg (11.66 mmol) of methylhydrazine in 100 mL of ethanol was heated at reflux for about 17 h. The mixture was concentrated and the residue was dissolved in 100 mL toluene and heated at reflux for about 17 h. The mixture was diluted with ethyl acetate, and washed twice with brine, dried over $MgSO_4$ and concentrated. The residue was purified by silica gel chromatography using an elution gradient of 100% ethyl acetate to 5% methanol in methylene chloride to give 2.28 g of 16A as a white solid. $^1HNMR$ ($CD_3OD$): δ 4.20 (s, 2H), 3.67 (t, 2H), 3.43 (s, 3H), 2.58 (t, 2H), 1.48 (s, 9H).

B. 2-Methyl-2,3a,4,5,6,7-hexahydro-pyrazolo[4,3-c]pydidin-3one Hydrochloride

To 510 mg (2.01 mmol) of 15A in 30 mL of ethanol was added 10 mL of concentrated HCl and the mixture was stirred at room temperature for about 35 min. The mixture was concentrated and the residue was crystallized from methanolethyl acetate to give 425 mg of 15B as a yellow solid. $^1HNMR$ ($CD_3OD$): δ 4.27 (S, 2H), 3.71 (S, 3H), 3.56 (T, 2H). 3.05 (T, 2H).

C. {1-[1-(R)-Belnzyloxymethyl-2-(2-methyl-3-oxo-2,3,3a,4,6,7-hexahydro-pyrazolo[4,3-c]pyridin-5-yl)-2-oxo-ethylcarbamoyl]-1-methyl-ethyl}-carbamic Acid Tert-butyl Ester According to the method outlined in General Procedure A, 100 mg (0.53 mmol) of 15B and 202 mg (0.53 mmol) of 1E were coupled and the residue was purified by silica gel chromatography (95:5 v/v methylene chloride:methanol) to give 54 mg of 15C as a white solid. MS (Cl, $NH_3$) 516 ($MH^+$).

D. 2-Amino-N-[1-R-benzyloxymethyl-2-(2-methyl-3-oxo-2,3,3a,4,6,7-hexahydro-pyrazolo[4,3-c]pyddin-5-yl)-2-oxo-ethyl]-isobutyrmide Hydrochloride To 54 mg (0.10 mmol) of 15C in 30 mL of ethanol was added 10 mL of concentrated HCl and the mixture was stirred at room temperature for about 40 min. The mixture was concentrated and the residue was precipitated from methanovethyl acetate to give 50 mg of 15D. MS (Cl, NH$_3$) 416 (MH$^+$). $^1$HNMR (CD$_3$OD): (partial) δ 7.28 (m, 5 H), 5.18 (m 1 H), 4.69–4.38 (m, 4 H), 3.88 (m, 1 H, 3.73 (m, 2 H), 3.68 (s, 2 H), 3.61 (m, 1 H), 2.67 (m, 1 H, 1.57 (S, 6 H).

EXAMPLE 16

2-Amino-N-[2-(2-benzyl-3-oxo-2,3,3a,4,6,7-hexahydro-gyrazolo[4,3-c]pyridin-5-yl)-1(R)-(1H-indol-3-ylmethy)-2-oxo-ethyl]-isobutyramide Hydrochloride A. 2-Benoyl-3-oxo-2,3,3a,4,6,7-hexahydro-pyrazolo[4,3-c]pyridine-5-carboxylic Acid Tert-butyl Ester A mixture of 800 mg (3.11 mmol) of 3A and 495 mg (3.11 mmol) of benzyl-hydrazine dihydrochloride in 15 mL of ethanol was heated at reflux for about 17 h. The mixture was concentrated and the residue was dissolved in 100 mL toluene and heated at reflux for about 48 h. The mixture was diluted with ethyl acetate, and washed twice with brine, dried over Na$_2$SO$_4$ and concentrated. The residue was purified by silica gel chromatography using an elution gradient of 100% ethyl acetate to 5% methanol in methylene chloride to give 530 mg of 16A as a tan solid. MS (Cl, NH$_3$) 330 (MH$^+$).

B. 2-Benzl-2,3a,4,5,6,7-hexahydro-pyrazolo[4,3-c]pyriidin-3-one Hydrochloride

To 411 mg (1.24 mmol) of 16A in 30 mL of ethanol was added 10 mL of concentrated HCl and the mixture was stirred at room temperature for about 30 min. The mixture was concentrated and the residue was crystallized from methanovethyl acetate to give 353 mg of 16B as a yellow solid. MS (Cl, NH$_3$) 230 (MH$^+$). $^1$HNMR (CD$_3$OD): δ0 7.26–7.40 (m, 5H), 5.22 (s, 2H), 4.12 (s, 2H), 3.53 (t, 2H), 3.00 (t, 2H).

C. (R)-2-(2-tert-Butoxycarbonylamino-2-methyl-propionylamino)-3-(1H-indol-3-yl)-propionic Acid To a stirring solution of 30.6 g (0.15 mol) of D-tryptophan, 30.4 g (0.30 mol) of N-methylmorpholine in 450 mL of (4:1) dioxane:water, was added 45.0 g (0.15 mol) of 14E and the mixture was stirred for about 72 h. Excess dioxane was removed by evaporation and water and ethyl acetate were added to the mixture. The pH of the solution was adjusted to 3 with concentrated HCl and the layers were separated. The organic layer was washed with water and brine, dried over MgSO$_4$ and concentrated. The residue was crystallized from ethyl acetatelhexanes to give 37.0 g of an off-white solid.

D. {1-[2-(2-Benzyl-3-oxo-2,3,3a,4,6,7-hexahydro-pyrazolor-[4,3-c]pyridin-yl)-1-(R)-(1H-indol-3-ylmethyl)-2-oxo-ethylcarbamoyl]-1-methyl-ethyl}-carbamic Acid Tert-butyl Ester According to the method outlined in General Procedure A, 100 mg (0.38 mmol) of 16B and 202 mg (0.53 mmol) of 1C were coupled and the residue was purified by silica gel chromatography (95:5 v/v methylene chloride:methanol) to give 45 mg of 16D as a white solid. MS (Cl, NH$_3$) 601 (MH$^+$).

E. 2-Amino-N-[2-(2-benzyl-3-oxo-2,3,3a,4,6,7-hexahydro-pyrazolo[4,3-c]pyridn-5-yl)-1-(R)-(1H-indol-3-ylmethyl)-2-oxo-ethyl]-isobutyramide Hydrochloride To 45 mg (0.07 mmol) of 16D in 60 mL of ethanol was added 20 mL of concentrated HCl and the mixture was stirred at room temperature for 35 min. The mixture was concentrated and the residue was precipitated from methanol/ethyl acetate to give 30 mg of 16E. $^1$HNMR (CD$_3$OD): (partial) δ 7.40 (m, 4 H), 7.25 (m, 3 H), 7.11 (m, 2 H), 6.96 (m, 2 H), 6.81 (m, 1 H, 5.38–4.93 (m, 3 H), 4.46 (m, 1 H, 4.22 (m, 1 H), 3.96 (m, 1H, 3.69 (m, 1 H), 3.18 (m, 1 H), 2.28 (m, 1 H), 1.57 (m, 6 H), 1.38 (m, 1 H).

EXAMPLE 17

2-Amino-N-[1-benzyloxymethyl-2-(2,3a-dimethyl-3-oxo-2,3,3a,4,6,7-hexahydro-pyrazolo[4,3-c]pyridin-5-yl)-2-oxo-ethyl]-isobutyramide Hydrochloride A. 3-Methyl-4-oxo-piperidine-1,3-dicarboxylic Acid 1-tert-butyl Ester 3-(R,S)-methyl Ester To a solution of 2.00 g (7.77 mmol) 3A in 30 mL of DMF was added 308 mg (7.77 mmol) of sodium hydride (60% oil dispersion) and the mixture was stirred at room temperature for about 25 min. To the stirring solution was added 0.50 mL (7.77 mmol) of methyl iodide and the mixture was stirred for about 17 h at room temperature. The mixture was diluted with ethyl acetate and washed once with water and four times with brine, dried over MgSO$_4$, and concentrated. The residue was purified by silica gel chromatography (7:3 v/v hexane:ethyl acetate) to give 1.75 g of 17A as a clear oil. MS (Cl, NH$_3$) 272 (MH$^+$).

B. 2,3a-(R,S)-Dimethyl-3-oxo-2,3,3a, 4,6,7-hexahydro-pyrazolo[4,3-c]pyridine-5-carboxylic Acid Tert-butyl Ester A mixture of 1.62 g (9.50 mmol) of 17A and 435 mg (9.50 mmol) of methylhydrazine in 30 mL of ethanol was heated at reflux for about 4 h. The mixture was concentrated and the residue was dissolved in 50 mL toluene and heated at reflux for about 14 h. The mixture was diluted with ethyl acetate, and washed twice with brine. dried over Na$_2$SO$_4$ and concentrated. The residue was purified by silica gel chromatography (7:3 v/v hexane:ethyl acetate) to give 1.00 g of 17B as a white solid. MS (Cl, NH$_3$) 268 (MH$^+$).

C. 2,3a-(R,S)-Dimethyl-2,3a,4,5,6,7-hexahydro-gyrazolo[4,3-c]pyridin-3-one Hydrochlorid To 1.00 g (3.74 mmol) of 17B in 40 mL of ethanol was added 8 mL of concentrated HCl and the mixture was stirred at room temperature for about 35 min. The mixture was concentrated and the residue was crystallized from methanol/ethyl acetate to give 850 mg of 17C as a white solid. MS (Cl, NH$_3$) 168 (MH$^+$).

D. {1-[1-(R)-Benzyloxymethyl-2-(2,3a-(R,S)-dimethyl-3-oxo-2,3,3a,4,6,7-hexahydro-pyrazolo[4,3-c]pyridin-5-yl)-2-oxo-ethylcarbamoyl]-1-methyl-ethyl}-carbamic Acid Tert-butyl Ester According to the method outlined in General Procedure A, 150 mg (0.74 mmol) of 17C and 514 mg (1.35 mmol) of 1E were coupled and the residue was purified by silica gel chromatography (85:15 v/v hexane:ethyl acetate) to give 185 mg of 17D as a white solid.

E. 2-Amino-N-[1-(R)-benzyloxymethyl-2-(2,3a-(R,S)-dimethyl-3-oxo-2,3,3a,4,6,7-hexahydro-pyrazolo[4,3-c]pyridin-5-yl)-2-oxo-ethyl]-isobutyramide Hydrochloride To 173 mg (0.33 mmol) of 17B in 40 mL of ethanol was added 15 mL of concentrated HCl and the mixture was stirred at room temperature for about 1 h. The mixture was concentrated and the residue was diluted with chloroform and washed with saturated aqueous sodium bicarbonate and brine, dried over Na$_2$SO$_4$ and the residue was purified by silica gel chromatography using an elution gradient of 100% ethyl acetate to 10% diethylamine in ethyl acetate. The residue was dissolved in ethanol and acidified with aqueous HCl. The mixture was concentrated and the residue was crystallized from methanollethyl acetate to give 65 mg of 17E as a white solid. MS (Cl, NH$_3$) 502 (MH$^+$). $^1$HNMR (CD$_3$OD): (partial) δ 7.32 (m, 5 H), 5.14 (m, 1 H), 4.53 (m, 3 H), 3.71 (m, 3 H), 2.97 (m, 1 H), 2.83 (m, 1 H), 2.57 (m, 1 H), 1.98 (m, 2 H), 1.61 (m, 6 H), 1.38 (s, 3 H).

EXAMPLE 18

2Amino-N-[2-3a-(R)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide Hydrochloride and 2-Amino-N-[2-(3a-(S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide Hydrochloride A. 3-Benzyl-4-oxo-piperidine-3-carboxylic acid Methyl Ester To 200 mg (0.58 mmol) of 3B at about 0° C. was added 5 mL of cold trifluoroacetic acid and the mixture was stirred for about 1 h. The mixture was concentrated and the residue was co-evaporated with ethyl acetate and hexane. To the residue was added 2N NaOH to make it basic and the mixture was extracted with chloroform. The combined organic extracts were dried over $MgSO_4$ and concentrated to give 18A in quantitative yield.

B. 3-(R,S)-Benzyl-1-[3-benzyloxy-2-(R)-(2-tert-butoxycarbonylamino-2-methyl-propionylamino)-propionyl]-4-oxo-piperidine-3-carboxylic Acid Methyl Ester According to the method outlined in General Procedure A, 1.77 g (7.16 mmol) of 18A and 3.04 g (8.0 mmol) of 14F were coupled to give a mixture of diastereomers. The residue was purified by silica gel chromatography (7:3 v/v hexane:ethyl acetate) to give 820 mg of less polar 186 isomer 1 and 1.14 g more polar 186 isomer 2. MS (Cl, $NH_3$) 611 ($MH^+$) for both isomers.

C. {1-[2-(3a-(R,S)-Benzyl-3-oxo-2,3,3a 4,6,7-hexahydro-pyrazolo[4,3-c]pyridin-5-yl)-1-(R)-benzyloxymethyl-2-oxo-ethylcarbamoyl]-1-methyl-ethyl}-carbamic Acid Tert-butyl Ester To a solution of 820 mg (1.32 mmol) of 186 isomer 1 in 13 mL of ethanol was added 342 mg (2.63 mmol) of hydrazine sulfate and 431 mg (5.26 mmol) of sodium acetate and the mixture was heated at reflux for about 17 h. The mixture was concentrated and the residue was diluted with ethyl acetate and washed with saturated aqueous sodium bicarbonate and brine, dried over $MgSO_4$ and concentrated. The residue was purified by silica gel chromatography using an elution gradient of 75% ethyl acetate in hexane to 100% ethyl acetate to give 550 mg of 15C isomer 1.

To a solution of 1.14 g (1.86 mmol) of 18B isomer 2 in 20 mL of ethanol was added 485 mg (3.73 mmol) of hydrazine sulfate and 613 mg (7.48 mmol) of sodium acetate and the mixture was heated at reflux for about 17 h. The mixture was concentrated and the residue was diluted with ethyl acetate and washed with saturated aqueous sodium bicarbonate and brine, dried over $MgSO_4$ and concentrated. The residue was purified by silica gel chromatography (75:25 v/v ethyl acetatelhexane) to give 710 mg of 18C isomer 2.

D. 2-Amino-N-[2-(3a-(R)-benzyl-3-oxo-2,3,3a,4,6,7-hexahydro-pymzolo[4,3-c]pyridin-5-yl)-1-(R)-benzyloxymethyl-2-oxo-ethyl]-isobutyramide Hydrochloride To 200 mg (0.34 mmol) of ISC isomer 1 in 12 mL of ethanol was added 6 mL of concentrated HCl and the mixture was stirred at room temperature for about 2.5 h. The mixture was concentrated and evaporated three times with ethanol to give 20 mg of 18D isomer 1. MS (Cl, $NH_3$) 492 ($MH^+$). $^1HNMR$ ($CD_3OD$): (partial)δ 8.42 (br d, 1 H, 7.35 (m, 5 H), 7.18 (m, 5 H), 5.23 (m, 2 H), 4.91 (m, 1 H, 4.54 (m, 4 H), 3.80 (m, 2 H), 3.63 (m, 1 H), 3.12 (m, 1 H), 3.07 (m, 3 H), 2.61 (m, 3 H), 1.62 (m, 6 H), 1.39 (m, 1H).

E. 2-Amino-N-[2-(3a-(S)-berizyl-3-oxo-2,3,3a,4,6,7-hexahydro-pyrazolo[4,3-c]pyridin-5-yl)-1-(R)-benzyloxymethyl-2-oxo-ethyl]-isobutyramide Hydrochloride To 200 mg (0.34 mmol) of 18C isomer 2 in 20 mL of ethanol was added 10 mL of concentrated HCl and the mixture was stirred at room temperature for about 2.5 h. The mixture was concentrated and co-evaporated three times with ethanol to give 30 mg of 18E isomer 2. MS (Cl, $NH_3$) 492 ($MH^+$). $^1HNMR$ ($CD_3OD$): (partial) δ 8.29 (br d, 1 H), 7.30 (m, 5 H), 7.11 (m, 4 H), 6.88 (m, 1 H), 5.29 (m, 1 H), 4.92 (m, 1 H), 4.62 (m, 3 H), 3.91–3.70 (m, 3 H), 3.22–2.95 (m, 3 H), 2.66 (m, 3 H), 1.57 (m, 6 H), 1.30 (m, 1 H), 0.89 (m, 1H).

EXAMPLE 19

2-Amino-N-[1-(R)-benzyloxymethyl-2-(2-methyl-3-oxo-3a-(R,S)-thiazol-4-ylmethyl-2,3,3a,4,6,7-hexahydro-pyrazolo[4,3-c]pyridin-5-yl)-2-oxo-ethyl]-1-iobutyramide Dhydrochloride A. 4Oxo-3-(R,S)-thiazol-4-ylmethyl-piperidinIe-1,3-dlarboxylic Acid 1-tert-butyl ester 3-ethyl Ester To a solution of 300 mg (1.10 mmol) of 1A in 5 mL of THF at about 0° C. was added 67 mg (1.66 mmol) of sodium hydride (60% oil dispersion) and the mixture was stirred for about 30 min. A solution of 204 mg (1.21 mmol) of 4-chloromethylthiazole (Hsiao, C. N; Synth. Comm. 20, p. 3507 (1990)) in 5 mL of THF was added to the cold solution, followed by 87 mg (0.53 mmol) of potassium iodide and the mixture was heated at reflux for about 17 h. The mixture was diluted with water and extracted with ethyl acetate. The combined organic extracts were dried over $Na_2SO_4$ and concentrated and the residue was purified by silica gel chromatography (7:3 v/v hexane:ethyl acetate) to give 90 mg of the title compound. MS (Cl, $NH_3$) 648 ($MH^+$).

B. 2-Methyl-3-oxo-3a-(R,S)-thiazolfylmethyl-2,3,3a,4,6,7-hexahydro-pyrazolo[4,3-c]pyridine-5-carboxylic Acid Tert-butyl Ester To 90 mg (0.24 mmol) of 19A in 2 mL of ethanol was added 11.2 mg (0.24 mmol) of methylhydraine and the mixture was heated at reflux for about 17 h. An additional 33.6 mg (0.72 mmol) of methylhydrazine was added and the mixture was heated at reflux for about 7 h. The mixture was concentrated and the residue was dissolved in 3 mL of toluene and heated at reflux for about 17 h. The mixture was concentrated and the residue was purified by silica gel chromatography (6:4 v/v hexane:ethyl acetate) to give 44 mg of 19B. MS (Cl, $NH_3$) 648 ($MH^+$).

C. 2-Methyl-3a-(R,S)-thiazol-4-ylmethyl-2,3a,4,5,6,7-hexahydro-pyrazolo[4,3-c]pyridin-3-one Dihydrochloride A mixture of 44 mg (0.10 mmol) of 19B in 1 mL of 4M HCl in dioxane was stirred at room temperature for about 4 h. The mixture was concentrated and co-evaporated with methylene chloride to give 40 mg of 19C. MS (Cl, $NH_3$) 251 ($MH^+$).

D. {1-[1-(R)-Benzyloxymethyl-2-(2-methyl-3-oxo-3a-(R,S)-thiazol-4-ylmethyl-2,3,3a,4,6,7-hexahydro-pyrazolo[4,3-c]pynidin-5-yl)-2-oxo-ethylcarbamoyl]-1-methyl-ethyl}-carbamic Acid Tert-butyl Ester According to the method outlined in General Procedure A, 40 mg (0.12 mmol) of 19C and 39 mg (0.12 mmol) of 14F were coupled and the residue was purified by silica gel chromatography (9:1 v/v ethyl acetate:hexane) to give 40 mg of 190. MS (Cl, $NH_3$) 613 ($MH^+$).

E. 2-Amino-N-[1-(R)-benzyloxymethyl-2-(2-methyl-3-oxo-3a-(R,S)-thiazol-4-ylmethyl-2,3,3a,4,6,7-hexahydro-pyrazolo[4,3-c]pyridin-5-yl-2-oxo-ethyl]-isobutyramide Dihydrochloride A mixture of 40 mg (0.06 mmol) of 19D in 1 mL of 4M HCl in dioxane was stirred at room temperature for about 5 h. The mixture was concentrated and co-evaporated with methylene chloride to give 40 mg of 19E. MS (Cl, $NH_3$) 513 ($MH^+$).

EXAMPLE 20

2-Amino-N-[2-(3a-(R)-benzyl-2-methyl-3-oxo-2,3,3a,4,6,7-hexahydro-pymzolo[4,3-c]pyridin-5-yl)-1-(R)-benzyloxymethyl-2oxo-ethyl]-isobutyramide L-artaric acid salt To 4.6 g of the title compound of Example 14 in 20 mL of methanol, a solution of 1.36 g of L-tartaric acid in 20 mL of methanol was added at about 0° C. The mixture was warmed to room temperature, stirred for about 40 min and concentrated in vacuo. The residue was diluted with 220 mL of ethyl acetate, heated at reflux for about 1.5 h, then stirred at about 72° C. for about 18 h. The mixture was cooled to room temperature, and filtered to give 5.78 g of the title compound as a colorless crystalline solid.

EXAMPLE 21

3-Benzyl-3-methoxycarbonylmethyl-4-oxo-piperidine-1-carboxylic Acid Tert-butyl Ester A. 3-Benzyl-4-oxo-piperidine-1-carboxylic Acid Tert-butyl Ester A mixture of the β-ketoester (4480 mg, 12.9 mmol) and LiCl (1100 mg, 25.8 mmol) was heated in DMF (2.0 ml) at about 120° C. for about 17 h. The reaction mixture was cooled to room temperature and extracted with EtOAc (3×100 mL). The combined extracts were dried and concentrated in vacuo. The crude product was chromatographed on $SiO_2$ using 20% ethyl acetatethexanes to give 1320 mg of the desired product as a yellow oil. $^1$H NMR (250 MHz, $CDCl_3$): d: 7.4 (m, 5H), 4.2 (m, 1H), 3.4 (m, 1 H), 3.3 (dd, 1 H), 3.05 (dd, 1H), 2.7 (m, 1H), 2.55 (m, 4), 1.5 (s, 9H); MS (APCI): 190 (M+1-BOC).

B. 3-Benzy-3-methoxycarbonylmethyl-4-oxo-piperidine-1-carboxylic Acid Tert-butyl Ester A solution of the product from Step A of Example 21 above (1320 mg, 4.56 mmol), pyrrolidine (972 mg, 13 mmol) and p-toluenesulfonic add (33 mg) in benzene (30 ml) was refluxed through 3A molecular sieves for about 17 h. The reaction mixture was cooled to room temperature and concentrated in vacuo. The residue was dissolved in benzene (10 ml) and cooled to about 0° C. Methyl bromoacetate (1530 mg, 10 mmol) was added dropwise. The reaction mixture was slowly allowed to warm to room temperature and then was heated under reflux for about 17 h at which point $H_2O$ (5 mL) was added. After refluxing for about another 2 h, the reaction mixture was cooled to room temperature and extracted with EtOAc (3×100 ml). The combined organic extracts were dried and concentrated in vacuo. The crude residue was chromatographed on $SiO_2$-gel using 15% ethyl acetate/hexanes to give 280 mg of product. $^1$H NMR (250 MHz, $CDCl_3$): d 7.35 (m, 5 H), 4.5 (m, 1H, 3.8 (s, 3H), 3.4 (dd, 1 H), 3.1 (m, 1 H), 2.85 (m, 4H), 2.6 (m, 1H, 2.4 (m, 1 H), 1.5 (s, 9 H); MS (APCI): 362 (M+1).

EXAMPLE 22

6-Oxo-1-phenyl-cyclohexane-1,3-dicarboxylic Acid 3-tert-butyl Ester 1-methyl Ester A solution of diphenylmercury (890 mg, 2.5 mmol) in $CHCl_3$ (4 ml) under $N_2$ was heated to about 40° C. Lead tetraacetate (1110 mg, 2.5 mmol) was added in small portions and the greenish yellow solution was stirred at about 40° C. for about 0.5 h. The Fketoester (520 mg, 2.0 mmol) was then added, followed by pyridine (0.2 ml, 2.5 mmol). After about 5 h at about 40° C., the reaction mixture was concentrated in vacuo and the residue was dissolved in ether (100 ml) and filtered. The filtrate was washed with 3N $H_2SO_4$ (3x), dried and concentrated to give 616 mg of a yellow solid. Flash chromatography over $SiO_2$ gel using 25% ethyl acetatelhexanes provided 368 mg of the desired product. $^1$H NMR (400 MHz, $CDCl_3$): d 7.15 (m, 5 H), 4.4 (s, 2 H), 3.7 (s, 5 H), 2.6 (s, 2 H), 1.5 (s, 9H); MS (APCI): 334 (M+1)

EXAMPLE 23

(D)-2-Amino-3-(2-dichloro-benzyloxy)-propionic Acid Hydrochloride

A. (D)-2-tert-Butoxycarbonylamino-3-(2,4-dichloro-benzyloxy)-propionic Acid

To a stirred solution of Boc-D-serine (8.2 g 40 mmol) in DMF (75 ml) at about 0° C. was added NaH (60% dispersion, 3.2 g, 80 mmol) over about a 10 minute period. The reaction mixture was stirred for about 1.75 h at about 0° C., then about 0.25 h at room temperature. After cooling to about 0° C., a solution of 2,4-dichlorotoluene (5.56 ml, 40 mmol) in DMF (5 ml) was added dropwise. The reaction mixture was allowed to warm to about 23° C. and was stirred for about 17 h, then was partitioned between di-isopropylether and 10% HCl. The aqueous solution was extracted with di-isopropyl ether (2x). The combined extracts were washed with saturated aqueous brine, dried and concentrated to give 14.75 g of crude product which was used without further purification. $^1$H NMR (40 MHz, $CDCl_3$): d 7.6–7.2 (m, 3 H), 5.4 (d, 1 H), 4.6 (s, 2 H), 4.0 (d, 1 H), 3.8 (dd, 2 H), 1.1 (s, 9H); MS (APCI): 264,266 (M+1, M+2).

B. (D)-2-Amino-3-(2,4-dichloro-benzyloxy)-propionic Acid Hydrochloride

The product from step A of Example 23 above (14.7 g, 40 mmol) was stirred in 4 M HCl/dioxane (100 ml) for about 17 h. The reaction mixture was concentrated in vacuo to give 12 g of a pale yellow solid (100%). MS (APCI): 265 (M+1).

EXAMPLE 24

Example 24 having the formula shown below,

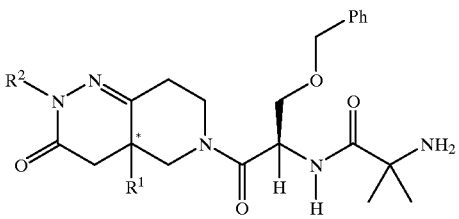

wherein $R^1$ is —$CH_2$-phenyl and $R^2$ is methyl, was synthesized in an analogous manner to the procedures described in Examples 3C to 3F using the title compound of Example 21 as starting material. Both the R,R and S,R diastereomers (* indicates he other stereoisomer center at the C-3 carbon of the above structure) were isolated. Mass spec. (M+1)=520; MS method=particle bombardment.

EXAMPLES 25 and 26

Examples 25 and 26 having the formula shown below,

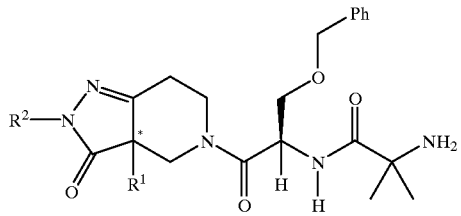

wherein for both examples 25 and 26 $R^1$ is phenyl and $R^2$ is methyl, where example 25 is the R,R isomer and example 26 is the S,R isomer. Examples 25 and 26 were synthesized in an analogous manner to the procedures described in Examples 3C to 3F using the title compound of Example 22 as starting material followed by chromatographic separation of the two separate isomers. Mass spec. of each example (M+1)=493, MS method=particle bombardment.

EXAMPLES 27–159

Examples 27 to 159 listed in the table below, were prepared according to the scheme illustrated below by coupling the appropriately substituted pyrazalone-piperidine of formula I (in the below scheme) with the (D)-OBnSer derivative II (in the below scheme) in an analogous manner to the procedures described in Examples 3E and 3F.

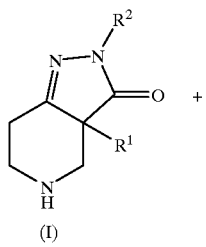

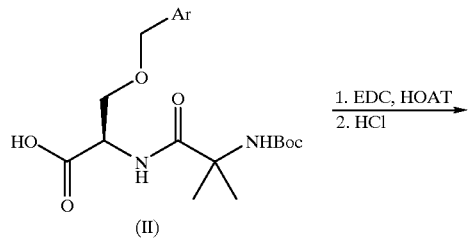

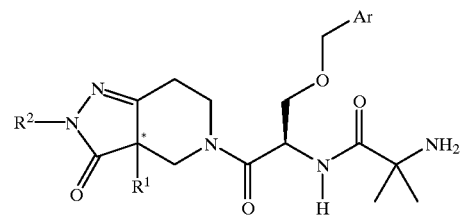

The pyrazalone-piperidines of formula I were prepared analogously according to the procedures described in Examples 3B and 3C starting with the appropriate alkylating agent and alkylhydrazine; the (D)-OBnSer derivatives (II) were prepared in three steps analogously to the procedures described in Example 23A, Example 23B and Example 5F.

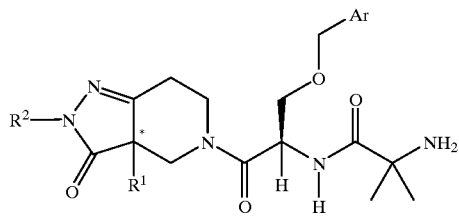

| Ex. # | Isomer | $R^2$ | $R^1$ = -Ch$_2$-A$^1$ | Ar | MS | MS Method |
|---|---|---|---|---|---|---|
| 27 | d1 | H | 2-pyridyl | phenyl | 493 | PB |
| 28 | d1 | H | 4-thiazolyl | phenyl | 499 | PB |
| 29 | d2 | H | 4-thiazolyl | phenyl | 499 | PB |
| 30 | d1 | H | 5-thiazolyl | phenyl | 499 | APCI |
| 31 | d1 | Me | phenyl | 2,4-di-Cl-Ph | 574.5 | APCI |
| 32 | d1 | Me | phenyl | 2,4-di-F-Ph | 542 | PB |
| 33 | d1 | Me | phenyl | [2,3-O—CH$_2$O]Phenyl | 550.2 | PB |
| 34 | d1 | Me | phenyl | 2-CF$_3$-Ph | 575 | PB |
| 35 | d1 | Me | phenyl | 2-Me-Ph | 520 | PB |
| 36 | d1 | Me | phenyl | 2-pyridyl | 507 | PB |
| 37 | d1 | Me | phenyl | 3,4-di-F-Ph | 542 | PB |

-continued

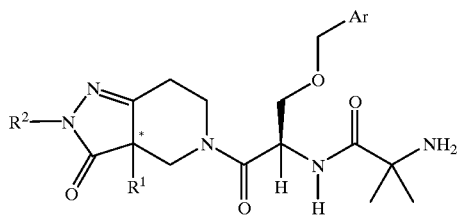

| Ex. # | Isomer | R² | R¹ = -CH₂-A¹ | Ar | MS | MS Method |
|---|---|---|---|---|---|---|
| 38 | d1,2 | Me | phenyl | 3,5-di-CF₃-Ph | 642 | PB |
| 39 | d1 | Me | phenyl | 3,5-di-Cl-Ph | 576 | APCI |
| 40 | d2 | Me | phenyl | 3-CF₃-Ph | 575 | APCI |
| 41 | d1 | Me | phenyl | 3-Cl-Ph | 540 | APCI |
| 42 | d1 | Me | phenyl | 3-Cl-thiophene | 546, 548 | APCI |
| 43 | d1 | Me | phenyl | 3-F-4-Cl-Ph | 560 | APCI |
| 44 | d1 | Me | phenyl | 3-Me-Ph | 520 | PB |
| 45 | d1 | Me | phenyl | 4-Cl-Ph | 640 | PB |
| 46 | d1 | Me | phenyl | 4-Pyridyl | 507 | PB |
| 47 | d1 | Me | phenyl | 4-thiazolyl | 513 | PB |
| 48 | d1 | Me | Phenyl | 5-thiazolyl | 513 | APCI |
| 49 | d1,2 | Me | phenyl | benzisoxazolyl | 547 | PB |
| 50 | d1 | Me | phenyl | 4-pyrimidinyl | 508 | PB |
| 51 | d1,2 | Me | 4-Ph-Ph | 4-thiazolyl | 589 | APCI |
| 52 | d1,2 | Me | 4-Ph-Ph | 2-Pyridyl | 583 | APCI |
| 53 | d1 | Me | 4-F-Ph | phenyl | 524 | PB |
| 54 | d2 | Me | 4-F-Ph | phenyl | 524 | PB |
| 55 | d1 | Me | 4-F-Ph | 3-Cl-Ph | 558 | PB |
| 56 | d2 | Me | 4-F-Ph | 3-Cl-Ph | 558 | PB |
| 57 | d1 | Me | 4-F-Ph | 3,4-di-F-Ph | 560 | APCI |
| 58 | d2 | Me | 4-F-Ph | 3,4-di-F-Ph | 560 | APCI |
| 59 | d1,2 | Me | 4-F-Ph | 2-pyridyl | 525 | APCI |
| 60 | d1,2 | Me | 4-F-Ph | 2-CF₃-Ph | 592 | APCI |
| 61 | d1 | Me | 4-CF₃-Ph | 4-Cl-Ph | 609 | APCI |
| 62 | d1,2 | Me | 4-CF₃-Ph | 4-Cl-Ph | 609 | APCI |
| 63 | d1,2 | Me | 3-pyridyl | phenyl | 508 | PB |
| 64 | d1 | Me | 3-phenyl | 3-pyridyl | 508 | PB |
| 65 | d1 | Me | 2-quinolinyl | phenyl | 594 | PB |
| 66 | d2 | Me | 2-quinolinyl | phenyl | 594 | PB |
| 67 | d1 | Me | 2-pyridyl | phenyl | 506 | PB |
| 68 | d2 | Me | 2-pyridyl | phenyl | 506 | PB |
| 69 | d1,2 | Me | 2-pyridyl | 3-F-4-Cl-Ph | 559, 561 | APCI |
| 70 | d1 | Me | 2-pyridyl | 3-Cl-thiophene | 547, 549 | APCI |
| 71 | d1 | Me | 2-pyridyl | 3-CF₃-Ph | 575 | PB |
| 72 | d1,2 | Me | 2,4-di-F-Ph | 3,4-di-F-Ph | 579 | APCI |
| 73 | d1,2 | Me | 2,4-di-F-Ph | 2-pyridyl | 544 | PB |
| 74 | d1 | Me | 4-thiazolyl | phenyl | 513 | APCI |
| 75 | d2 | Me | 4-thiazolyl | phenyl | 513 | PB |
| 76 | d1 | Me | 5-thiazolyl | phenyl | 513 | PB |
| 77 | d1 | Et | 2-pyridyl | phenyl | 521 | PB |
| 78 | d1,2 | Et | phenyl | 4-thiazolyl | 541 | APCI |
| 79 | d1 | Et | phenyl | 3,5-di-CF₃-Ph | 656 | PB |
| 80 | d1,2 | Et | phenyl | 3,4-di-F-Ph | 556 | PB |
| 81 | d1 | Et | 2,4-di-F-Ph | 2,4-di-F-Ph | 593 | APCI |
| 82 | d2 | Et | 2,4-di-F-Ph | 2,4-di-F-Ph | 593 | APCI |
| 83 | d1 | Et | 2,4-di-F-Ph | 2-CF₃-Ph | 625 | APCI |
| 84 | d2 | Et | 2,4-di-F-Ph | 2-CF₃-Ph | 625 | APCI |
| 85 | d1 | Et | 2,4-di-F-Ph | 3,4-di-F-Ph | 593 | APCI |
| 86 | d2 | Et | 2,4-di-F-Ph | 3,4-di-F-Ph | 593 | APCI |
| 87 | d1 | Et | 2-pyridyl | 3,4-di-F-Ph | 607 | PB |
| 88 | d2 | Et | 2-pyridyl | 3,4-di-F-Ph | 607 | PB |
| 89 | d1 | Et | 4-CF₃-Ph | 2,4-di-F-Ph | 625 | APCI |
| 90 | d2 | Et | 4-CF₃-Ph | 2,4-di-F-Ph | 625 | APCI |
| 91 | d1 | Et | 4-CF₃-Ph | 3-Cl-Ph | 623 | APCI |
| 92 | d1 | Et | 4-CF₃-Ph | 4-Cl-Ph | 623 | APCI |
| 93 | d2 | Et | 4-CF₃-Ph | 4-Cl-Ph | 623 | APCI |
| 94 | d1 | Et | 4-CH₃-Ph | 3-Cl-Ph | 568 | APCI |
| 95 | d2 | Et | 4-CH₃-Ph | 3-Cl-Ph | 568 | APCI |
| 96 | d1 | Et | 4-Cl-Ph | 3,4-di-F-Ph | 590 | PB |
| 97 | d2 | Et | 4-Cl-Ph | 3,4-di-F-Ph | 590 | PB |
| 98 | d1 | Et | 4-Cl-Ph | 3-5-di-Cl-Ph | 622 | PB |
| 99 | d2 | Et | 4-Cl-Ph | 3-5-di-Cl-Ph | 622 | PB |
| 100 | d1 | Et | 4-Cl-Ph | 3-Cl-Ph | 589 | PB |
| 101 | d2 | Et | 4-Cl-Ph | 3-Cl-Ph | 589 | PB |

-continued

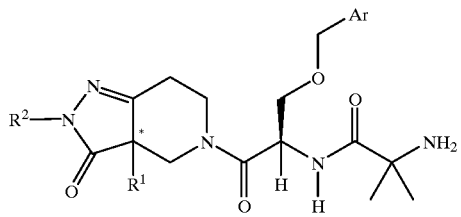

| Ex. # | Isomer | R² | R¹ = -Ch₂-A¹ | Ar | MS | MS Method |
|---|---|---|---|---|---|---|
| 102 | d1 | Et | 4-F-Ph | 3,4-di-F-Ph | 574 | PB |
| 103 | d2 | Et | 4-F-Ph | 3,4-di-F-Ph | 574 | PB |
| 104 | d1 | Et | 4-F-Ph | 3-Cl-Ph | 572 | APCI |
| 105 | d2 | Et | 4-F-Ph | 3-Cl-Ph | 572 | APCI |
| 106 | d1,2 | Et | 4-Me-Ph | 2-CF₃-Ph | 602 | APCI |
| 107 | d1,2 | Et | 4-Me-Ph | 3,4-di-F-Ph | 570 | APCI |
| 108 | d1,2 | CF₃CH₂ | phenyl | 4-thiazolyl | 595 | APCI |
| 109 | d1 | CF₃CH₂ | phenyl | 3-CF₃-Ph | 642.3 | APCI |
| 110 | d1 | CF₃CH₂ | phenyl | 3,5-di-Cl-Ph | 643 | APCI |
| 111 | d2 | CF₃CH₂ | phenyl | 3,5-di-Cl-Ph | 644 | APCI |
| 112 | d1 | CF₃CH₂ | phenyl | 3,4-di-F-Ph | 610.2 | APCI |
| 113 | d2 | CF₃CH₂ | phenyl | 3,4-di-F-Ph | 610.2 | APCI |
| 114 | d1 | CF₃CH₂ | phenyl | 3,5-di-Cl-Ph | 643 | APCI |
| 115 | d2 | CF₃CH₂ | phenyl | 3,5-di-Cl-Ph | 644 | APCI |
| 116 | d1 | CF₃CH₂ | phenyl | 3-CF₃-Ph | 642.3 | APCI |
| 117 | d1 | CF₃CH₂ | phenyl | 3,4-di-F-Ph | 610.2 | APCI |
| 118 | d2 | CF₃CH₂ | phenyl | 3,4-di-F-Ph | 610.2 | APCI |
| 119 | d1,2 | CF₃CH₂ | phenyl | 4-thiazolyl | 595 | APCI |
| 120 | d1,2 | CF₃CH₂ | 2,4-di-Cl-Ph | 2-pyridyl | 643 | APCI |
| 121 | d1,2 | CF₃CH₂ | 2,4-di-Cl-Ph | 4-thiazolyl | 649 | APCI |
| 122 | d1 | CF₃CH₂ | 2,4-F-Ph | 2-CF₃-Ph | 679 | APCI |
| 123 | d2 | CF₃CH₂ | 2,4-F-Ph | 2-CF₃-Ph | 679 | APCI |
| 124 | d1 | CF₃CH₂ | 2,4-F-Ph | 3,4-di-F-Ph | 647 | APCI |
| 125 | d2 | CF₃CH₂ | 2,4-F-Ph | 3,4-di-F-Ph | 647 | APCI |
| 126 | d1,2 | CF₃CH₂ | 2,4-F-Ph | 4-thiazolyl | 617 | PB |
| 127 | d1 | CF₃CH₂ | 2-pyridyl | 2,4-di-Cl-Ph | 643 | APCI |
| 128 | d2 | CF₃CH₂ | 2-pyridyl | 2,4-di-Cl-Ph | 643 | APCI |
| 129 | d1 | CF₃CH₂ | 2-pyridyl | 2,4-di-F-Ph | 611 | PB |
| 130 | d2 | CF₃CH₂ | 2-pyridyl | 2,4-di-F-Ph | 611 | PB |
| 131 | d1 | CF₃CH₂ | 2-pyridyl | 2-CF₃-4-F-Ph | 661 | APCI |
| 132 | d1 | CF₃CH₂ | 2-pyridyl | 2-CF₃-Ph | 643 | PB |
| 133 | d2 | CF₃CH₂ | 2-pyridyl | 2-CF₃-Ph | 643 | PB |
| 134 | d1 | CF₃CH₂ | 2-pyridyl | 3,4-di-F-Ph | 611 | PB |
| 135 | d2 | CF₃CH₂ | 2-pyridyl | 3,4-di-F-Ph | 611 | PB |
| 136 | d1 | CF₃CH₂ | 2-pyridyl | 3,5-di-Cl-Ph | 643 | APCI |
| 137 | d1 | CF₃CH₂ | 2-pyridyl | 3-Cl-Ph | 609 | PB |
| 138 | d1 | CF₃CH₂ | 2-pyridyl | 3-Cl-thiophene, | 615, 617 | APCI |
| 139 | d1,2 | CF₃CH₂ | 2-pyridyl | 3-F-4-Cl-Ph | 627, 629 | APCI |
| 140 | d1 | CF₃CH₂ | 2-pyridyl | 3-OCF₃-Ph | 659 | APCI |
| 141 | d1 | CF₃CH₂ | 2-pyridyl | 4-Cl-Ph | 609 | PB |
| 142 | d2 | CF₃CH₂ | 2-pyridyl | 4-Cl-Ph | 609 | PB |
| 143 | d1,2 | CF₃CH₂ | 2-pyridyl | 2,4-di-F-Ph | 612 | APCI |
| 144 | d1,2 | CF₃CH₂ | 3-pyridyl | 2-CF₃-Ph | 644 | APCI |
| 145 | d1,2 | CF₃CH₂ | 3-pyridyl | 4-Cl-Ph | 610 | APCI |
| 146 | d1 | CF₃CH₂ | 4-CH₃-Ph | 3-Cl-Ph | 622 | APCI |
| 147 | d2 | CF₃CH₂ | 4-CH₃-Ph | 3-Cl-Ph | 622 | APCI |
| 148 | d1 | CF₃CH₂ | 4-Cl-Ph | 3,4-di-F-Ph | 644 | PB |
| 149 | d2 | CF₃CH₂ | 4-Cl-Ph | 3,4-di-F-Ph | 644 | PB |
| 150 | d1 | CF₃CH₂ | 4-Cl-Ph | 3,5-di-Cl-Ph | 675 | PB |
| 151 | d2 | CF₃CH₂ | 4-Cl-Ph | 3,5-di-Cl-Ph | 675 | PB |
| 152 | d2 | CF₃CH₂ | 4-Cl-Ph | 3-Cl-Ph | 642 | PB |
| 153 | d1 | CF₃CH₂ | 4-Cl-Ph | 3-Cl-Ph | 642 | PB |
| 154 | d1 | CF₃CH₂ | 4-F-Ph | 3,4-di-F-Ph | 628 | PB |
| 155 | d2 | CF₃CH₂ | 4-F-Ph | 3,4-di-F-Ph | 628 | PB |
| 156 | d1 | CF₃CH₂ | 4-F-Ph | 3-Cl-Ph | 626 | PB |
| 157 | d2 | CF₃CH₂ | 4-F-Ph | 3-Cl-Ph | 626 | PB |
| 158 | d1,2 | CF₃CH₂ | 4-Me-Ph | 2-CF₃-Ph | 656 | APCI |
| 159 | d1,2 | CF₃CH₂ | 4-Me-Ph | 3,4-di-F-Ph | 624 | APCI |

Note: in the above table, the isomer designation refers to the stereochemistry at the C-3 position (indicated by the "*" in the structure) of the pyrazalone-piperidine group; d1 and d2 refer to isomers that were chromatographically separated; d1,2 refers to a mixture of isomers. Abbreviations used in the table above are: Ph is phenyl; PB is particle bombardment; and APCI is atmospheric pressure chemical ionization. The following are NMR data for the compounds of the above table as indicated.

Example 37: $^1$H NMR (400 MHz, d4-MeOH): d 7.2 (m, 5H), 5.2 (t, 1H), 4.6 (m, 3H), 3.8 (2H), 3.1 (d, 1 H), 3.0 (s, 3H), 2.6 (dd, 2H), 1.6 (s, 6H).

Examples 67 & 68: $^1$H NMR (300 MHz, d4-MeOH): d 8.85 (s, 1 H), 8.6 (t, 1 H), 8.1 (d, 1H), 8.0 (t, 1H), 7.35 (s, 5H), 5.15 (s, 1H), 4.6 (bs, 3H), 3.85 (m,2H), 3.65 (m, 2H), 3.2 (s, 3H), 2.75 (m, 2H), 1.65 (s, 6H).

Example 128: $^1$H NMR (400 MHz, d4-MeOH):d 8.8 (s, 1 H), 8.6 (s, 1 H), 8.5 (t, 1 H), 7.96 (t, $_1$ H), 7.9 (d, 1 H), 7.45 (d, 1H), 7.33 (d, 1H), 5.2 (s, 1H), 4.6 (s, 3H), 4.4 (m, 1H), 4.2 (m, 2H), 3.9 (m, 4H), 3.5 (m), 3.2 (m, 2H), 2.8 (dd, 2H), 1.6 (s, 6H).

Examples 129 & 130: $^1$H NMR (400 MHz, d4MeOH): d 8.76 (s, 1 H), 8.50 (t, 1H), 7.92 (dt,2H), 7.43 (q, 1H). 6.90 (t, 1H), 5.20 (m, 1H), 4.90 (m), 4.30 (m, 1H), 4.20 (m, 1H) 3.7–3.4 (m), 3.30 (s, 2H), 3.20 (m, 1H), 2.80 (dd, 2H), 1.60 (s, 6H).

Example 137: $^1$H NMR (300 MHz, d4-MeOH): d 8.7 (1, 1H), 8.45 (t, 1 H), 7.9 (t, 2 H), 7.25 (m, 4 H), 5.2 (m, 1 H), 4.95 (d, 1 H), 4.6 (s, 2H), 4.3 (m, 1 H), 3.8 (t, 2H), 3.5 (dd, 2 H), 2.8 (m, 1 H), 2.8 (dd, 2 H), 1.6 (s, 6H).

Example 138: $^1$H NMR (400 MHz, d4-MeOH): d 8.8 (dd, 1H), 8.6 (s, 1H), 8.5 (t, 1H), 7.95 (t, 1H), 7.9 (s, 1H), 7.3 (s, 1H), 7.0 (s, 1H), 5.2 (s, 1H), 4.85 (s, 3H), (m, 1H), 4.18 (m, 1H), 3.8 (m, 2H), 3.5 (dd, 2H), 3.2 (d, 2H), 2.8 (dd, 2H), 1.6 (s, 6H), Examples 141 & 142: $^1$H NMR (300 MHz, d4-MeOH): d 8.75 (m, 1 H, 8.5 (m, 1 H, 7.9 (m, 2 H), 7.3 (s, 2 H), 5.2 (m, 1H), 4.65 (m, 1 H), 4.55 (s, 2 H), 4,35 (m, 1 H), 4.20 (m, 1 H), 3.8 (t, 1 H), 3.5 (dd, 2 H), 3.15 (d, 1 H), 2.8 (dd, 2 H), 1.6 (s, 2 H).

EXAMPLES 160–179

Examples 160 to 179 shown in the table below were prepared according to the scheme illustrated below by coupling the appropriately substituted pyrazalone-piperidine (I) (in the scheme) with the (D)-Trp derivative (III) (see Example 2C) in an analogous manner to the procedures described in Examples 3E and 3F.

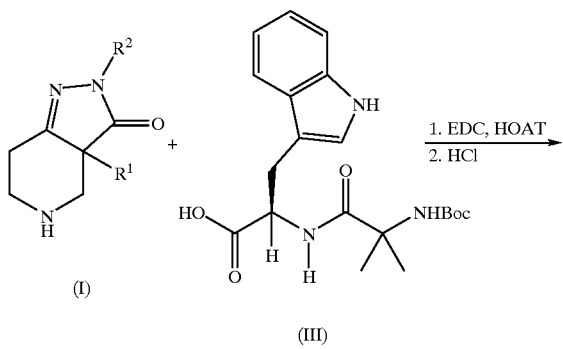

-continued

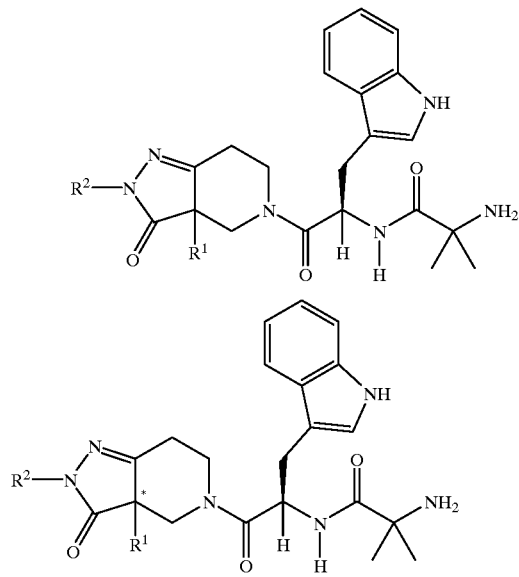

| Ex. # | Isomer | R² | R¹ = -CH₂-A¹ | MS | MS Method |
|---|---|---|---|---|---|
| 160 | d1 | Me | 4-CF₃-Ph | 584 | APCI |
| 161 | d1,2 | Me | 4-CF₃-Ph | 584 | APCI |
| 162 | d1 | Me | 4-F-Ph | 533 | PB |
| 163 | d2 | Me | 4-F-Ph | 533 | PB |
| 164 | d1 | Me | 4-Ph-Ph | 591 | APCI |
| 165 | d1,2 | Et | 2,4-di-Cl-Ph | 597 | APCI |
| 166 | d1,2 | Et | 2,4-F-Ph | 566 | APCI |
| 167 | d1 | Et | 4-CF₃-Ph | 598 | APCI |
| 168 | d1,2 | Et | 4-CF₃-Ph | 598 | APCI |
| 169 | d1 | Et | 4-Cl-Ph | 563 | PB |
| 170 | d2 | Et | 4-Cl-Ph | 563 | PB |
| 171 | d1,2 | Et | 4-F-Ph | 547 | APCI |
| 172 | d1,2 | Et | 4-Me-Ph | 543 | APCI |
| 173 | d1,2 | CF₃CH₂ | 2,4-di-Cl-Ph | 651.5 | APCI |
| 174 | d1,2 | CF₃CH₂ | 2,4-di-F-Ph | 620 | APCI |
| 175 | d1 | CF₃CH₂ | 4-Cl-Ph | 617 | PB |
| 176 | d2 | CF₃CH₂ | 4-Cl-Ph | 617 | PB |
| 177 | d1 | CF₃CH₂ | 4-F-Ph | 601 | APCI |
| 178 | d2 | CF₃CH₂ | 4-F-Ph | 601 | APCI |
| 179 | d1,2 | CF₃CH₂ | 4-Me-Ph | 597 | APCI |

Note: in the above table, the isomer designation refers to the stereochemistry at the C-3 position (indicated by the "*" in the structure) of the pyrazalone-piperidine group; d1 and d2 refer to isomers that were chromatographically separated; d1,2 refers to a mixture of isomers.

EXAMPLES 180–183

Examples 180 to 183 shown in the table below were prepared according to the scheme illustrated below by coupling the appropriately substituted pyrazalone-piperidine I with the acid intermediate IV in an analogous manner to the procedures described in Examples 3E and 3F.

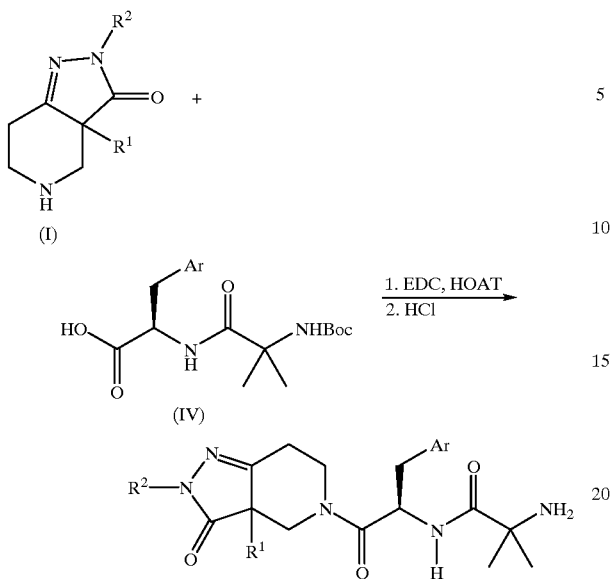

The acid intermediate (IV) was prepared by treating an amino acid with the product from Example 5D using the established procedure described in Example 5F.

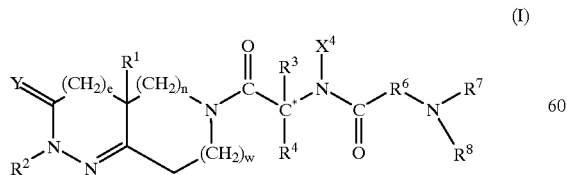

| Ex. # | Isomer | $R^2$ | $R^1 = $-$CH_2$-$A^1$ | Ar | MS | Method |
|---|---|---|---|---|---|---|
| 180 | d1,2 | Me | Phenyl | $(CH_2)_2Ph$ | 504 | PB |
| 181 | d1,2 | Me | Phenyl | $SCH_2Ph$ | 559 | PB |
| 182 | d1 | Me | Phenyl | 2-Naphthalenyl | 527 | APCI |
| 183 | d1,2 | Me | Phenyl | $CH_2O$-(4-F-Ph) | 524 | PB |

Note: in the above table, the isomer designation refers to the stereochemistry at the C3 position (indicated by the "*" in the structure) of the pyrazalone-piperidine group; d1 and d2 refer to isomers that were chromatographically separated; d1,2 refers to a mixture of isomers.

What is claimed is:

1. A method for treating or preventing a disease or condition which may be treated or prevented by growth hormone which comprises administering to a human or other animal in need of such treatment or prevention an amount of a compound of formula (I)

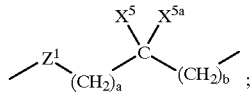

the racemic-diastereomeric mixtures and optical isomers of said compounds and the pharmaceutically-acceptable salts and prodrugs thereof, wherein e is 0;

n is 0 and w is 2, or n is 1 and w is 1, or n is 2 and w is 0;

Y is oxygen or sulfur;

$R^1$ is —$(CH_2)_qN(X^6)C(O)(CH_2)_t$—$A^1$, —$(CH_2)_qN(X^6)SO_2(CH_2)_t$—$A^1$, —$(CH_2)_qN(X^6)C(O)N(X^6)(CH_2)_t$—$A^1$, —$(CH_2)_qC(O)N(X^6)(CH_2)_t$—$A^1$, —$(CH_2)_qC(O)O(CH_2)_t$—$A^1$, —$(CH_2)_qOC(O)(CH_2)_t$—$A^1$, —$(CH_2)_qOC(O)N(X^6)(CH_2)_t$—$A^1$, —$(CH_2)_qC(O)(CH_2)_t$—$A^1$, —$(CH_2)_qS(O)_m(CH_2)_t$—$A^1$, —$(CH_2)_t$—$A^1$, or —$(CH_2)_q$—$Y^1$—$(CH_2)_t$—$A^1$;

where the alkyl and cycloalkyl groups in the definition of $R^1$ are optionally substituted with $(C_1$-$C_4)$alkyl, hydroxyl, $(C_1$-$C_4)$alkoxy, carboxyl, —$CONH_2$, —$S(O)_m(C_1$-$C_6)$alkyl, —$CO_2(C_1$-$C_4)$alkyl ester, 1H-tetrazol-5-yl or 1, 2 or 3-fluoro;

$Y^1$ is O, $S(O)_m$, —$C(O)NX^6$—, —$CH$=$CH$—, —$C$≡$C$—, —$N(X^6)C(O)$—, —$C(O)NX^6$—, —$C(O)O$—, —$OC(O)N(X^6)$— or —$OC(O)$—;

q is 0, 1, 2, 3 or 4;

t is 0, 1, 2 or 3;

said $(CH_2)_q$ group and $(CH_2)_t$ group may each be optionally substituted with hydroxyl, $(C_1$-$C_4)$alkoxy, carboxyl, —$CONH_2$, —$S(O)_m(C_1$-$C_6)$alkyl, —$CO_2(C_1$-$C_4)$alkyl ester, 1H-tetrazol-5-yl, 1, 2 or 3-fluoro, or 1 or 2 $(C_1$-$C_4)$alkyl;

$R^2$ is hydrogen, $(C_1$-$C_8)$alkyl, —$(C_0$-$C_3)$alkyl-$(C_3$-$C_8)$cycloalkyl, —$(C_1$-$C_4)$alkyl-$A^1$ or $A^1$;

where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1$-$C_6)$alkyl, —$C(O)A^1$, —$C(O)(X^6)$, $CF_3$, CN or 1, 2 or 3 halogen;

$R^3$ is $A^1$, $(C_1$-$C_{10})$alkyl, —$(C_1$-$C_6)$alkyl-$A^1$, —$(C_1$-$C_6)$alkyl-$(C_3$-$C_7)$cycloalkyl, —$(C_1$-$C_5)$alkyl-$X^1$-$(C_1$-$C_5)$alkyl, —$(C_1$-$C_5)$alkyl-$X^1$-$(C_0$-$C_5)$alkyl-$A^1$ or —$(C_1$-$C_5)$alkyl-$X^1$-$(C_1$-$C_5)$alkyl-$(C_3$-$C_7)$cycloalkyl;

where the alkyl groups in the definition of $R^3$ are optionally substituted with, —$S(O)_m(C_1$-$C_6)$alkyl, —$C(O)OX^3$, 1, 2, 3, 4 or 5 halogens, or 1, 2 or 3 $OX^3$;

$X^1$ is O, $S(O)_m$, —$N(X^2)C(O)$—, —$C(O)N(X^2)$—, —$OC(O)$—, —$C(O)O$—, —$CX^2$=$CX^2$—, —$N(X^2)C(O)O$—, —$OC(O)N(X^2)$— or —$C$=$C$—;

$R^4$ is hydrogen, $(C_1$-$C_6)$alkyl or $(C_3$-$C_7)$cycloalkyl;

$X^4$ is hydrogen or $(C_1$-$C_6)$alkyl or $X^4$ is taken together with $R^4$ and the nitrogen atom to which $X^4$ is attached and the carbon atom to which $R^4$ is attached and form a five to seven membered ring;

$R^6$ is $$\diagup Z^1 \diagdown_{(CH_2)_a} \overset{X^5 \ X^{5a}}{\underset{\diagup}{C}} \diagdown_{(CH_2)_b} \diagup \ ;$$

where a and b are independently 0, 1, 2 or 3;

$X^5$ and $X^{5a}$ are each independently selected from the group consisting of hydrogen, trifluoromethyl, $A^1$ and optionally substituted $(C_1$-$C_6)$alkyl;

the optionally substituted $(C_1$-$C_6)$alkyl in the definition of $X^5$ and $X^{5a}$ is optionally substituted with a substituent selected from the group consisting of $A^1$, $OX^2$, —$S(O)_m(C_1$-$C_6)$alkyl, —$C(O)OX^2$, $(C_3$-$C_7)$cycloalkyl, —$N(X^2)(X^2)$ and —$C(O)N(X^2)(X^2)$;

$Z^1$ is a bond, O or N—$X^2$, provided that when a and b are both 0 then $Z^1$ is not N—$X^2$ or O;

$R^7$ and $R^8$ are independently hydrogen or optionally substituted ($C_1$-$C_6$)alkyl;

where the optionally substituted ($C_1$-$C_6$)alkyl in the definition of $R^7$ and $R^8$ is optionally independently substituted with $A^1$, —C(O)O—($C_1$-$C_6$)alkyl, —S(O)$_m$($C_1$-$C_6$)alkyl, 1 to 5 halogens, 1 to 3 hydroxy, 1 to 3 —O—C(O)($C_1$-$C_{10}$)alkyl or 1 to 3 ($C_1$-$C_6$)alkoxy; or $R^7$ and $R^8$ can be taken together to form —(CH$_2$)$_r$—L—(CH$_2$)$_r$—;

where L is C($X^2$)($X^2$), S(O)$_m$ or N($X^2$);

$A^1$ in the definition of $R^1$ is ($C_5$-$C_7$)cycloalkenyl, phenyl or a partially saturated, fully saturated or fully unsaturated 4- to 8-membered ring, a bicyclic ring system consisting of a partially saturated, fully unsaturated or fully saturated 5- or 6-membered ring, fused to a partially saturated, fully saturated or fully unsaturated 5- or 6-membered ring;

$A^1$ in the definition of $R^2$, $R^3$, $R^6$, $R^7$ and $R^8$ is independently ($C_5$-$C_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —O$X^6$, —C(O)N($X^6$)($X^6$), —C(O) O$X^6$, oxo, ($C_1$-$C_6$)alkyl, nitro, cyano, benzyl, —S(O)$_m$($C_1$-$C_6$)alkyl, 1H-tetrazol-5-yl, phenyl, phenoxy, phenylalkyloxy, halophenyl, methylenedioxy, —N($X^6$)($X^6$), —N($X^6$)C(O)($X^6$), —SO$_2$N($X^6$)($X^6$), —N($X^6$)SO$_2$-phenyl, —N($X^6$) SO$_2$$X^6$, —CON$X^{11}$$X^{12}$, —SO$_2$N$X^{11}$$X^{12}$, —N$X^6$SO$_2$$X^{12}$, —N$X^6$CON$X^{11}$$X^{12}$, —N$X^6$SO$_2$N$X^{11}$$X^{12}$, —N$X^6$C(O)$X^{12}$, imidazolyl, thiazolyl or tetrazolyl, provided that if $A^1$ is optionally substituted with methylenedioxy then it can only be substituted with one methylenedioxy;

where $X^{11}$ is hydrogen or optionally substituted ($C_1$-$C_6$)alkyl;

the optionally substituted ($C_1$-$C_6$)alkyl defined for $X^{11}$ is optionally independently substituted with phenyl, phenoxy, ($C_1$-$C_6$) alkoxycarbonyl, —S(O)$_m$($C_1$-$C_6$)alkyl 1 to 5 halogens, 1 to 3 hydroxy, 1 to 3 ($C_1$-$C_{10}$) alkanoyloxy or 1 to 3 ($C_1$-$C_6$)alkoxy;

$X^{12}$ is hydrogen, ($C_1$-$C_6$)alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, CH$_3$, OCH$_3$, OCF$_3$ and CF$_3$; or $X^{11}$ and $X^{12}$ are taken together to form —(CH$_2$)$_r$—$L^1$—(CH$_2$)$_r$—;

where $L^1$ is C($X^2$)($X^2$), O, S(O)$_m$ or N($X^2$);

r for each occurrence is independently 1, 2 or 3;

$X^2$ for each occurrence is independently hydrogen, optionally substituted ($C_1$-$C_6$)alkyl, or optionally substituted ($C_3$-$C_7$)cycloalkyl, where the optionally substituted ($C_1$-$C_6$)alkyl and optionally substituted ($C_3$-$C_7$)cycloalkyl in the definition of $X^2$ are optionally independently substituted with —S(O)$_m$($C_1$-$C_6$)alkyl, —C(O)O$X^3$, 1 to 5 halogens or 1–3 O$X^3$;

$X^3$ for each occurrence is independently hydrogen or ($C_1$-$C_6$)alkyl;

$X^6$ is independently hydrogen, optionally substituted ($C_1$-$C_6$)alkyl, ($C_2$-$C_6$)halogenated alkyl, optionally substituted ($C_3$-$C_7$)cycloalkyl, ($C_3$-$C_7$)-halogenatedcycloalkyl, where optionally substituted ($C_1$-$C_6$)alkyl and optionally substituted ($C_3$-$C_7$) cycloalkyl in the definition of $X^6$ is optionally independently substituted by 1 or 2 ($C_1$-$C_4$)alkyl, hydroxyl, ($C_1$-$C_4$)alkoxy, carboxyl, CONH$_2$, —S(O)$_m$($C_1$-$C_6$) alkyl, carboxylate ($C_1$-$C_4$)alkyl ester, or 1H-tetrazol-5-yl; or when there are two $X^6$ groups on one atom and both $X^6$ are independently ($C_1$-$C_6$)alkyl, the two ($C_1$-$C_6$)alkyl groups may be optionally joined and, together with the atom to which the two $X^6$ groups are attached, form a 4- to 9-membered ring optionally having oxygen, sulfur or N$X^7$;

$X^7$ is hydrogen or ($C_1$-$C_6$)alkyl optionally substituted with hydroxyl; and m for each occurrence is independently 0, 1 or 2;

with the proviso that:

$X^6$ and $X^{12}$ cannot be hydrogen when it is attached to C(O) or SO$_2$ in the form C(O)$X^6$, C(Q)$X^{12}$, SO$_2$$X^6$ or SO$_2$$X^{12}$; and when $R^6$ is a bond then L is N($X^2$) and each r in the definition —(CH$_2$)$_r$—L—(CH$_2$)$_r$— is independently 2 or 3;

which is effective in promoting release of endogenous growth hormone; and wherein the human or other animal is a growth hormone deficient adult.

2. A method of claim 1 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide.

3. A method of claim 1 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, L-tartaric acid salt.

4. A method for treating or preventing a disease or condition which may be treated or prevented by growth hormone which comprises administering to a human or other animal in need of such treatment or prevention an amount of a compound of formula I

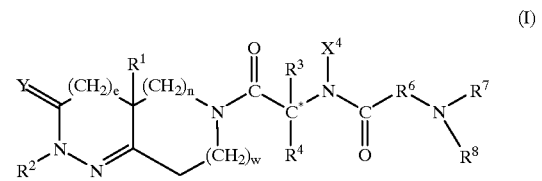

(I)

the racemic-diastereomeric mixtures and optical isomers of said compounds and the pharmaceutically-acceptable salts and prodrugs thereof, wherein e is 0;

n is 0 and w is 2, or n is 1 and w is 1, or n is 2 and w is 0;

Y is oxygen or sulfur;

$R^1$ is —$(CH_2)_qN(X^6)C(O)(CH_2)_t$—$A^1$, —$(CH_2)_qN(X^6)SO_2(CH_2)_t$—$A^1$, —$(CH_2)_qN(X^6)C(O)N(X^6)(CH_2)_t$—$A^1$, —$(CH_2)_qC(O)N(X^6)(CH_2)_t$—$A^1$, —$(CH_2)_qC(O)O(CH_2)_t$—$A^1$, —$(CH_2)_qOC(O)(CH_2)_t$—$A^1$, —$(CH_2)_qOC(O)N(X^6)(CH_2)_t$—$A^1$, —$(CH_2)_qC(O)(CH_2)_t$—$A^1$, —$(CH_2)_qS(O)_m(CH_2)_t$—$A^1$, —$(CH_2)_t$—$A^1$, or —$(CH_2)_q$—$Y^1$—$(CH_2)_t$—$A^1$;

where the alkyl and cycloalkyl groups in the definition of $R^1$ are optionally substituted with ($C_1$–$C_4$)alkyl, hydroxyl, ($C_1$–$C_4$)alkoxy, carboxyl, —$CONH_2$, —$S(O)_m(C_1$–$C_6)$alkyl, —$CO_2(C_1$–$C_4)$alkyl ester, 1H-tetrazol-5-yl or 1, 2 or 3-fluoro;

$Y^1$ is O, $S(O)_m$, —$C(O)NX^6$—, —CH=CH—, —C≡C—, —$N(X^6)C(O)$—, —$C(O)NX^6$—, —C(O)O—, —$OC(O)N(X^6)$— or —OC(O)—;

q is 0, 1, 2, 3 or 4;

t is 0, 1, 2 or 3;

said $(CH_2)_q$ group and $(CH_2)_t$ group may each be optionally substituted with hydroxyl, ($C_1$–$C_4$) alkoxy, carboxyl, —$CONH_2$, —$S(O)_m(C_1$–$C_6)$alkyl, —$CO_2(C_1$–$C_4)$alkyl ester, 1H-tetrazol-5-yl, 1, 2 or 3-fluoro, or 1 or 2 ($C_1$–$C_4$)alkyl;

$R^2$ is hydrogen, ($C_1$–$C_8$)alkyl, —($C_0$–$C_3$)alkyl-($C_3$–$C_8$)cycloalkyl, —($C_1$–$C_4$)alkyl-$A^1$ or $A^1$;

where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1$–$C_6)$alkyl, —$C(O)A^1$, —$C(O)(X^6)$, $CF_3$, CN or 1, 2 or 3 halogen;

$R^3$ is $A^1$, ($C_1$–$C_{10}$)alkyl, —($C_1$–$C_6$)alkyl-$A^1$, —($C_1$–$C_6$)alkyl-($C_3$–$C_7$)cycloalkyl, —($C_1$–$C_5$)alkyl-$X^1$-($C_1$–$C_5$)alkyl, —($C_1$–$C_5$)alkyl-$X^1$-($C_0$–$C_5$)alkyl-$A^1$ or —($C_1$–$C_5$)alkyl-$X^1$-($C_1$–$C_5$)alkyl-($C_3$–$C_7$)cycloalkyl;

where the alkyl groups in the definition of $R^3$ are optionally substituted with, —$S(O)_m(C_1$–$C_6)$alkyl, —$C(O)OX^3$, 1, 2, 3, 4 or 5 halogens, or 1, 2 or 3 $OX^3$;

$X^1$ is O, $S(O)_m$, —$N(X^2)C(O)$—, —$C(O)N(X^2)$—, —OC(O)—, —C(O)O—, —$CX^2$=$CX^2$—, —$N(X^2)C(O)O$—, —$OC(O)N(X^2)$— or —C≡C—;

$R^4$ is hydrogen, ($C_1$–$C_6$)alkyl or ($C_3$–$C_7$)cycloalkyl;

$X^4$ is hydrogen or ($C_1$–$C_6$)alkyl or $X^4$ is taken together with $R^4$ and the nitrogen atom to which $X^4$ is attached and the carbon atom to which $R^4$ is attached and form a five to seven membered ring;

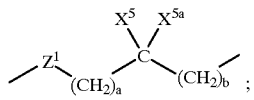

$R^6$ is where a and b are independently 0, 1, 2 or 3;

$X^5$ and $X^{5a}$ are each independently selected from the group consisting of hydrogen, trifluoromethyl, $A^1$ and optionally substituted ($C_1$–$C_6$)alkyl;

the optionally substituted ($C_1$–$C_6$)alkyl in the definition of $X^5$ and $X^{5a}$ is optionally substituted with a substituent selected from the group consisting of $A^1$, $OX^2$, —$S(O)_m(C_1$–$C_6)$alkyl, —$C(O)OX^2$, ($C_3$–$C_7$)cycloalkyl, —$N(X^2)(X^2)$ and —$C(O)N(X^2)(X^2)$;

$Z^1$ is a bond, O or N—$X^2$, provided that when a and b are both 0 then $Z^1$ is not N—$X^2$ or O;

$R^7$ and $R^8$ are independently hydrogen or optionally substituted ($C_1$–$C_6$)alkyl;

where the optionally substituted ($C_1$–$C_6$)alkyl in the definition of $R^7$ and $R^8$ is optionally independently substituted with $A^1$, —C(O)O—($C_1$–$C_6$)alkyl, —$S(O)_m(C_1$–$C_6)$alkyl, 1 to 5 halogens, 1 to 3 hydroxy, 1 to 3 —O—$C(O)(C_1$–$C_{10})$alkyl or 1 to 3 ($C_1$–$C_6$)alkoxy; or $R^7$ and $R^8$ can be taken together to form —$(CH_2)_r$—L—$(CH_2)_r$—;

where L is $C(X^2)(X^2)$, $S(O)_m$ or $N(X^2)$;

$A^1$ in the definition of $R^1$ is ($C_5$–$C_7$)cycloalkenyl, phenyl or a partially saturated, fully saturated or fully unsaturated 4- to 8-membered ring, a bicyclic ring system consisting of a partially saturated, fully unsaturated or fully saturated 5- or 6-membered ring, fused to a partially saturated, fully saturated or fully unsaturated 5- or 6-membered ring;

$A^1$ in the definition of $R^2$, $R^3$, $R^6$, $R^7$ and $R^8$ is independently ($C_5$–$C_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, ($C_1$–$C_6$)alkyl, nitro, cyano, benzyl, —$S(O)_m(C_1$–$C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$SO_2N(X^6)(X^6)$, —$N(X^6)SO_2$—phenyl, —$N(X^6)SO_2X^6$, —$CONX^{11}X^{12}$, —$SO_2NX^{11}X^{12}$, —$NX^6SO_2X^{12}$, —$NX^6CONX^{11}X^{12}$, —$NX^6SO_2NX^{11}X^{12}$, —$NX^6C(O)X^{12}$, imidazolyl, thiazolyl or tetrazolyl, provided that if $A^1$ is optionally substituted with methylenedioxy then it can only be substituted with one methylenedioxy;

where $X^{11}$ is hydrogen or optionally substituted ($C_1$–$C_6$)alkyl;

the optionally substituted ($C_1$–$C_6$)alkyl defined for $X^{11}$ is optionally independently substituted with phenyl, phenoxy, ($C_1$–$C_6$)alkoxycarbonyl, —$S(O)_m(C_1$–$C_6)$alkyl 1 to 5 halogens, 1 to 3 hydroxy, 1 to 3 ($C_1$–$C_{10}$)alkanoyloxy or 1 to 3 ($C_1$–$C_6$) alkoxy;

$X^{12}$ is hydrogen, ($C_1$–$C_6$)alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$; or $X^{11}$ and $X^{12}$ are taken together to form —$(CH_2)_r$—$L^1$—$(CH_2)_r$—;

where $L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted ($C_1$–$C_6$)alkyl, or optionally substituted ($C_3$–$C_7$)cycloalkyl, where the optionally substituted ($C_1$–$C_6$)alkyl and optionally substituted ($C_3$–$C_7$)cycloalkyl in the definition of $x^2$ are optionally independently substituted with —$S(O)_m(C_1$–$C_6)$alkyl, —$C(O)OX^3$, 1 to 5 halogens or 1–3 $OX^3$;

$X^3$ for each occurrence is independently hydrogen or ($C_1$–$C_6$)alkyl;

$X^6$ is independently hydrogen, optionally substituted ($C_1$–$C_6$)alkyl, ($C_2$–$C_6$)halogenated alkyl, optionally substituted ($C_3$–$C_7$)cycloalkyl, ($C_3$–$C_7$)-halogenatedcycloalkyl, where optionally substituted ($C_1$–$C_6$)alkyl and optionally substituted ($C_3$–$C_7$)cycloalkyl in the definition of $X^6$ is optionally independently substituted by 1 or 2 ($C_1$–$C_4$)alkyl, hydroxyl, ($C_1$–$C_4$)alkoxy, carboxyl, $CONH_2$, —$S(O)_m(C_1$–$C_6)$ alkyl, carboxylate ($C_1$–$C_4$)alkyl ester, or 1H-tetrazol-5-yl; or when there are two $X^6$ groups on one atom and both $X^6$ are independently ($C_1$–$C_6$)alkyl, the two ($C_1$–$C_6$)alkyl groups may be optionally joined and, together with the atom to which the two $X^6$ groups are attached, form a 4- to 9-membered ring optionally having oxygen, sulfur or $NX^7$;

$X^7$ is hydrogen or ($C_1$–$C_6$)alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^6$ is a bond then L is $N(X^2)$ and each r in the definition —$(CH_2)_r$—L—$(CH_2)_r$— is independently 2 or 3;

which is effective in promoting release of endogenous growth hormone; and wherein the disease or condition is a side effect of glucocorticoid treatment.

5. A method of claim 4 wherein the disease or condition is a catabolic side effect of glucocorticoid treatment.

6. A method of claim 4 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide.

7. A method of claim 4 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, L-tartaric acid salt.

8. A method for treating or preventing a disease or condition which may be treated or prevented by growth hormone which comprises administering to a human or other animal in need of such treatment or prevention an amount of a compound of formula I

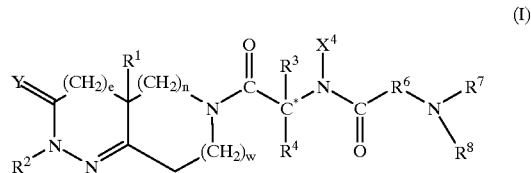

(I)

the racemic-diastereomeric mixtures and optical isomers of said compounds and the pharmaceutically-acceptable salts and prodrugs thereof, wherein e is 0;

n is 0 and w is 2, or n is 1 and w is 1, or n is 2 and w is 0;

Y is oxygen or sulfur;

$R^1$ is —$(CH_2)_qN(X^6)C(O)(CH_2)_t$—$A^1$, —$(CH_2)_qN(X^6)SO_2(CH_2)_t$—$A^1$l, $(CH_2)_qN(X^6)C(O)N(X^6)(CH_2)_t$—$A^1$, —$(CH_2)_qC(O)N(X^6)(CH_2)_t$—$A^1X$, —$(CH_2)_qC(O)O(CH_2)_t$—$A^1$, —$(CH_2)_qOC(O)(CH_2)_t$—$A^1$l, $(CH_2)_qOC(O)N(X^6)(CH_2)_t$—$A^1$, —$(CH_2)_qC(O)(CH_2)_t$—$A^1$, —$(CH_2)_qS(O)_m(CH_2)_t$—$A^1$, —$(CH_2)_t$—$A^1$, or —$(CH_2)_q$—$Y^1$—$(CH_2)_t$—$A^1$;

where the alkyl and cycloalkyl groups in the definition of $R^1$ are optionally substituted with ($C_1$–$C_4$)alkyl, hydroxyl, ($C_1$–$C_4$)alkoxy, carboxyl, —$CONH_2$, —$S(O)_m(C_1$–$C_6)$alkyl, —$CO_2(C_1$–$C_4)$alkyl ester, 1H-tetrazol-5-yl or 1, 2 or 3-fluoro;

$Y^1$ is O, $S(O)_m$, —$C(O)NX^6$—, —$CH$=$CH$—, —$C$≡$C$—, —$N(X^6)C(O)$—, —$C(O)NX^6$—, —$C(O)O$—, —$OC(O)N(X^6)$— or —$OC(O)$—;

q is 0, 1, 2, 3 or 4;

t is 0, 1, 2 or 3;

said $(CH_2)_q$ group and $(CH_2)_t$ group may each be optionally substituted with hydroxyl, ($C_1$–$C_4$) alkoxy, carboxyl, —$CONH_2$, —$S(O)_m(C_1$–$C_6)$alkyl, —$CO_2(C_1$–$C_4)$alkyl ester, 1H-tetrazol-5-yl, 1, 2 or 3-fluoro, or 1 or 2 ($C_1$–$C_4$)alkyl;

$R^2$ is hydrogen, ($C_1$–$C_8$)alkyl, —($C_0$–$C_3$)alkyl-($C_3$–$C_8$) cycloalkyl, —($C_1$–$C_4$)alkyl-$A^1$ or $A^1$;

where the alkyl groups and the cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1$–$C_6)$alkyl, —$C(O)A^1$, —$C(O)(X^6)$, $CF_3$, CN or 1, 2 or 3 halogen;

$R^3$ is $A^1$, ($C_1$–$C_{10}$)alkyl, —($C_1$–$C_6$)alkyl-$A^1$, —($C_1$–$C_6$) alkyl-($C_3$–$C_7$)cycloalkyl, —($C_1$–$C_5$)alkyl-$X^1$—($C_1$–$C_5$)alkyl, —($C_1$–$C_5$) alkyl-$X^1$-($C_0$–$C_5$)alkyl-$A^1$ or —($C_1$–$C_5$)alkyl-$X^1$-($C_1$–$C_5$)alkyl-($C_3$–$C_7$)cycloalkyl;

where the alkyl groups in the definition of $R^3$ are optionally substituted with, —$S(O)_m(C_1$–$C_6)$alkyl, —$C(O)OX^3$, 1, 2, 3, 4 or 5 halogens, or 1, 2 or 3 $OX^3$;

$X^1$ is O, $S(O)_m$, —$N(X^2)C(O)$—, —$C(O)N(X^2)$—, —$OC(O)$—, —$C(O)O$—, —$CX^2$=$CX^2$—, —$N(X^2)$ $C(O)O$—, —$OC(O)N(X^2)$— or —$C$≡$C$—;

$R^4$ is hydrogen, ($C_1$–$C_6$)alkyl or ($C_3$–$C_7$)cycloalkyl;

$X^4$ is hydrogen or ($C_1$–$C_6$)alkyl or $X^4$ is taken together with $R^4$ and the nitrogen atom to which $X^4$ is attached and the carbon atom to which $R^4$ is attached and form a five to seven membered ring;

$R^6$ is

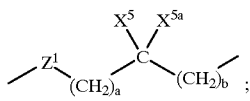

where a and b are independently 0, 1, 2 or 3;
$X^5$ and $X^{5a}$ are each independently selected from the group consisting of hydrogen, trifluoromethyl, $A^1$ and optionally substituted ($C_1$–$C_6$)alkyl;
    the optionally substituted ($C_1$–$C_6$)alkyl in the definition of $X^5$ and $X^{5a}$ is optionally substituted with a substituent selected from the group consisting of $A^1$, $OX^2$, —S(O)$_m$($C_1$–$C_6$)alkyl, —C(O)$OX^2$, ($C_3$–$C_7$)cycloalkyl, —N($X^2$)($X^2$) and —C(O)N($X^2$)($X^2$);
$Z^1$ is a bond, O or N—$X^2$, provided that when a and b are both 0 then $Z^1$ is not N—$X^2$ or O;
$R^7$ and $R^8$ are independently hydrogen or optionally substituted ($C_1$–$C_6$)alkyl;
    where the optionally substituted ($C_1$–$C_6$)alkyl in the definition of $R^7$ and $R^8$ is optionally independently substituted with $A^1$, —C(O)O—($C_1$–$C_6$)alkyl, —S(O)$_m$($C_1$–$C_6$)alkyl, 1 to 5 halogens, 1 to 3 hydroxy, 1 to 3—O—C(O)($C_1$–$C_{10}$)alkyl or 1 to 3 ($C_1$–$C_6$)alkoxy; or
$R^7$ and $R^8$ can be taken together to form —(CH$_2$)$_r$—L—(CH$_2$)$_r$—;
    where L is C($X^2$)($X^2$), S(O)$_m$ or N($X^2$);
$A^1$ in the definition of $R^1$ is ($C_5$–$C_7$)cycloalkenyl, phenyl or a partially saturated, fully saturated or fully unsaturated 4- to 8-membered ring, a bicyclic ring system consisting of a partially saturated, fully unsaturated or fully saturated 5- or 6-membered ring, fused to a partially saturated, fully saturated or fully unsaturated 5- or 6-membered ring;
$A^1$ in the definition of $R^2$, $R^3$, $R^6$, $R^7$ and $R^8$ is independently ($C_5$–$C_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
    $A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —C(O)N($X^6$)($X^6$), —C(O)$OX^6$, oxo, ($C_1$–$C_6$)alkyl, nitro, cyano, benzyl, —S(O)$_m$($C_1$–$C_6$)alkyl, 1H-tetrazol-5-yl, phenyl, phenoxy, phenylalkyloxy, halophenyl, methylenedioxy, —N($X^6$)($X^6$), —N($X^6$)C(O)($X^6$), —SO$_2$N($X^6$)($X^6$), —N($X^6$)SO$_2$-phenyl, —N($X^6$)SO$_2$$X^6$, —CONX$^{11}$X$^{12}$, —SO$_2$NX$^{11}$X$^{12}$, —NX$^6$SO$_2$X$^{12}$, —NX$^6$CONX$^{11}$X$^{12}$, —NX$^6$SO$_2$NX$^{11}$X$^{12}$, —NX$^6$C(O)X$^{12}$, imidazolyl, thiazolyl or tetrazolyl, provided that if $A^1$ is optionally substituted with methylenedioxy then it can only be substituted with one methylenedioxy;
    where $X^{11}$ is hydrogen or optionally substituted ($C_1$–$C_6$)alkyl;
        the optionally substituted ($C_1$–$C_6$)alkyl defined for $X^{11}$ is optionally independently substituted with phenyl, phenoxy, ($C_1$–$C_6$)alkoxycarbonyl, —S(O)$_m$($C_1$–$C_6$)alkyl 1 to 5 halogens, 1 to 3 hydroxy, 1 to 3 ($C_1$–$C_{10}$)alkanoyloxy or 1 to 3 ($C_1$–$C_6$)alkoxy;
    $X^{12}$ is hydrogen, ($C_1$–$C_6$)alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;
    or $X^{11}$ and $X^{12}$ are taken together to form —(CH$_2$)$_r$—$L^1$—(CH$_2$)$_r$—;
        where $L^1$ is C($X^2$)($X^2$), O, S(O)$_m$ or N($X^2$);
r for each occurrence is independently 1, 2 or 3;
$X^2$ for each occurrence is independently hydrogen, optionally substituted ($C_1$–$C_6$)alkyl, or optionally substituted ($C_3$–$C_7$)cycloalkyl, where the optionally substituted ($C_1$–$C_6$)alkyl and optionally substituted ($C_3$–$C_7$)cycloalkyl in the definition of $X^2$ are optionally independently substituted with —S(O)$_m$($C_1$–$C_6$)alkyl, —C(O)$OX^3$, 1 to 5 halogens or 1–3 $OX^3$;
$X^3$ for each occurrence is independently hydrogen or ($C_1$–$C_6$)alkyl;
$X^6$ is independently hydrogen, optionally substituted ($C_1$–$C_6$)alkyl, ($C_2$–$C_6$)halogenated alkyl, optionally substituted ($C_3$–$C_7$)cycloalkyl, ($C_3$–$C_7$)-halogenatedcycloalkyl, where optionally substituted ($C_1$–$C_6$)alkyl and optionally substituted ($C_3$–$C_7$) cycloalkyl in the definition of $X^6$ is optionally independently substituted by 1 or 2 ($C_1$–$C_4$)alkyl, hydroxyl, ($C_1$–$C_4$)alkoxy, carboxyl, $CONH_2$, —S(O)$_m$($C_1$–$C_6$) alkyl, carboxylate ($C_1$–$C_4$)alkyl ester, or 1H-tetrazol-5-yl; or when there are two x6 groups on one atom and both $x^6$ are independently ($C_1$–$C_6$)alkyl, the two ($C_1$–$C_6$)alkyl groups may be optionally joined and, together with the atom to which the two $X^6$ groups are attached, form a 4- to 9-membered ring optionally having oxygen, sulfur or $NX^7$;
$X^7$ is hydrogen or ($C_1$–$C_6$)alkyl optionally substituted with hydroxyl; and
m for each occurrence is independently 0, 1 or 2;
with the proviso that:
    $X^6$ and $X^{12}$ cannot be hydrogen when it is attached to C(O) or SO$_2$ in the form C(O)$X^6$, C(O)$X^{12}$, SO$_2$$X^6$ or SO$_2$$X^{12}$; and
    when $R^6$ is a bond then L is N($X^2$) and each r in the definition —(CH$_2$)$_r$—L—(CH$_2$)$_r$— is independently 2 or 3;
    which is effective in promoting release of endogenous growth hormone; and
wherein the human or other animal is in need of immune system stimulation.

9. A method of claim 8 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide.

10. A method of claim 8 wherein the compound is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide, L-tartaric acid salt.

* * * * *

UNITED STATES PATENT AND TRADEMARK OFFICE
CERTIFICATE OF CORRECTION

PATENT NO.    : 6,313,140 B1                                                          Page 1 of 1
DATED         : November 6, 2001
INVENTOR(S)   : Philip A. Carpino et al.

It is certified that error appears in the above-identified patent and that said Letters Patent is hereby corrected as shown below:

Column 86, line 50, Column 89, line 51 and Column 93, line 1,
Immediately before the structure

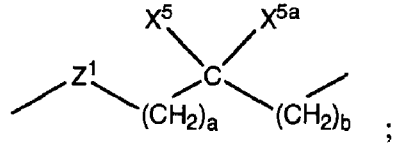

insert the phrase -- $R^6$ is --.

Column 86, line 57, Column 89, line 57 and Column 93, line 7,
Delete the phrase "$R^6$ is".

Signed and Sealed this

Tenth Day of February, 2004

JON W. DUDAS
*Acting Director of the United States Patent and Trademark Office*